US009023579B2

United States Patent
Yamaguchi et al.

(10) Patent No.: US 9,023,579 B2
(45) Date of Patent: May 5, 2015

(54) ACTINIC-RAY- OR RADIATION-SENSITIVE RESIN COMPOSITION, COMPOUND AND METHOD OF FORMING PATTERN USING THE COMPOSITION

(75) Inventors: Shuhei Yamaguchi, Shizuoka (JP); Akinori Shibuya, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/485,793

(22) Filed: May 31, 2012

(65) Prior Publication Data
US 2012/0237874 A1    Sep. 20, 2012

Related U.S. Application Data

(63) Continuation-in-part of application No. 12/833,668, filed on Jul. 9, 2010, now abandoned.

(30) Foreign Application Priority Data

Jul. 10, 2009  (JP) .................................. 2009-164131
Jun. 30, 2010  (JP) .................................. 2010-150181

(51) Int. Cl.
G03F 7/004      (2006.01)
G03F 7/00       (2006.01)
(Continued)

(52) U.S. Cl.
CPC .............. C07C 309/06 (2013.01); C07C 309/17 (2013.01); C07C 311/48 (2013.01);
(Continued)

(58) Field of Classification Search
USPC ............... 430/270.1, 325, 326; 546/141, 146, 546/153, 246, 189; 544/5, 374; 564/82; 562/113; 560/149; 549/13, 80, 78
See application file for complete search history.

(56) References Cited

U.S. PATENT DOCUMENTS

| | | |
|---|---|---|
| 6,187,504 B1 | 2/2001 | Suwa et al. |
| 6,908,722 B2 | 6/2005 | Ebata et al. |

(Continued)

FOREIGN PATENT DOCUMENTS

| | | |
|---|---|---|
| EP | 1586570 A1 * | 10/2005 |
| EP | 1635218 A2 | 3/2006 |

(Continued)

OTHER PUBLICATIONS

Office Action dated Feb. 25, 2014, issued by the Japanese Patent and Trademark Office in counterpart Japanese Patent Application No. 2010-150181, English translation.

*Primary Examiner* — Cynthia H Kelly
*Assistant Examiner* — Alyssa L Cepluch
(74) *Attorney, Agent, or Firm* — Sughrue Mion, PLLC

(57) ABSTRACT

According to one embodiment, an actinic-ray- or radiation-sensitive resin composition includes any of the compounds (A) of general formula (I) below that when exposed to actinic rays or radiation, generates an acid and a resin (B) whose rate of dissolution into an alkali developer is increased by the action of an acid. (The characters used in general formula (I) have the meanings mentioned in the description.)

(I)

$$\left[\left(\underset{n}{\underset{\phantom{X}}{\bigcirc}}\underset{(R_3)_p}{\overset{(R_2)_o}{\bigcirc}}\right)_m\overset{\oplus}{S}{-}(R_1)_l\right]X^{\ominus}$$

22 Claims, 2 Drawing Sheets

(51) Int. Cl.

| | | |
|---|---|---|
| *C07C 311/00* | (2006.01) | |
| *C07C 309/39* | (2006.01) | |
| *C07C 309/06* | (2006.01) | |
| *C07C 309/17* | (2006.01) | |
| *C07C 311/48* | (2006.01) | |
| *C07C 381/12* | (2006.01) | |
| *C07D 215/58* | (2006.01) | |
| *C07D 217/08* | (2006.01) | |
| *C07D 307/33* | (2006.01) | |
| *C07D 307/93* | (2006.01) | |
| *C07D 333/16* | (2006.01) | |
| *C07D 333/46* | (2006.01) | |
| *C07D 335/02* | (2006.01) | |
| *C07D 409/02* | (2006.01) | |
| *C07D 409/14* | (2006.01) | |
| *C07D 417/02* | (2006.01) | |
| *G03F 7/039* | (2006.01) | |
| *G03F 7/20* | (2006.01) | |
| *G03F 7/11* | (2006.01) | |

(52) U.S. Cl.
CPC .......... *C07C381/12* (2013.01); *C07C 2101/14* (2013.01); *C07C 2103/74* (2013.01); *C07D 215/58* (2013.01); *C07D 217/08* (2013.01); *C07D 307/33* (2013.01); *C07D 307/93* (2013.01); *C07D 333/16* (2013.01); *C07D 333/46* (2013.01); *C07D 335/02* (2013.01); *C07D 409/02* (2013.01); *C07D 409/14* (2013.01); *C07D 417/02* (2013.01); *G03F 7/0045* (2013.01); *G03F 7/0046* (2013.01); *G03F 7/0397* (2013.01); *G03F 7/2041* (2013.01); *G03F 7/11* (2013.01)

(56) References Cited

U.S. PATENT DOCUMENTS

| | | | |
|---|---|---|---|
| 7,501,220 B2 | 3/2009 | Hirayama et al. | |
| 7,527,909 B2 | 5/2009 | Hirayama et al. | |
| 7,541,138 B2 | 6/2009 | Hirayama et al. | |
| 2004/0229162 A1* | 11/2004 | Ohsawa et al. | 430/270.1 |
| 2006/0141383 A1* | 6/2006 | Miyamatsu et al. | 430/270.1 |
| 2007/0042290 A1* | 2/2007 | Inabe et al. | 430/270.1 |
| 2007/0178405 A1 | 8/2007 | Kanda et al. | |
| 2008/0081293 A1* | 4/2008 | Harada et al. | 430/287.1 |
| 2008/0261150 A1* | 10/2008 | Tsubaki et al. | 430/270.1 |
| 2008/0292989 A1* | 11/2008 | Nishikawa | 430/287.1 |
| 2008/0305433 A1 | 12/2008 | Kanda et al. | |
| 2009/0325103 A1* | 12/2009 | Sato et al. | 430/270.1 |
| 2010/0310991 A1 | 12/2010 | Inabe et al. | |
| 2012/0009522 A1* | 1/2012 | Kato et al. | 430/283.1 |
| 2012/0015302 A1* | 1/2012 | Tango et al. | 430/285.1 |
| 2012/0115085 A1 | 5/2012 | Kanda et al. | |

FOREIGN PATENT DOCUMENTS

| | | | |
|---|---|---|---|
| JP | 10-232490 A | | 9/1998 |
| JP | 2004-002252 A | | 1/2004 |
| JP | 2004-012554 A | | 1/2004 |
| JP | 2006-084530 A | | 3/2006 |
| JP | 2007-052346 A | | 3/2007 |
| JP | 2007-178858 A | | 7/2007 |
| JP | 2007-304537 A | | 11/2007 |
| JP | 2008-052102 A | | 3/2008 |
| JP | 2008-169231 A | | 7/2008 |
| JP | 2008-290947 A | | 12/2008 |
| WO | 2004/068242 A1 | | 8/2004 |
| WO | WO 2010140709 A1 * | | 12/2010 |

* cited by examiner

ACTINIC-RAY- OR RADIATION-SENSITIVE RESIN COMPOSITION, COMPOUND AND METHOD OF FORMING PATTERN USING THE COMPOSITION

CROSS-REFERENCE TO RELATED APPLICATIONS

This application is a Continuation-in-Part application of U.S. patent application Ser. No. 12/833,668, filed Jul. 9, 2010 and based upon and claiming the benefit of priority from prior Japanese Patent Applications No. 2009-164131, filed Jul. 10, 2009; and No. 2010-150181, filed Jun. 30, 2010, the entire contents of all of which are incorporated herein by reference.

BACKGROUND OF THE INVENTION

1. Field of the Invention

The present invention relates to an actinic-ray- or radiation-sensitive resin composition, compounds and a method of forming a pattern using the composition. In particular, the present invention relates to an actinic-ray- or radiation-sensitive resin composition and compounds employed in a semiconductor production process for an IC or the like, a circuit board production process for a liquid crystal, a thermal head or the like and other photofabrication processes, and also relates to a method of forming a pattern with the use of the composition. More particularly, the present invention relates to an actinic-ray- or radiation-sensitive resin composition that is suitable when, for example, electron beams or far-ultraviolet rays of wavelength 250 nm or shorter, preferably 220 nm or shorter are used as an exposure light source, and also relates to a method of forming a pattern with the use of the composition.

In the present invention, the terms "actinic rays" and "radiation" mean, for example, brightline spectra from a mercury lamp, far ultraviolet represented by an excimer laser, extreme ultraviolet, X-rays, electron beams and the like. In the present invention, the term "light" means actinic rays or radiation.

2. Description of the Related Art

In photosensitive compositions, such as a chemical-amplification resist composition, for use in semiconductor photolithographic processing, etc., especially when an ArF excimer laser (wavelength: 193 nm) is used as a light source, it is beneficial to employ a resin having an alicyclic hydrocarbon group from the viewpoint of transparency and resistance to dry etching.

Stronger acids are demanded for the photosensitive compositions containing the resin having an alicyclic hydrocarbon group. Thus, use is made of compounds that generate perfluoroalkylsulfonic acids, such as triphenylsulfonium trifluoromethanesulfonate or the like.

However, the perfluoroalkylsulfonic acids exhibit high hydrophobicity, so that the photosensitive compositions containing the acid generators that generate these acids have poor affinity to aqueous developers. Thus, it has been likely to encounter the problems that a decrease of sensitivity is caused by deteriorated developability and development defects occur.

In this connection, patent reference 1 discloses photosensitive compositions each containing a compound that generates a specified acid containing a fluorine atom.

However, further enhancement of various performances, especially exposure latitude and line edge roughness performances, is demanded in accordance with the further enhancement of pattern fineness.

Moreover, it is pointed out that in the application of a chemical-amplification resist to liquid-immersion exposure, the resist layer is brought into contact with the immersion liquid at the time of exposure to thereby alter the properties of the resist layer, and that components negatively affecting the immersion liquid are leached from the resist layer. Patent reference 2 describes examples in which the resist performance is changed by immersing the resist for ArF exposure in water before or after the exposure, and points out that this is a problem of the liquid-immersion exposure.

Patent reference 3 describes examples in which an acid generator with a specified sulfonimide structure is used in the liquid-immersion exposure.

Meanwhile, in the application of triarylsulfonium salts, such as triphenylsulfonium salts, to an ArF excimer laser, a high sensitivity and high quantum yield can be attained. However, the application is disadvantageous in that a strong absorption attributed to the benzene ring thereof causes the transmitted light to become less as the depth from the surface of a resist film is increased, resulting in the formation of a tapered pattern configuration. Therefore, various attempts are being made with respect to the photoacid generators for highly sensitive photoresists having high transparency at a wavelength of 193 nm.

As examples of such attempts, patent reference 4 proposed using sulfonium salt compounds each having an alkoxynaphthalene skeleton. Further, patent reference 5 proposed using sulfonium cation salts each having an alkoxynaphthalene skeleton in which the counter anion consisted of a sulfonimide. However, using these compounds, although the transparency in the region of far ultraviolet was high, was unsatisfactory in the lithographic performance.

PRIOR ART LITERATURE

Patent Reference

[Patent reference 1] Jpn. Pat. Appln. KOKAI Publication No. (hereinafter referred to as JP-A-) 2004-2252,
[Patent reference 2] International Publication No. 04/068242 (pamphlet),
[Patent reference 3] JP-A-2006-84530,
[Patent reference 4] JP-A-H10-232490, and
[Patent reference 5] JP-A-2004-12554.

BRIEF SUMMARY OF THE INVENTION

It is an object of the present invention to solve the problems of the technology for enhancing the original performance of microphotofabrication using far ultraviolet, EUV, electron beams, etc., especially an ArF excimer laser light. It is particular objects of the present invention to provide an excellent actinic-ray- or radiation-sensitive resin composition with which in both dry exposure and liquid-immersion exposure patternings, not only can development defects be suppressed but also a broad exposure latitude and regulation of line edge roughness can be attained and to provide a method of forming a pattern using the composition.

The inventors have found that the above objects can be attained by employing a composition in which a sulfonium salt having a specified group in its molecule is used as a photoacid generator, and the present invention has been completed on the basis of this finding. According to an aspect of embodiments, the present invention is as described below.

(1) An actinic-ray- or radiation-sensitive resin composition comprising any of the compounds (A) of general formula (I) below that when exposed to actinic rays or radiation, generates an acid and a resin (B) whose rate of dissolution into an alkali developer is increased by the action of an acid,

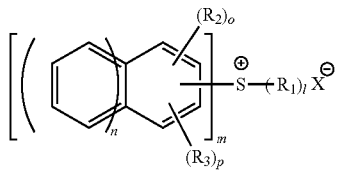

(I)

wherein $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; $X^-$ represents a counter anion; and n is 0 or 1, m is an integer of 1 to 3, l=3−m, o is an integer of 1 to 7, and p is an integer of 0 to 6, provided that when l is 2, two $R_1$s may be identical to or different from each other, and may be bonded to each other to thereby form a ring, and that $R_2$s, $R_3$s, and n's may be identical to or different from each other.

(2) The composition according to item (1), wherein in general formula (I), at least one $R_2$ is a group having an optionally substituted monocycloalkyl skeleton and having a total of 7 or more carbon atoms.

(3) The composition according to item (1) or (2), wherein in general formula (I), at least one $R_2$ is an optionally substituted monocycloalkyloxy group having a total of 7 or more carbon atoms, or an optionally substituted alkoxy group having a total of 7 or more carbon atoms in which a monocycloalkyl group is contained.

(4) The composition according to any of items (1) to (3), wherein in general formula (I), n=1, m=1, l=2, and two $R_1$s are optionally substituted alkyl groups or are bonded to each other to thereby form a ring.

(5) The composition according to any of items (1) to (4), further comprising a hydrophobic resin (C).

(6) The composition according to item (5), wherein the hydrophobic resin (C) contains at least a fluorine atom or a silicon atom.

(7) The composition according to any of items (1) to (6), wherein in general formula (I), $X^-$ has any of the structures of general formula (II) below,

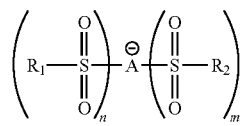

(II)

wherein A represents an oxygen atom, a nitrogen atom or a carbon atom; $R_1$ represents a monovalent organic group containing a fluorine atom; and $R_2$ represents a fluorine atom, an optionally substituted alkyl group, an optionally substituted cycloalkyl group or an optionally substituted aryl group, provided that when A is an oxygen atom, n=1 and m=0; when A is a nitrogen atom, n+m=2, n=1 or 2, and m=0 or 1, and when A is a carbon atom, n+m=3, n is an integer of 1 to 3, and m is an integer of 0 to 2, and that when n is 2 or greater, the two or more $R_1$s may be identical to or different from each other, and $R_1$s may be bonded to each other to thereby form a ring.

(8) The composition according to any of items (1) to (7), wherein any protonic solvent is not contained.

(9) Compounds of general formula (I),

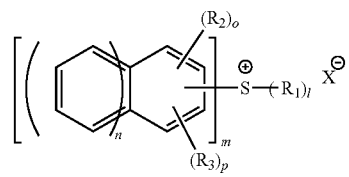

(I)

wherein $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; $X^-$ represents a counter anion; and n is 0 or 1, m is an integer of 1 to 3, l=3−m, o is an integer of 1 to 7, and p is an integer of 0 to 6, provided that when l is 2, two $R_1$s may be identical to or different from each other, and may be bonded to each other to thereby form a ring, and that $R_2$s, $R_3$s, and n's may be identical to or different from each other.

(10) The compounds according to item (9), wherein in general formula (I), at least one $R_2$ is a group having an optionally substituted monocycloalkyl skeleton and having a total of 7 or more carbon atoms.

(11) The compounds according to item (9) or (10), wherein in general formula (I), at least one $R_2$ is an optionally substituted monocycloalkyloxy group having a total of 7 or more carbon atoms, or an optionally substituted alkoxy group having a total of 7 or more carbon atoms in which a monocycloalkyl group is contained.

(12) The compounds according to any of items (9) to (11), wherein in general formula (I), n=1, m=1, l=2, and two $R_1$s are optionally substituted alkyl groups or are bonded to each other to thereby form a ring.

(13) A method of forming a pattern, comprising forming the composition of any of items (1) to (8) into a film, exposing the film and developing the exposed film.

(14) The method of forming a pattern according to item (13), wherein the film is exposed through a liquid for liquid immersion.

The present invention has made it feasible to suppress development defects and to provide a pattern excelling in the exposure latitude and line edge roughness performance.

BRIEF DESCRIPTION OF THE SEVERAL
VIEWS OF THE DRAWING

DETAILED DESCRIPTION OF THE INVENTION

Figures 1, 2:
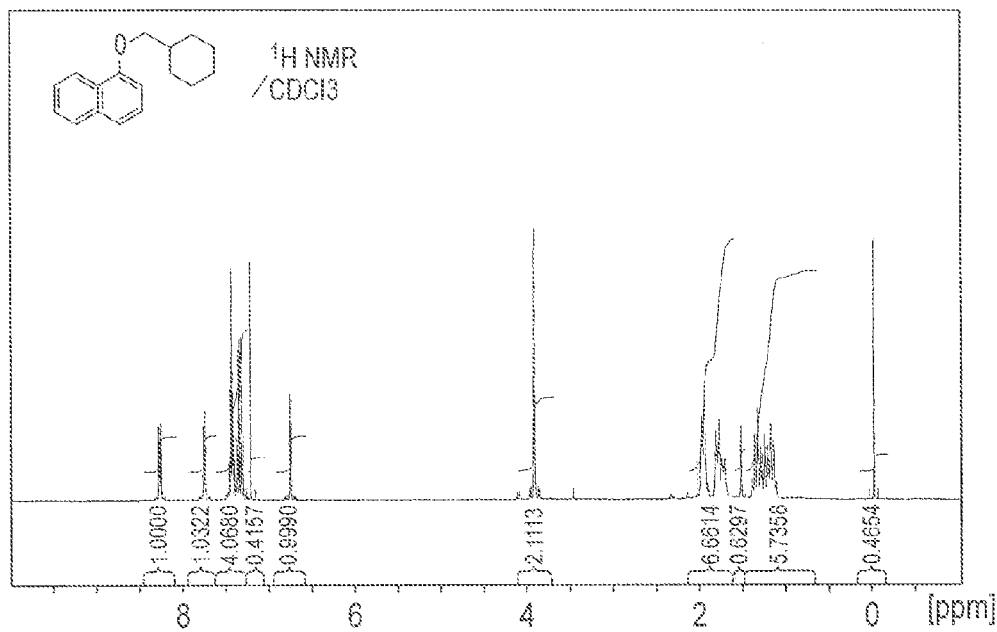
FIG. 1 is the $^1$HNMR chart of an intermediate compound 1 of photoacid generator (PAG1) prepared in an Example.
FIG. 2 is the $^1$HNMR chart of a photoacid generator (PAG1) prepared in an Example.

With respect to the expression of a group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

[(A) Photoacid Generator]

The compounds provided by the present invention are the compounds of general formula (I) below that when exposed to actinic rays or radiation, generate acids (hereinafter also referred to as "the compounds of the present invention," "the salts of the present invention," or the like). The compounds can be used as photoacid generators in the actinic-ray- or radiation-sensitive resin composition of the present invention.

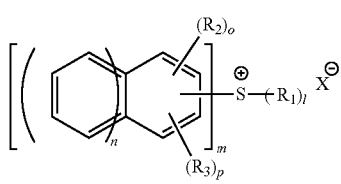
(I)

In general formula (I), $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; $X^-$ represents a counter anion; and n is 0 or 1, m is an integer of 1 to 3, l=3−m, o is an integer of 1 to 7, and p is an integer of 0 to 6, provided that when l is 2, two $R_1$s may be identical to or different from each other, and may be bonded to each other to thereby form a ring, and that $R_2$s, $R_3$s, and n's may be identical to or different from each other.

In general formula (I), when n=0, the moiety enclosed by the mark [ ] has a benzene-ring structure, while when n=1, the moiety enclosed by the mark [ ] has a naphthalene-ring structure.

General formula (I) will be described in greater detail below.

As the alkyl group represented by $R_1$, there can be mentioned methyl, ethyl, propyl, butyl, pentyl, hexyl, heptyl, octyl, dodecyl, 2-ethylhexyl, isopropyl, sec-butyl, t-butyl, isoamyl or the like. A substituent can be introduced in the alkyl group. As the substituent, there can be mentioned a hydroxyl group, a halogen atom (fluorine, chlorine, bromine or iodine), a nitro group, a cyano group, an amido group, a sulfonamido group, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group, or the like.

As the aryl group, there can be mentioned a benzene-series aromatic group such as phenyl, naphthyl or anthracyl, a heteroaromatic group such as indole, carbazole, thiophene, benzothiophene or dibenzothiophene, or the like. A substituent can be introduced in the aryl group. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group, or the like.

The aralkyl group consists of an alkyl group, such as methyl, ethyl, propyl, butyl, pentyl, hexyl, heptyl, octyl, dodecyl, 2-ethylhexyl, isopropyl, sec-butyl, t-butyl or isoamyl, substituted with any of the above-mentioned aryl groups. It is preferred for the aralkyl group to have a total of 7 to 30 carbon atoms, especially 7 to 15 carbon atoms.

The cycloalkyl groups include cycloalkenyl groups, and as such, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl, bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl and the like. A substituent can be introduced in the cycloalkyl groups. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group, or the like.

In the formula, preferably, m=1, and l=2. If so, two $R_1$s are preferably bonded to each other to thereby form a ring. The ring structure formed by the mutual bonding of $R_1$s is not particularly limited. Preferably, the ring has 5 to 7 members.

The group having a monocycloalkyl skeleton represented by $R_2$ preferably has a total of 7 or more carbon atoms, more preferably 7 to 15 carbon atoms.

$R_2$ is preferably an optionally substituted monocycloalkyloxy group having a total of 7 or more carbon atoms, or an optionally substituted alkoxy group having a total of 7 or more carbon atoms in which a monocycloalkyl group is contained.

The optionally substituted monocycloalkyloxy group having a total of 7 or more carbon atoms is a monocycloalkyloxy group composed of a cycloalkyloxy group, such as a cyclopropyloxy group, a cyclobutyloxy group, a cyclopentyloxy group, a cyclohexyloxy group, a cycloheptyloxy group, a cyclooctyloxy group or a cyclododecanyloxy group, optionally having a substituent selected from among an alkyl group such as methyl, ethyl, propyl, butyl, pentyl, hexyl, heptyl, octyl, dodecyl, 2-ethylhexyl, isopropyl, sec-butyl, t-butyl or isoamyl, a hydroxyl group, a halogen atom (fluorine, chlorine, bromine or iodine), a nitro group, a cyano group, an amido group, a sulfonamido group, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group and the like, provided that the sum of carbon atoms thereof including those of any optional substituent introduced in the cycloalkyl group is 7 or greater.

The optionally substituted alkoxy group having a total of 7 or more carbon atoms in which a monocycloalkyl group is contained is one composed of an alkoxy group, such as methoxy, ethoxy, propoxy, butoxy, pentyloxy, hexyloxy, heptoxy, octyloxy, dodecyloxy, 2-ethylhexyloxy, isopropoxy, sec-butoxy, t-butoxy or isoamyloxy, substituted with any of the above-mentioned optionally substituted monocycloalkyl groups, provided that the sum of carbon atoms thereof including those of the substituents is 7 or greater.

As the alkyl group represented by $R_3$, there can be mentioned methyl, ethyl, propyl, butyl, pentyl, hexyl, heptyl, octyl, dodecyl, 2-ethylhexyl, isopropyl, sec-butyl, t-butyl, isoamyl or the like. A substituent can be introduced in the alkyl group. As the substituent, there can be mentioned a hydroxyl group, a halogen atom (fluorine, chlorine, bromine or iodine), a nitro group, a cyano group, an amido group, a sulfonamido group, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group, or the like.

As the electron withdrawing group, there can be mentioned a cyano group, a trifluoromethyl group, a nitro group, a carboxyl group, a ketone group, an acyloxy group, a hydroxyl group, a perfluoroalkyl group, an alkylsulfone group, an alkoxy group such as methoxy, ethoxy, isopropoxy, t-butoxy or benzyloxy, or the like.

Preferably, o=1 to 3, p=0 to 2, and n=1.

Particular examples of the salts of general formula (I) according to the present invention will be shown below.

In the formulae, $X^-$ represents a counter anion.

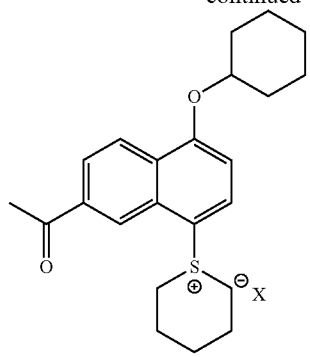

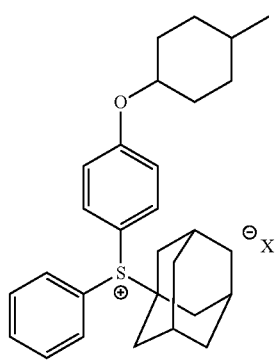

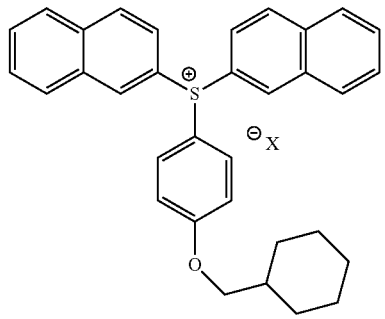

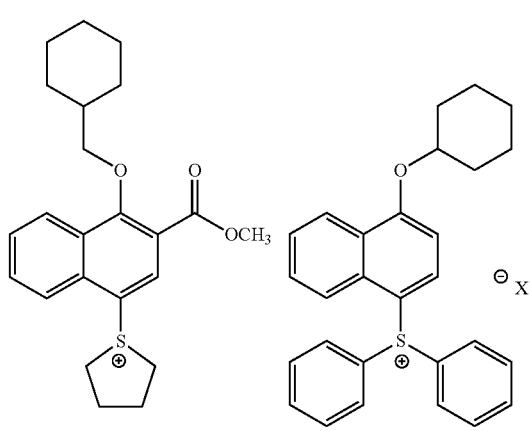

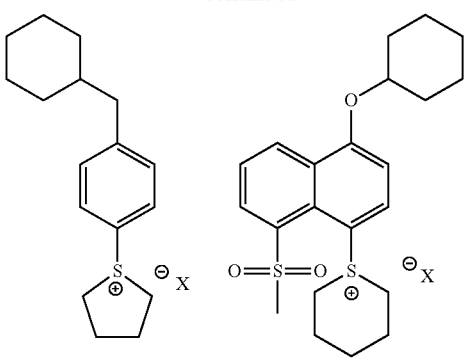
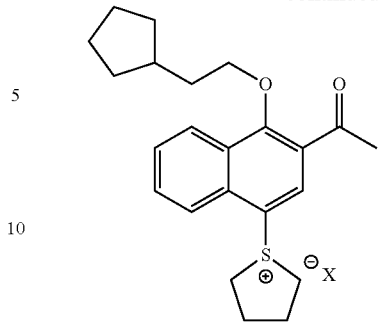
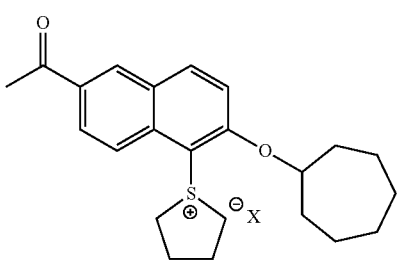
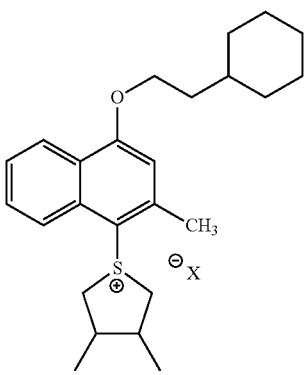
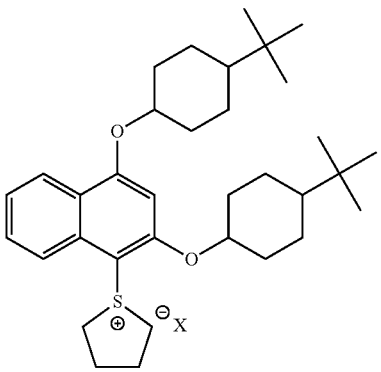
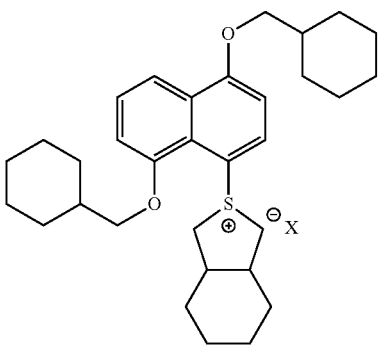
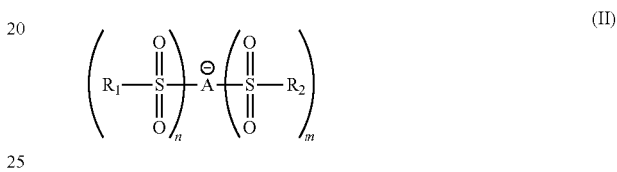

As the counter ion represented by X⁻, there can be mentioned any of the structures of general formula (II) below.

$$\left( R_1 - \underset{\underset{O}{\|}}{\overset{\overset{O}{\|}}{S}} - A \right)_n \left( \underset{\underset{O}{\|}}{\overset{\overset{O}{\|}}{S}} - R_2 \right)_m^{\ominus} \quad (II)$$

In general formula (II), A represents an oxygen atom, a nitrogen atom or a carbon atom.

$R_1$ represents a monovalent organic group containing a fluorine atom, preferably a monovalent organic group satisfying the relationship (mass of all fluorine atoms contained)/(mass of all atoms contained)≤0.35.

$R_2$ represents a fluorine atom, an optionally substituted alkyl group, an optionally substituted cycloalkyl group or an optionally substituted aryl group.

When A is an oxygen atom, n=1 and m=0. When A is a nitrogen atom, n+m=2, n=1 or 2, and m=0 or 1. When A is a carbon atom, n+m=3, n is an integer of 1 to 3, and m is an integer of 0 to 2. When n is 2 or greater, $R_1$s may be identical to or different from each other, and may be bonded to each other to thereby form a ring.

General formula (II) will be described in greater detail below.

$R_1$ represents a monovalent organic group containing a fluorine atom, preferably a monovalent organic group whose fluorine content expressed by the formula (mass of all fluorine atoms contained)/(mass of all atoms contained) is 0.35 or below. With respect to $R_1$, the fluorine content is preferably 0.30 or below, more preferably 0.25 or below.

As the monovalent organic group containing a fluorine atom represented by $R_1$, there can be mentioned an organic group containing, bonded to a sulfonyl group, an alkylene moiety substituted with at least one fluorine atom. It is preferred for the alkylene moiety to be a perfluoroalkylene group. The molecular end thereof is preferably substituted with a group with a ring structure, and the substitution may be carried out via a connecting group. It is preferred for this group with a ring structure to contain no fluorine atoms from the viewpoint of low fluorine content. As one form of the monovalent organic group represented by $R_1$, there can be mentioned the structure corresponding to $R_1$ shown in general formula (III) to be shown hereinafter.

The optionally substituted alkyl group, cycloalkyl group and aryl group represented by $R_2$ refer to a chain alkyl group, a monocyclic alkyl or alkenyl group, a polycyclic hydrocarbon group and a monocyclic aryl group. A substituent may be introduced in each of these chain alkyl group, monocyclic alkyl or alkenyl group, polycyclic hydrocarbon group and monocyclic aryl group. It is preferred for the substituent to contain a fluorine atom.

The chain alkyl group may be linear or branched. As such, there can be mentioned methyl, ethyl, propyl, butyl, pentyl, hexyl, heptyl, octyl, dodecyl, 2-ethylhexyl, isopropyl, sec-butyl, t-butyl, isoamyl or the like.

A substituent can be introduced in the chain alkyl group. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, or a carboxyl group.

As the monocyclic alkyl or alkenyl group, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl or the like. Cyclopropyl, cyclopentyl, cyclohexyl and cyclooctyl are especially preferred.

A substituent can be introduced in the monocyclic alkyl or alkenyl group. As the substituent, there can be mentioned a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, or a carboxyl group.

As the polycyclic hydrocarbon group, there can be mentioned bicyclo[4.3.0]nonanyl, decahydronaphthalenyl, tricyclo[5.2.1.0(2,6)]decanyl, bornyl, isobornyl, norbornyl, adamantyl, noradamantyl, 1,7,7-trimethyltricyclo[2.2.1.0$^{2,6}$]heptanyl, 3,7,7-trimethylbicyclo[4.1.0]heptanyl or the like. Norbornyl, adamantyl and noradamantyl are especially preferred.

The monocyclic aryl group refers to a substituted or unsubstituted phenyl group. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, or a carboxyl group.

It is preferred for $R_2$ to contain an electron withdrawing group from the viewpoint of acid strength. The electron withdrawing group is not particularly limited. As such, for example, there can be mentioned a cyano group, a trifluoromethyl group, a nitro group, a carboxyl group, a ketone group, an acyloxy group, a hydroxyl group, a perfluoroalkyl group, an alkoxy group such as methoxy, ethoxy, isopropoxy, t-butoxy or benzyloxy, a halogen atom such as fluorine or chlorine, or the like. Containing a fluorine atom is especially preferred. $R_2$ is more preferably a group containing a fluorine atom whose molecular weight is 220 or less, most preferably a trifluoromethyl group.

It is preferred for the counter anions of general formula (II), above, to have the structures of general formula (III) below.

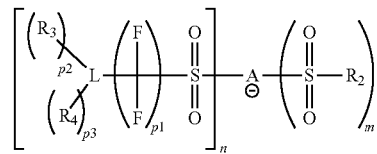
(III)

In general formula (III), A, $R_2$, m and n are as defined above in connection with general formula (II).

$R_3$, or each of $R_3$s independently, represents an optionally substituted alkyl group, an optionally substituted cycloalkyl group or an optionally substituted aryl group. $R_4$ represents a hydrogen atom.

L represents a single bond or a connecting group.

In the formula, p1 is an integer of 1 to 8, p2 is 1 or 2, and p3 is 0 or 1.

When p2 is 2, two $R_3$s may be bonded to each other to thereby form a ring structure. When n is 2 or greater, two or more $R_3$s may be bonded to each other to thereby form a ring structure.

As particular examples of the alkyl groups, cycloalkyl groups and aryl groups represented by $R_3$, there can be mentioned the same groups as set forth above with respect to the corresponding groups represented by $R_2$.

It is preferred for the $R_3$ groups to contain no fluorine atom from the viewpoint of low fluorine content.

L is preferably a single bond, an oxygen atom (—O—), a sulfur atom (—S—), a nitrogen atom (>N—), a carboxyl group (—OC=O—, —CO=O—), an amido group (>NC=O—) or a sulfonamido group (>NSO$_2$—). When p2 is 2 and two $R_3$s are bonded to each other to thereby form a ring, it is especially preferred for L to be a connecting group containing a nitrogen atom, such as an amido group or a sulfonamido group. If so, two $R_3$s are bonded to each other to thereby form a cycloamine residue containing the nitrogen atom on L within its ring.

As a cycloamine residue structure, there can be mentioned aziridine, azetidine, pyrrolidine, piperidine, hexamethyleneimine, heptamethyleneimine, piperazine, decahydroquinoline, 8-azabicyclo[3.2.1]octane, indole, oxazolidine, thiazolidine, 2-azanorbornane, 7-azanorbornane, morpholine, thiamorpholine or the like. A substituent may be introduced in these structures. As the substituent, there can be mentioned a hydroxyl group, a halogen atom (fluorine, chlorine, bromine or iodine), a nitro group, a cyano group, an amido group, a sulfonamido group, an alkyl group such as methyl, ethyl, propyl, n-butyl, sec-butyl, hexyl, 2-ethylhexyl or octyl, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl, benzoyl or carbonyl on the carbon as a constituent of a ring, an acyloxy group such as acetoxy or butyryloxy, or a carboxyl group.

Particular examples of the counter anion structures of general formula (II) according to the present invention will be shown below.

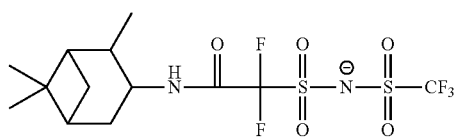

13
-continued
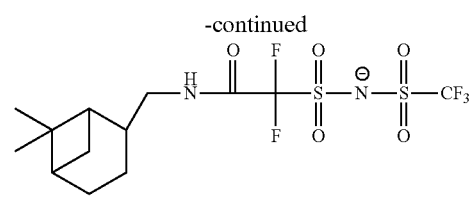
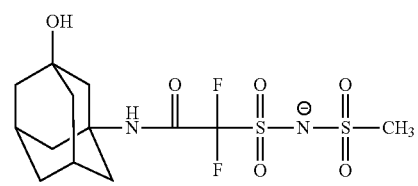
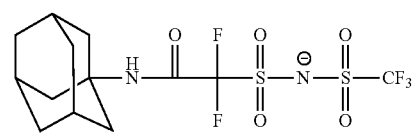
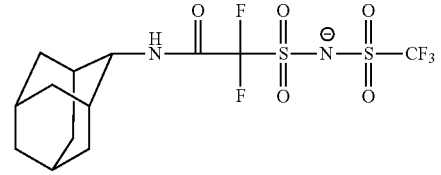
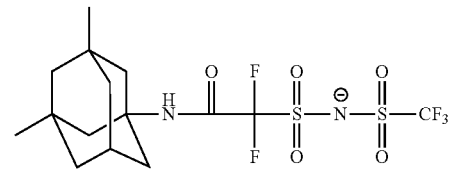
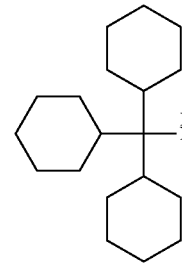
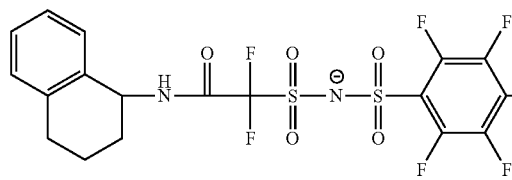
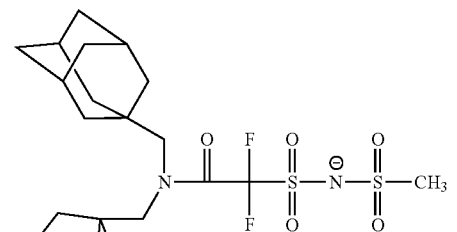
14
-continued
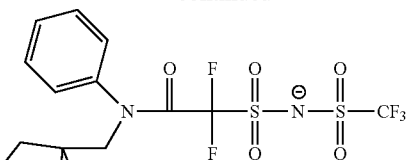
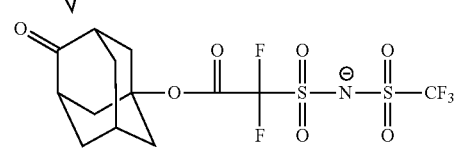
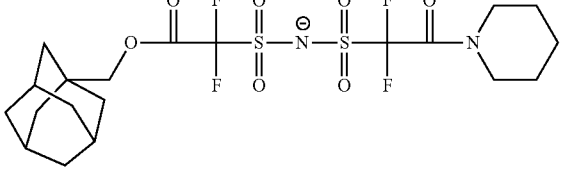
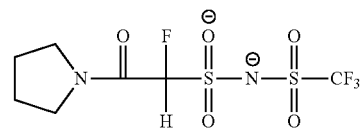
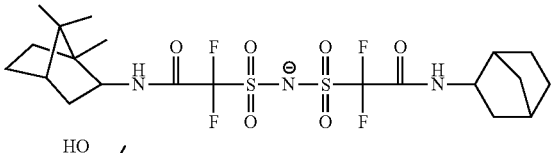
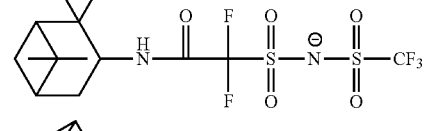
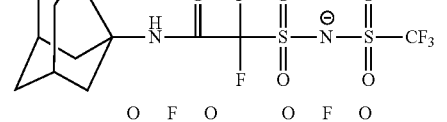
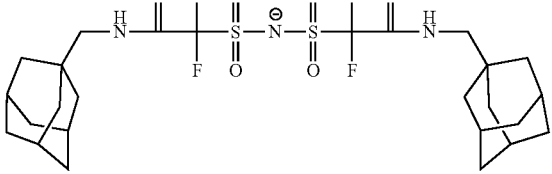
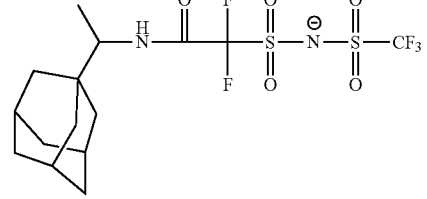
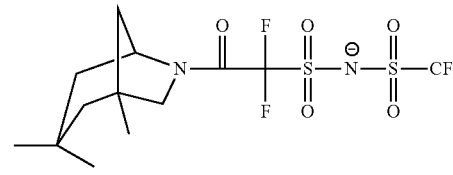

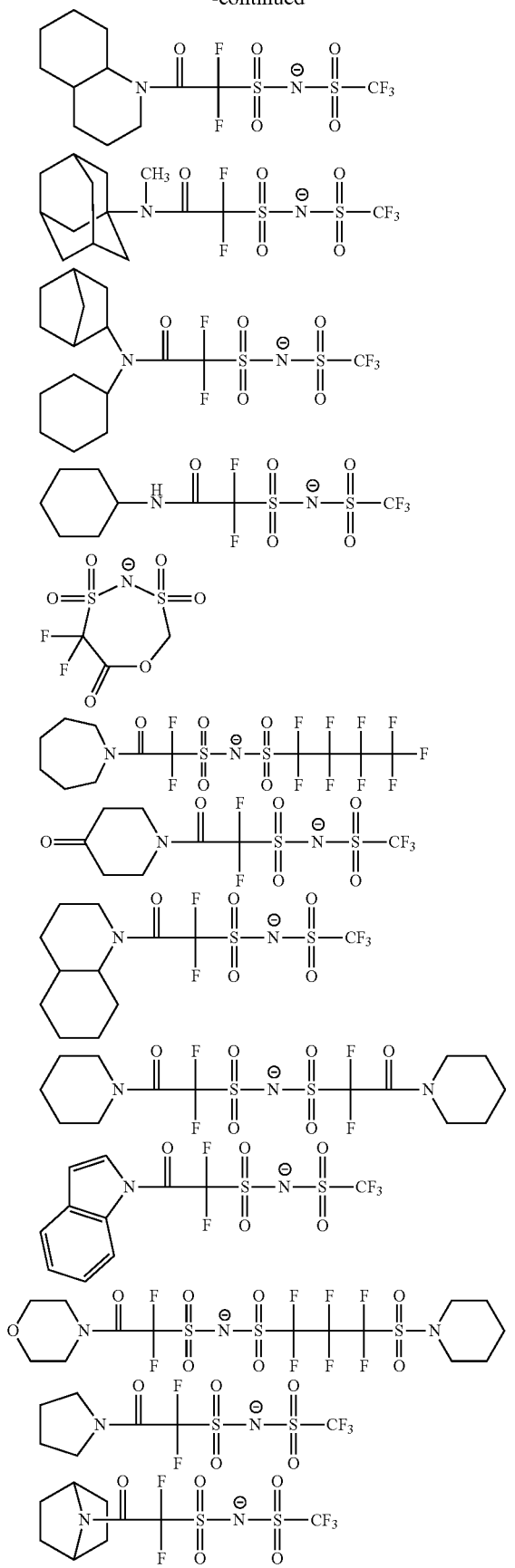
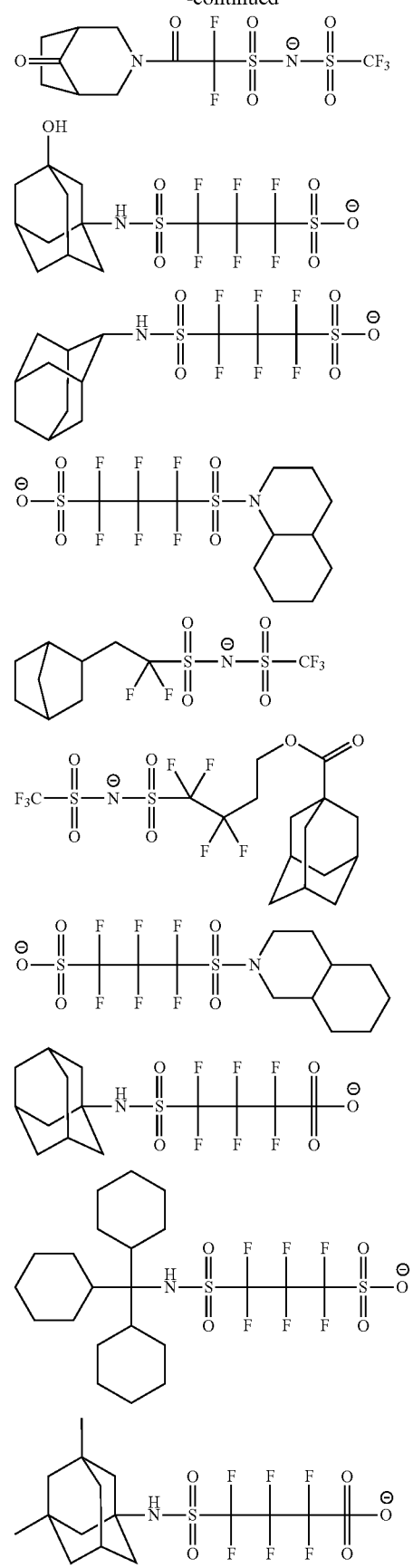

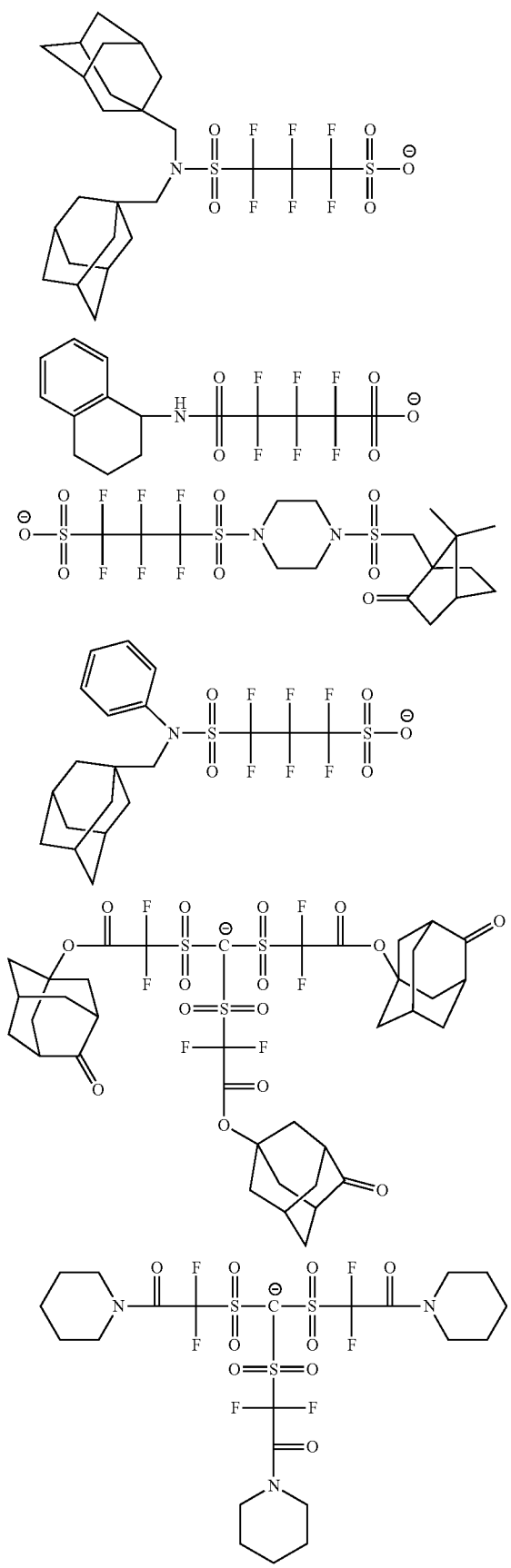
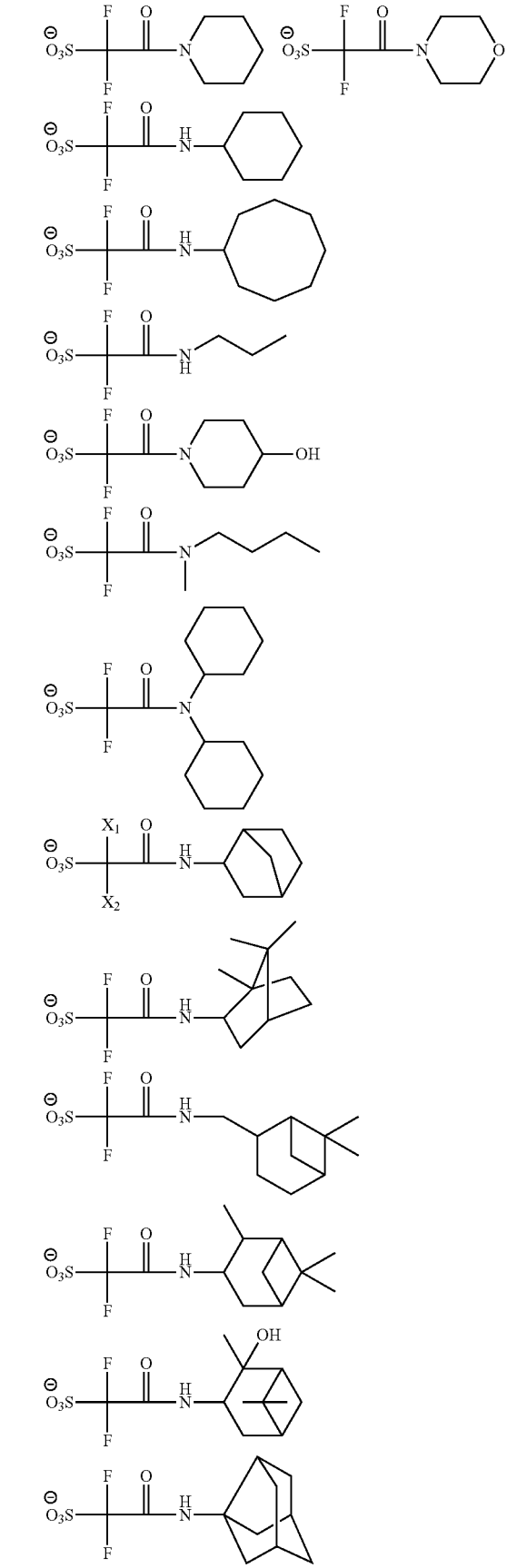

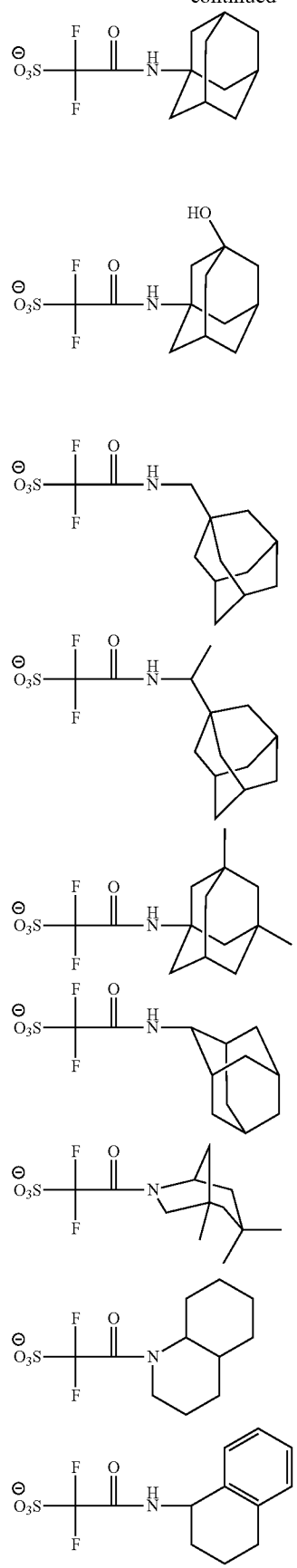
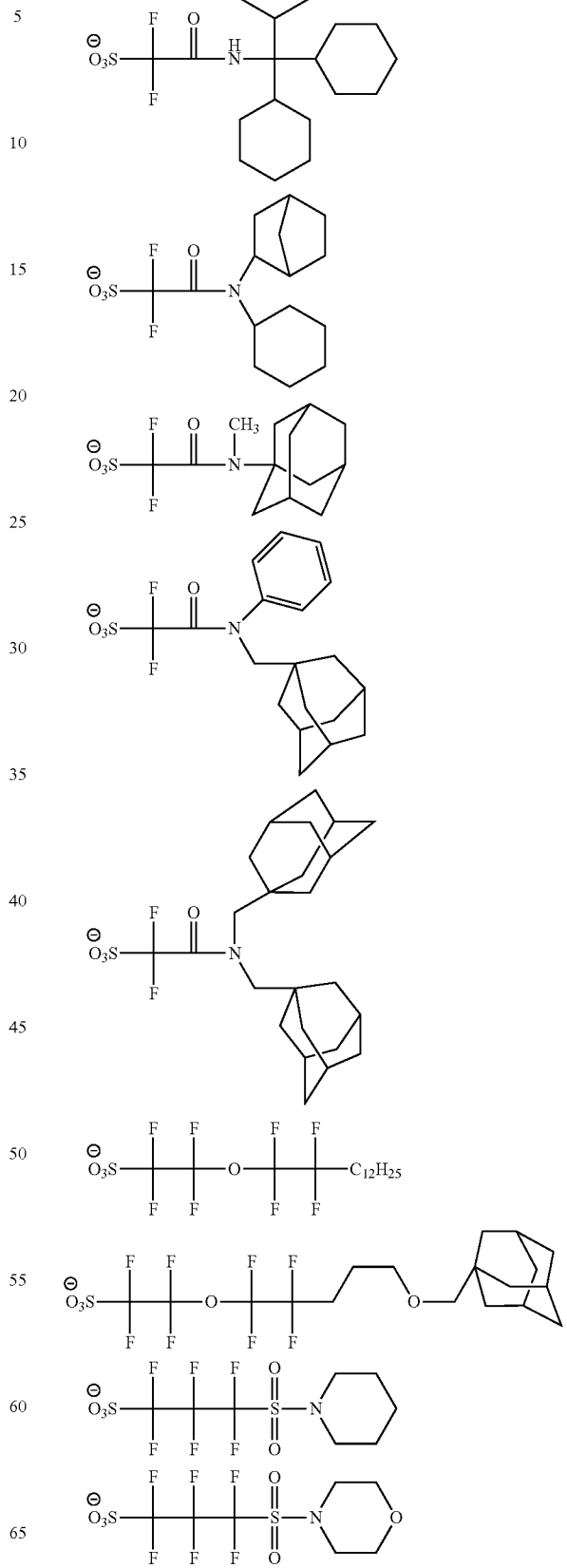

-continued
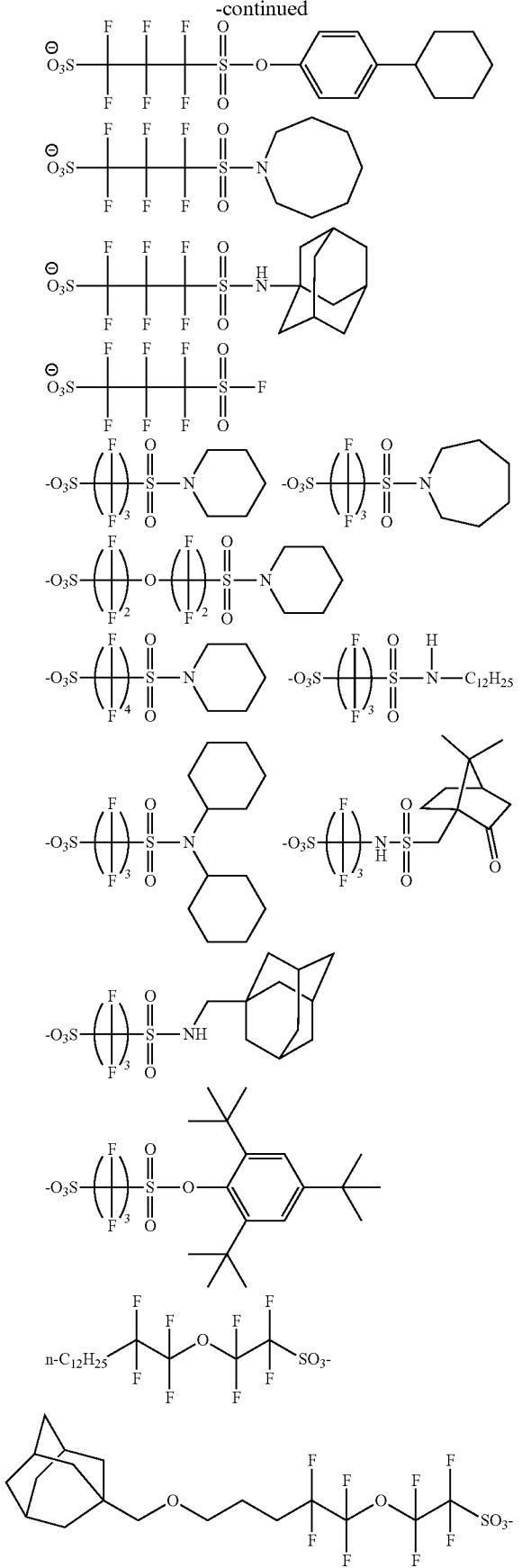
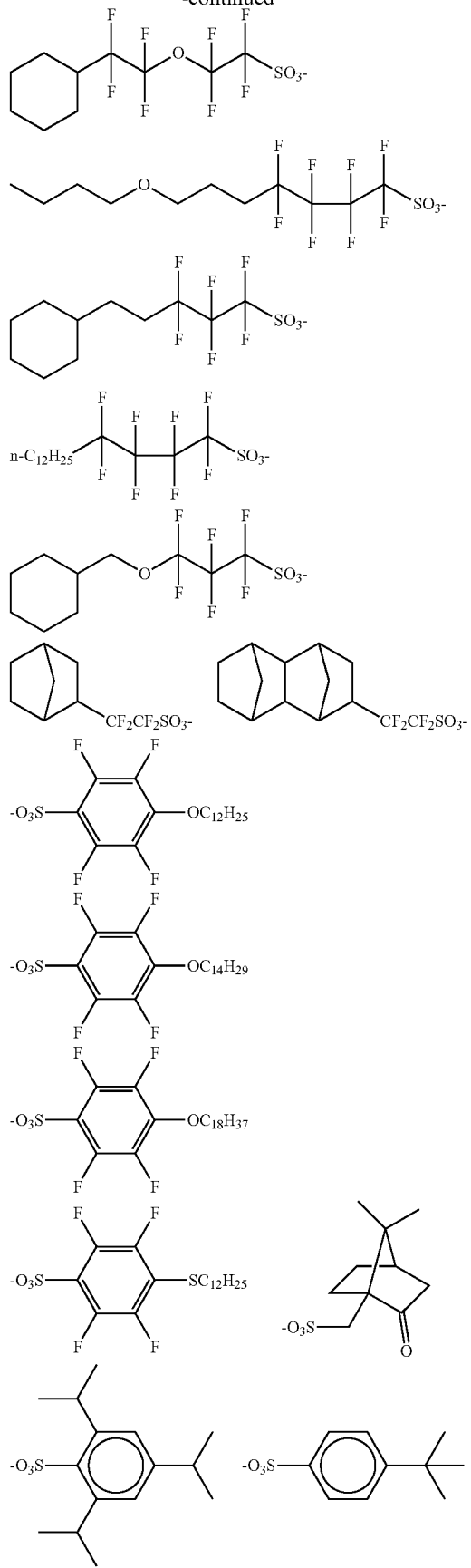

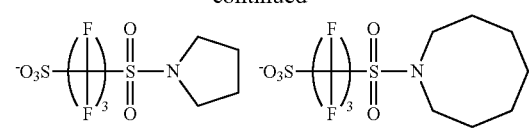
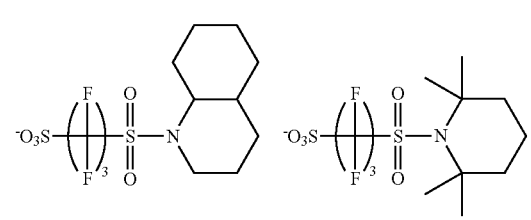
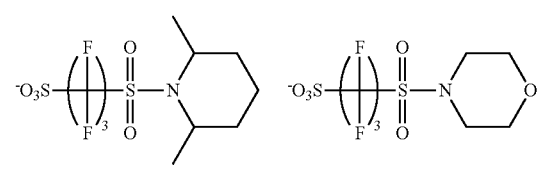
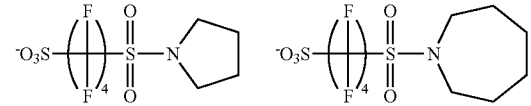
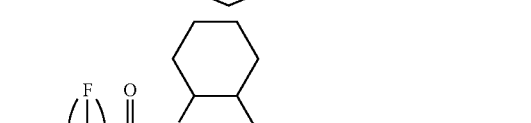
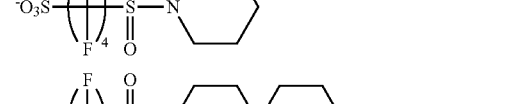
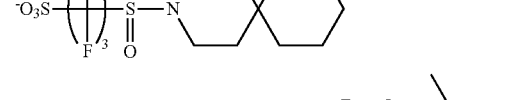
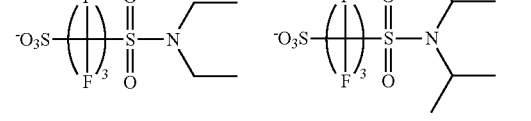
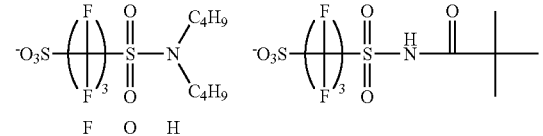
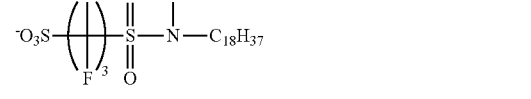
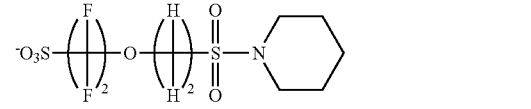
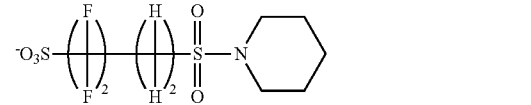
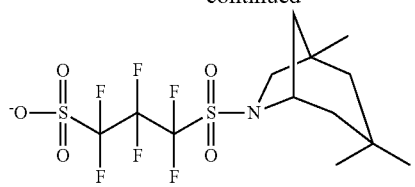
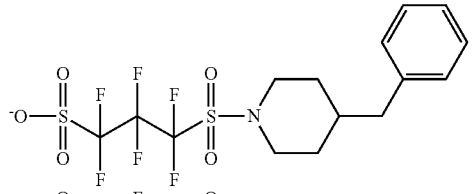
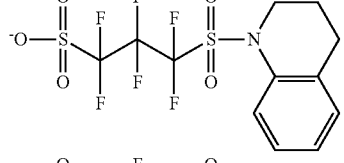
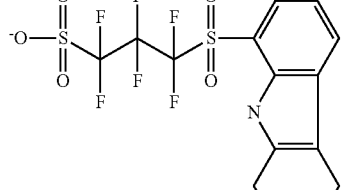
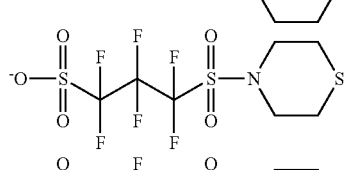
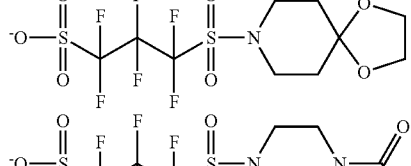
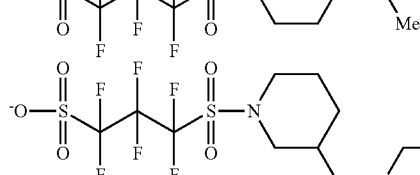
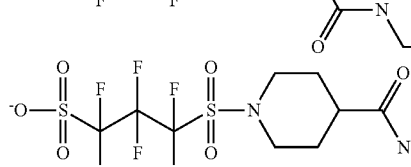
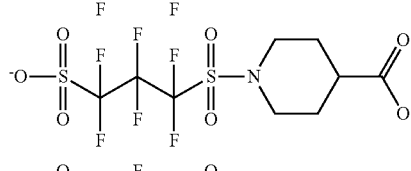
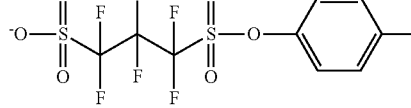

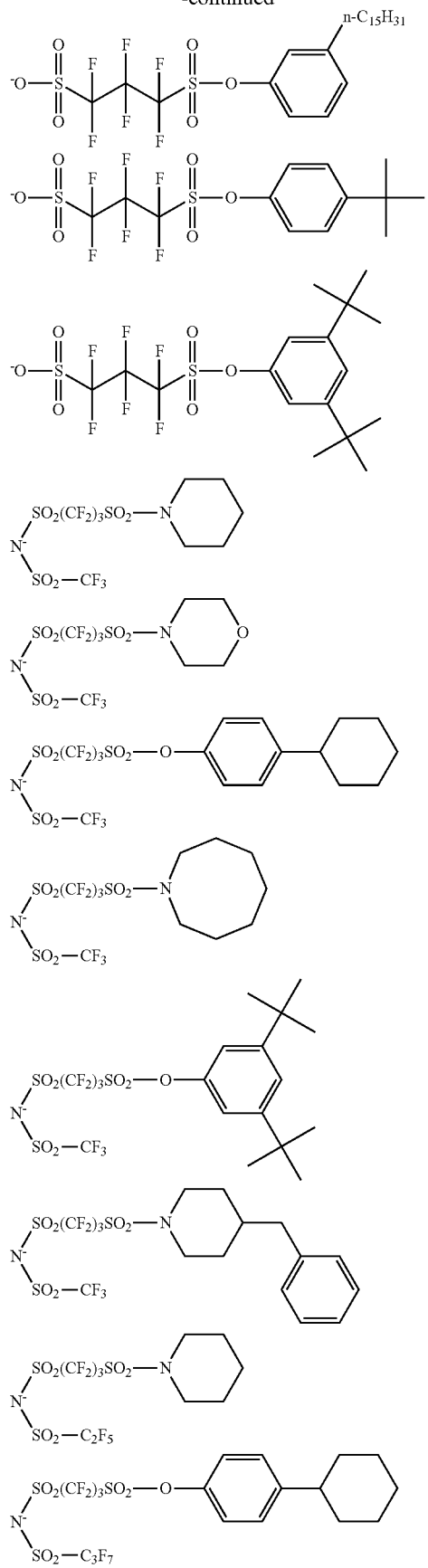
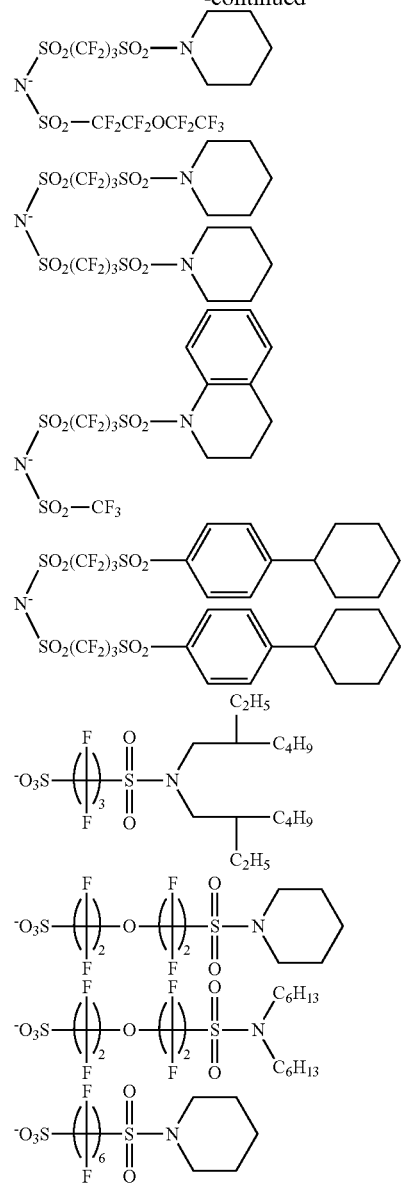
Specific examples of compounds of general formula (I) that generate an acid will be shown below, which however in no way limit the scope of the present invention.
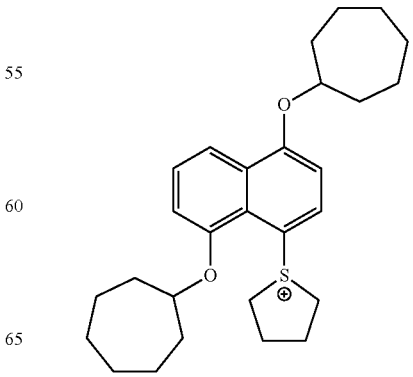

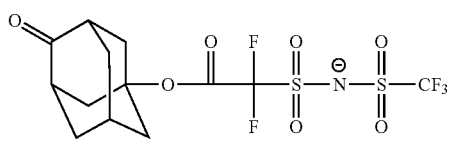
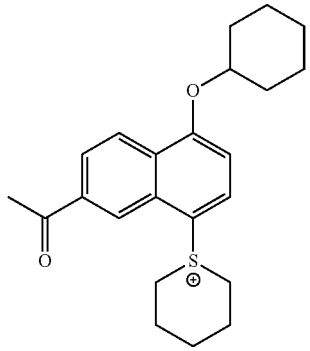
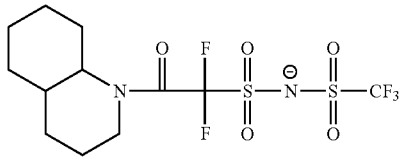
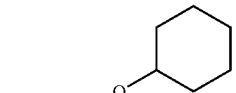
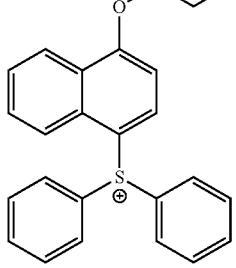
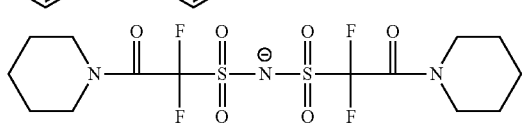
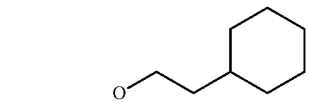
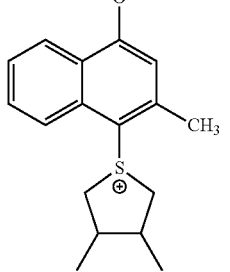
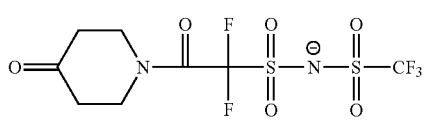
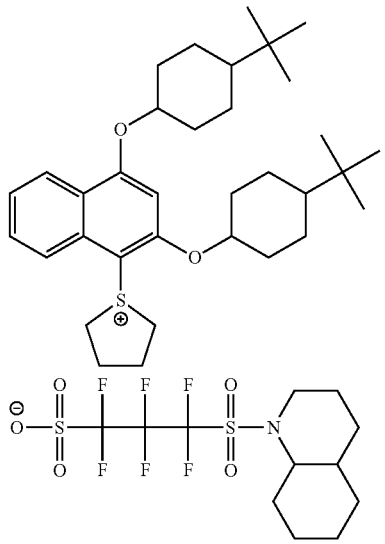
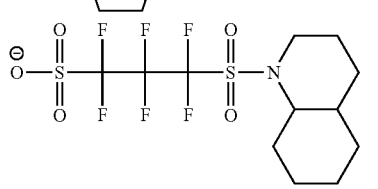
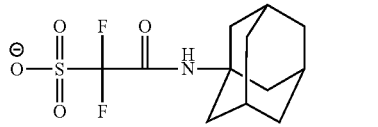

29
-continued
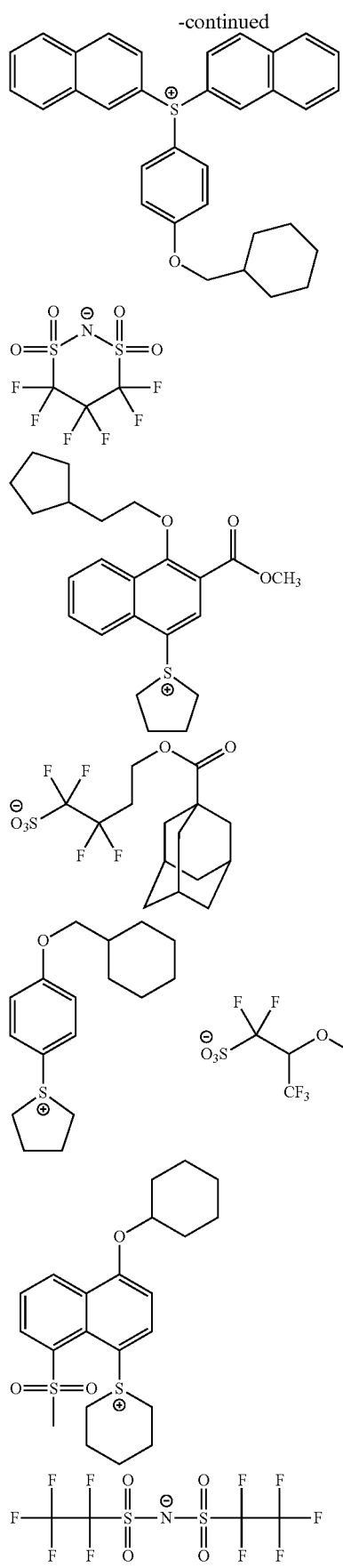
30
-continued
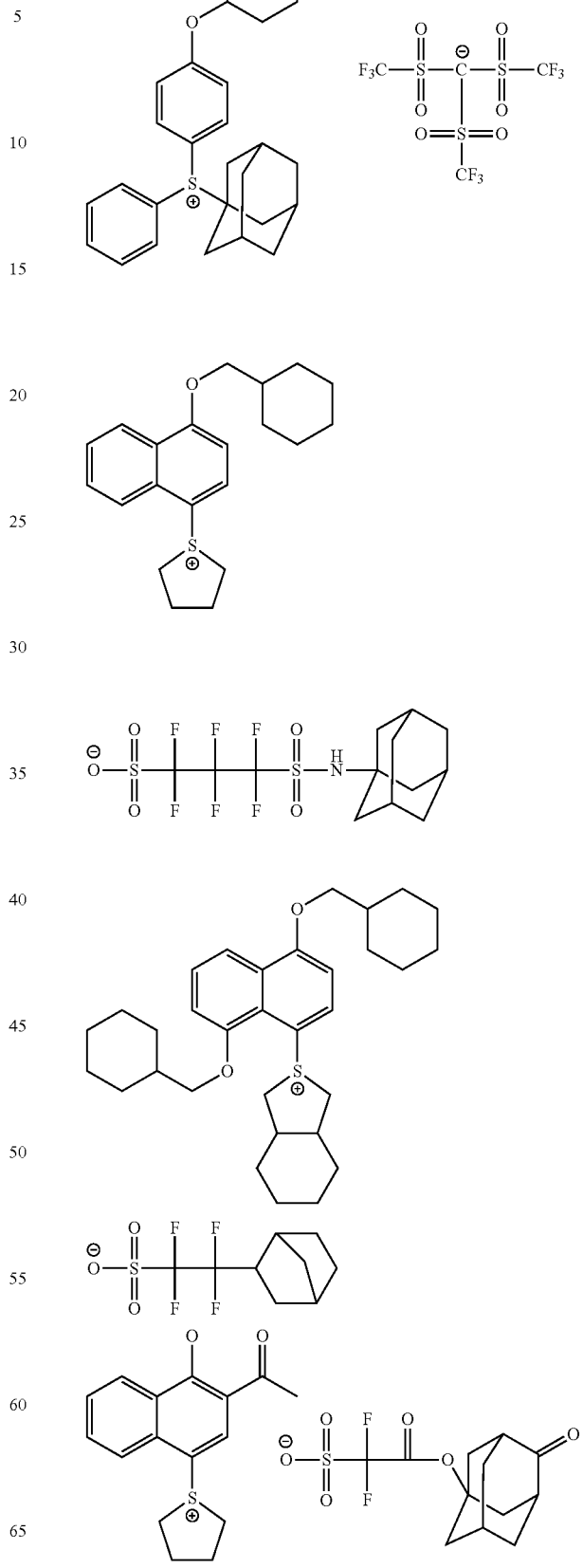

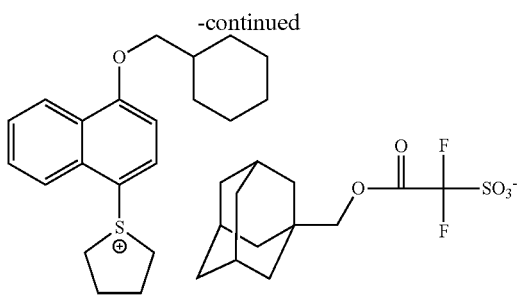

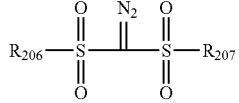

The above-mentioned photoacid generators (A) may be used individually or in combination.

The content of photoacid generators (A) together with other photoacid generators to be described below is preferably in the range of 1 to 60 mass %, more preferably 10 to 50 mass % and most preferably 15 to 35 mass % based on the total solids of the composition of the present invention.

[Other Photoacid Generator]

In the present invention, another compound that when exposed to actinic rays or radiation, is decomposed to thereby generate an acid may be used in combination with any of the photoacid generators (A). The amount of other photoacid generator used in combination with any of the photoacid generators (A) in terms of the molar ratio (photoacid generator (A)/other photoacid generator) is generally in the range of 100/0 to 20/80, preferably 100/0 to 40/60 and more preferably 100/0 to 50/50. As the other photoacid generators for use in combination with any of the photoacid generators (A), use can be made of a member appropriately selected from among a photoinitiator for photocationic polymerization, a photoinitiator for photoradical polymerization, a photo-achromatic agent and photo-discoloring agent for dyes, any of publicly known compounds that when exposed to actinic rays or radiation, generate an acid, employed in microresists, etc., and mixtures thereof.

For example, as the acid generator, there can be mentioned a diazonium salt, a phosphonium salt, a sulfonium salt, an iodonium salt, an imide sulfonate, an oxime sulfonate, diazosulfone, disulfone or o-nitrobenzyl sulfonate.

Further, use can be made of compounds obtained by introducing any of the above groups or compounds that when exposed to actinic rays or radiation, generate an acid in a polymer principal chain or side chain, for example, compounds described in U.S. Pat. No. 3,849,137, DE 3914407, JP-A's-63-26653, 55-164824, 62-69263, 63-146038, 63-163452, 62-153853, 63-146029, etc.

Furthermore, use can be made of compounds that when exposed to light, generate an acid described in U.S. Pat. No. 3,779,778 and EP 126,712.

As preferred compounds among the acid generators, there can be mentioned those of general formulae (ZI), (ZII) and (ZIII), below.

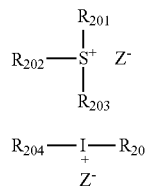

In general formula (ZI), each of $R_{201}$, $R_{202}$ and $R_{203}$ independently represents an organic group.

The number of carbon atoms of the organic group represented by $R_{201}$, $R_{202}$ and $R_{203}$ is generally in the range of 1 to 30, preferably 1 to 20.

Two of $R_{201}$ to $R_{203}$ may be bonded with each other to thereby form a ring structure, and the ring within the same may contain an oxygen atom, a sulfur atom, an ester bond, an amido bond or a carbonyl group. As the group formed by bonding of two of $R_{201}$ to $R_{203}$, there can be mentioned an alkylene group (for example, a butylene group or a pentylene group).

$Z^-$ represents a normucleophilic anion.

As the normucleophilic anion represented by $Z^-$, there can be mentioned, for example, a sulfonate anion, a carboxylate anion, a sulfonylimido anion, a bis(alkylsulfonyl)imido anion, a tris(alkylsulfonyl)methyl anion or the like.

The normucleophilic anion means an anion whose capability of inducing a nucleophilic reaction is extremely low and is an anion capable of inhibiting any temporal decomposition by intramolecular nucleophilic reaction. This would realize an enhancement of the temporal stability of the actinic-ray- or radiation-sensitive resin composition.

As the sulfonate anion, there can be mentioned, for example, an aliphatic sulfonate anion, an aromatic sulfonate anion, a camphor sulfonate anion or the like.

As the carboxylate anion, there can be mentioned, for example, an aliphatic carboxylate anion, an aromatic carboxylate anion, an aralkyl carboxylate anion or the like.

The aliphatic moiety of the aliphatic sulfonate anion may be an alkyl group or a cycloalkyl group, being preferably an alkyl group having 1 to 30 carbon atoms or a cycloalkyl group having 3 to 30 carbon atoms. As such, there can be mentioned, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a boronyl group or the like.

As a preferred aromatic group of the aromatic sulfonate anion, there can be mentioned an aryl group having 6 to 14 carbon atoms, for example, a phenyl group, a tolyl group, a naphthyl group or the like.

The alkyl group, cycloalkyl group and aryl group of the aliphatic sulfonate anion and aromatic sulfonate anion may have a substituent. As the substituent of the alkyl group, cycloalkyl group and aryl group of the aliphatic sulfonate anion and aromatic sulfonate anion, there can be mentioned, for example, a nitro group, a halogen atom (fluorine atom, chlorine atom, bromine atom or iodine atom), a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) or the like. The aryl group or ring structure of these groups may further have an alkyl group (preferably having 1 to 15 carbon atoms) as its substituent.

As the aliphatic moiety of the aliphatic carboxylate anion, there can be mentioned the same alkyl groups and cycloalkyl groups as mentioned with respect to the aliphatic sulfonate anion.

As the aromatic group of the aromatic carboxylate anion, there can be mentioned the same aryl groups as mentioned with respect to the aromatic sulfonate anion.

As a preferred aralkyl group of the aralkyl carboxylate anion, there can be mentioned an aralkyl group having 6 to 12 carbon atoms, for example, a benzyl group, a phenethyl group, a naphthylmethyl group, a naphthylethyl group, a naphthylbutyl group or the like.

The alkyl group, cycloalkyl group, aryl group and aralkyl group of the aliphatic carboxylate anion, aromatic carboxylate anion and aralkyl carboxylate anion may have a substituent. As the substituent of the alkyl group, cycloalkyl group, aryl group and aralkyl group of the aliphatic carboxylate anion, aromatic carboxylate anion and aralkyl carboxylate anion, there can be mentioned, for example, the same halogen atom, alkyl group, cycloalkyl group, alkoxy group, alkylthio group, etc. as mentioned with respect to the aromatic sulfonate anion.

As the sulfonylimido anion, there can be mentioned, for example, a saccharin anion.

The alkyl group of the bis(alkylsulfonyl)imido anion and tris(alkylsulfonyl)methyl anion is preferably an alkyl group having 1 to 5 carbon atoms. As such, there can be mentioned, for example, a methyl group, an ethyl group, a propyl group, an isopropyl group, an n-butyl group, an isobutyl group, a sec-butyl group, a pentyl group, a neopentyl group or the like. As a substituent of these alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group or the like. An alkyl group substituted with a fluorine atom is preferred.

As the other normucleophilic anions, there can be mentioned, for example, phosphorus fluoride, boron fluoride, antimony fluoride and the like.

The normucleophilic anion represented by $Z^-$ is preferably selected from among an aliphatic sulfonate anion substituted at its α-position of sulfonic acid with a fluorine atom, an aromatic sulfonate anion substituted with a fluorine atom or a group having a fluorine atom, a bis(alkylsulfonyl)imido anion whose alkyl group is substituted with a fluorine atom and a tris(alkylsulfonyl)methide anion whose alkyl group is substituted with a fluorine atom. More preferably, the normucleophilic anion is a perfluorinated aliphatic sulfonate anion having 4 to 8 carbon atoms or a benzene sulfonate anion having a fluorine atom. Still more preferably, the normucleophilic anion is a nonafluorobutane sulfonate anion, a perfluorooctane sulfonate anion, a pentafluorobenzene sulfonate anion or a 3,5-bis(trifluoromethyl)benzene sulfonate anion.

As normucleophilic anion represented by $Z^-$, there can also be mentioned those having the structures of general formula (Xa) or (Xb) below.

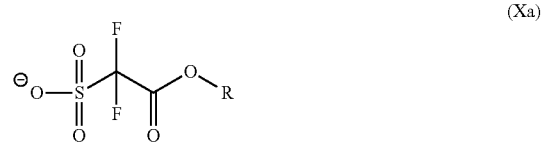
(Xa)

In general formula (Xa), R represents a hydrogen atom or an organic group. R is preferably an organic group having 1 to 40 carbon atoms, more preferably an organic group having 3 to 20 carbon atoms and most preferably any of the organic groups of formula (XI) below.

The organic group represented by R essentially has one or more carbon atoms. Preferably, the atom bonded to the oxygen atom of the ester bond appearing in general formula (Xa) is a carbon atom. As the organic groups, there can be mentioned, for example, an alkyl group, a cycloalkyl group, an aryl group, an aralkyl group and a group with a lactone structure. These groups in the chain thereof may have a heteroatom, such as an oxygen atom or a sulfur atom. These groups may be introduced in each other as substituents, and they may further have a substituent, such as a hydroxyl group, an acyl group, an acyloxy group, an oxy group (=O) or a halogen atom.

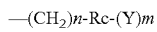
Formula (XI)

In general formula (XI), Rc represents a single bond, an oxygen atom, a carbonyl group, a sulfur atom, —SO—, —SO$_2$—, —NH—, an alkylene group having 1 to 10 carbon atoms, a cycloalkylene group having 3 to 15 carbon atoms, a mono- or polycyclic organic group having 3 to 30 carbon atoms that may contain a cyclic ether, cyclic thioether, cyclic ketone, cyclic carbonic ester, lactone or lactam structure, or a bivalent connecting group composed of a combination of these. Y represents a hydroxyl group, a halogen atom, a cyano group, a carboxyl group, a hydrocarbon group having 1 to 10 carbon atoms, a mono- or polycyclic organic group having 3 to 30 carbon atoms, a hydroxyalkyl group having 1 to 10 carbon atoms, an alkoxy group having 1 to 10 carbon atoms, an acyl group having 1 to 10 carbon atoms, an alkoxycarbonyl group having 2 to 10 carbon atoms, an acyloxy group having 2 to 10 carbon atoms, an alkoxyalkyl group having 2 to 10 carbon atoms, or a halogenated alkyl group having 1 to 8 carbon atoms. In the formula, m is 0 to 6. In the instance of multiple Ys, they may be identical to or different from each other. Further, n is 0 to 10. Rc is preferably a single bond, an oxygen atom, a carbonyl group, a hydrocarbon group having 1 to 10 carbon atoms or a bivalent connecting group composed of a combination of these, more preferably a single bond. Y is preferably a mono- or polycyclic organic group having 3 to 30 carbon atoms, more preferably a polycyclic organic group such as an adamantane structure or a norbornane structure.

The sum of carbon atoms constructing each of the R-groups of the formula (XI) is preferably 40 or less.

Preferably, n is 0 to 3, and it is preferred for Rc to be a monocyclic or polycyclic organic group having 7 to 16 carbon atoms.

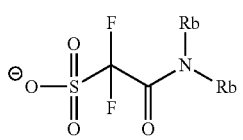

In general formula (Xb), Rb represents a hydrogen atom or an organic group. Preferably, Rb represents a hydrogen atom or an organic group having 1 to 40 carbon atoms. More preferably, Rb represents a hydrogen atom or an organic group having 3 to 20 carbon atoms. Rbs may be different from each other, and may be bonded to each other to thereby form a ring. The organic group represented by Rb essentially has one or more carbon atoms. Preferably, the atom bonded to the nitrogen atom of the amido bond appearing in general formula (Xb) is a carbon atom. As the organic groups, there can be mentioned, for example, an alkyl group, a cycloalkyl group, an aryl group, an aralkyl group and a group with a lactone structure. The organic groups in the chain thereof may have a heteroatom, such as an oxygen atom or a sulfur atom. These groups may be introduced in each other as substituents, and they may further have a substituent, such as a hydroxyl group, an acyl group, an acyloxy group, an oxy group (=O) or a halogen atom.

The molecular weight of each of the normucleophilic anion moieties of general formulae (Xa) and (Xb) is generally in the range of 300 to 1000, preferably 400 to 800 and more preferably 500 to 700.

Each of the normucleophilic anion moieties of general formulae (Xa) and (Xb) is also appropriate for the counter anion X⁻ of general formula (I).

As the organic groups represented by $R_{201}$, $R_{202}$ and $R_{203}$, there can be mentioned, for example, groups corresponding to the following compounds (ZI-1), (ZI-2) and (ZI-3).

Appropriate use may be made of compounds with two or more of the structures of the general formula (ZI). For example, use may be made of compounds having a structure wherein at least one of $R_{201}$ to $R_{203}$ of a compound of the general formula (ZI) is bonded with at least one of $R_{201}$ to $R_{203}$ of another compound of the general formula (ZI).

As preferred (ZI) components, there can be mentioned the following compounds (ZI-1), (ZI-2) and (ZI-3).

The compounds (ZI-1) are arylsulfonium compounds of the general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group or a cycloalkyl group.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by $R_{201}$ to $R_{203}$ may have as its substituent an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 4 carbon atoms and an alkoxy group having 1 to 4 carbon atoms. The substituents may be contained in any one of the three $R_{201}$ to $R_{203}$, or alternatively may be contained in all three of $R_{201}$ to $R_{203}$. When $R_{201}$ to $R_{203}$ represent an aryl group, the substituent preferably lies at the p-position of the aryl group.

Now, the compounds (ZI-2) will be described.

The compounds (ZI-2) are compounds of the formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group). As more preferred alkyl groups, there can be mentioned a 2-oxoalkyl group and an alkoxycarbonylmethyl group. As more preferred cycloalkyl group, there can be mentioned a 2-oxocycloalkyl group.

The 2-oxoalkyl group may be linear or branched. A group having >C=O at the 2-position of the alkyl group is preferred.

The 2-oxocycloalkyl group is preferably a group having >C=O at the 2-position of the cycloalkyl group.

As preferred alkoxy groups of the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group or a nitro group.

The compounds (ZI-3) are those represented by the following general formula (ZI-3) which have a phenacylsulfonium salt structure.

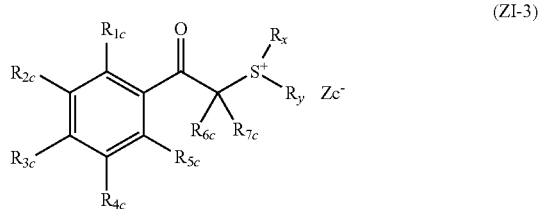

(ZI-3)

In general formula (ZI-3), each of $R_{1c}$ to $R_{5c}$ independently represents a hydrogen atom, an alkyl group, a cycloalkyl group, an alkoxy group, a halogen atom or a phenylthio group.

Each of $R_{6c}$ and $R_{7c}$ independently represents a hydrogen atom, an alkyl group, a cycloalkyl group, halogen atom, a cyano group or an aryl group.

Each of $R_x$ and $R_y$ independently represents an alkyl group, a cycloalkyl group, a 2-oxoalkyl group, a 2-oxocycloalkyl group, an alkoxycarbonylalkyl group, an allyl group or a vinyl group.

Any two or more of $R_{1c}$ to $R_{5c}$, and $R_{6c}$ and $R_{7c}$, and $R_x$ and $R_y$, may be bonded with each other to thereby form a ring structure. This ring structure may contain an oxygen atom, a sulfur atom, an ester bond or an amido bond. As the group formed by bonding of any two or more of $R_{1c}$ to $R_{5c}$, and $R_{6c}$ and $R_{7c}$, and $R_x$ and $R_y$, there can be mentioned a butylene group, a pentylene group or the like.

$Zc^-$ represents a nonnucleophilic anion. There can be mentioned the same nonnucleophilic anions as mentioned with respect to the $Z^-$ of the general formula (ZI).

The alkyl group represented by $R_{1c}$ to $R_{7c}$ may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group). As the cycloalkyl group, there can be mentioned, for example, a cycloalkyl group having 3 to 8 carbon atoms (for example, a cyclopentyl group or a cyclohexyl group).

The alkoxy group represented by $R_{1c}$ to $R_{5c}$ may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group or a linear or branched pentoxy group) and a cycloalkoxy group having 3 to 8 carbon atoms (for example, a cyclopentyloxy group or a cyclohexyloxy group).

Preferably, any one of $R_{1c}$ to $R_{5c}$ is a linear or branched alkyl group, a cycloalkyl group or a linear, branched or cyclic alkoxy group. More preferably, the sum of carbon atoms of $R_{1c}$ to $R_{5c}$ is in the range of 2 to 15. Accordingly, there can be attained an enhancement of solvent solubility and inhibition of particle generation during storage.

Each of the aryl groups represented by $R_{6c}$ and $R_{1c}$ preferably has 5 to 15 carbon atoms. As such, there can be mentioned, for example, a phenyl group or a naphthyl group.

When $R_{6c}$ and $R_{7c}$ are bonded to each other to thereby form a ring, the group formed by the bonding of $R_{6c}$ and $R_{7c}$ is preferably an alkylene group having 2 to 10 carbon atoms. As such, there can be mentioned, for example, an ethylene group, a propylene group, a butylene group, a pentylene group, a hexylene group or the like. Further, the ring formed by the bonding of $R_{6c}$ and $R_{7c}$ may have a heteroatom, such as an oxygen atom, in the ring.

As the alkyl groups and cycloalkyl groups represented by $R_x$ and $R_y$, there can be mentioned the same alkyl groups and cycloalkyl groups as set forth above with respect to $R_{1c}$ to $R_{7c}$.

As the 2-oxoalkyl group and 2-oxocycloalkyl group, there can be mentioned the alkyl group and cycloalkyl group represented by $R_{1c}$ to $R_{7c}$ having >C=O at the 2-position thereof.

With respect to the alkoxy group of the alkoxycarbonylalkyl group, there can be mentioned the same alkoxy groups as mentioned above with respect to $R_{1c}$ to $R_{5c}$. As the alkyl group thereof, there can be mentioned, for example, an alkyl group having 1 to 12 carbon atoms, preferably a linear alkyl group having 1 to 5 carbon atoms (e.g., a methyl group or an ethyl group).

The allyl groups are not particularly limited. However, preferred use is made of an unsubstituted allyl group or an allyl group substituted with a cycloalkyl group of a single ring or multiple rings.

The vinyl groups are not particularly limited. However, preferred use is made of an unsubstituted vinyl group or a vinyl group substituted with a cycloalkyl group of a single ring or multiple rings.

As the ring structure that may be formed by the mutual bonding of $R_x$ and $R_y$, there can be mentioned a 5-membered or 6-membered ring, especially preferably a 5-membered ring (namely, a tetrahydrothiophene ring), formed by bivalent $R_x$ and $R_y$ (for example, a methylene group, an ethylene group, a propylene group or the like) in cooperation with the sulfur atom of general formula (ZI-3).

Each of $R_x$ and $R_y$ is preferably an alkyl group or cycloalkyl group having preferably 4 or more carbon atoms. The alkyl group or cycloalkyl group has more preferably 6 or more carbon atoms and still more preferably 8 or more carbon atoms.

In the general formulae (ZII) and (ZIII), each of $R_{204}$ to $R_{207}$ independently represents an aryl group, an alkyl group or a cycloalkyl group.

The aryl group represented by $R_{204}$ to $R_{207}$ is preferably a phenyl group or a naphthyl group, more preferably a phenyl group. The aryl group represented by $R_{204}$ to $R_{207}$ may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like.

As preferred alkyl groups and cycloalkyl groups represented by $R_{204}$ to $R_{207}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group).

The aryl group, alkyl group and cycloalkyl group represented by $R_{204}$ to $R_{207}$ may have a substituent. As a possible substituent on the aryl group, alkyl group and cycloalkyl group represented by $R_{204}$ to $R_{207}$, there can be mentioned, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, hydroxyl group, a phenylthio group or the like.

$Z^-$ represents a normucleophilic anion. As such, there can be mentioned the same normucleophilic anions as mentioned with respect to the $Z^-$ of the general formula (ZI).

As the acid generators, there can be further mentioned the compounds of the following general formulae (ZIV), (ZV) and (ZVI).

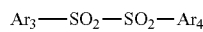

ZIV

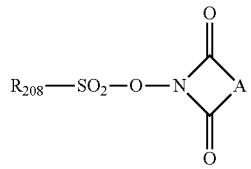

ZV

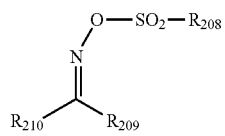

ZVI

In the general formulae (ZIV) to (ZVI), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Among the acid generators, the compounds of the general formulae (ZI) to (ZIII) are more preferred.

As a preferred acid generator, there can be mentioned a compound that generates an acid having one sulfonate group or imido group. As a more preferred acid generator, there can be mentioned a compound that generates a monovalent perfluoroalkanesulfonic acid, a compound that generates a monovalent aromatic sulfonic acid substituted with a fluorine atom or fluorine-atom-containing group, or a compound that generates a monovalent imidic acid substituted with a fluorine atom or fluorine-atom-containing group. As a still more preferred acid generator, there can be mentioned any of sulfonium salts of fluorinated alkanesulfonic acid, fluorinated benzenesulfonic acid, fluorinated imidic acid and fluorinated methide acid. With respect to practicable acid generators, it is especially preferred for the generated acid to be a fluorinated alkanesulfonic acid, fluorinated benzenesulfonic acid or fluorinated imidic acid of −1 or below pKa. By the use thereof, an enhancement of sensitivity can be attained.

Especially preferred examples of the acid generators are as follows.

(z1)

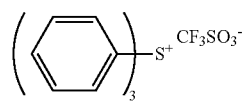

(z2)

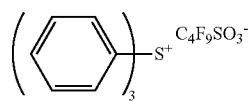

(z3)

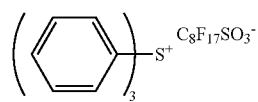

(z4)

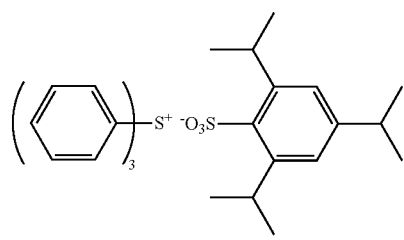

(z5)

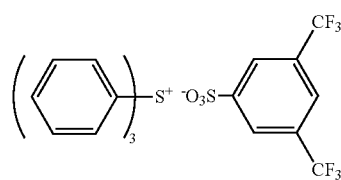

(z6)

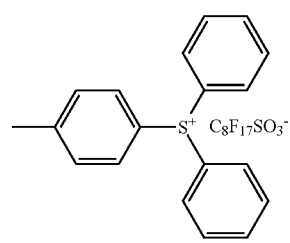

(z7)

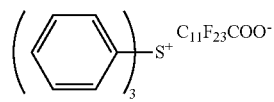

(z8)

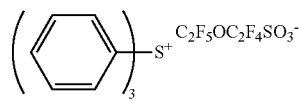

-continued
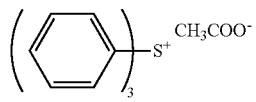
(z9)
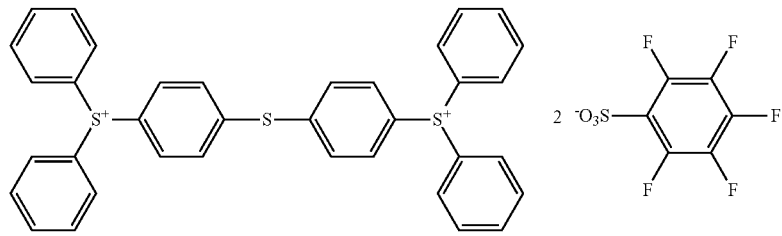
(z10)
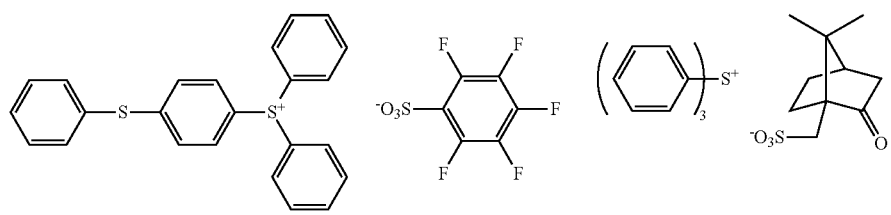
(z11) (z12)
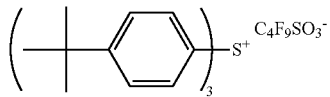
(z13)
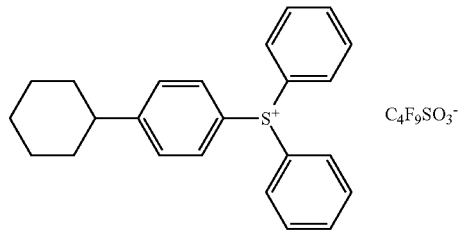
(z14)
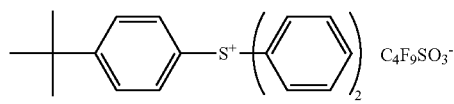
(z15)
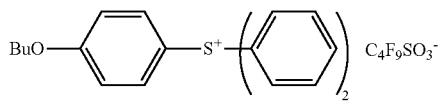
(z16)
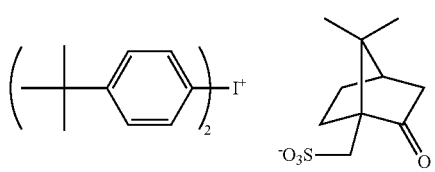
(z17)
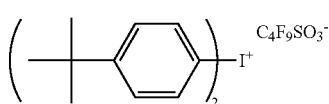
(z18)
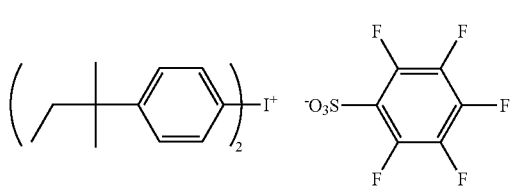
(z19)
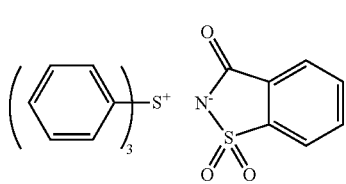
(z20)
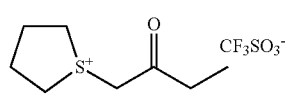
(z21)
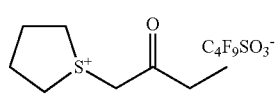
(z22)
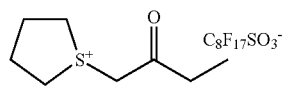
(z23)
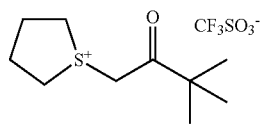
(z24)

-continued
(z25) 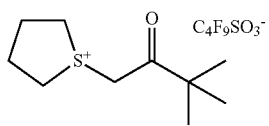
(z26) 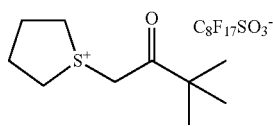
(z27)
(z28) 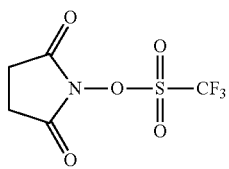
(z29)
(z30) 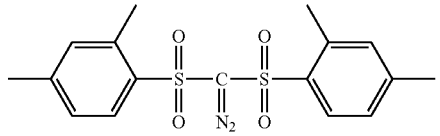
(z31)
(z32) 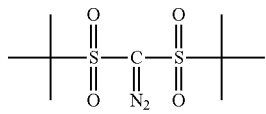
(z33) 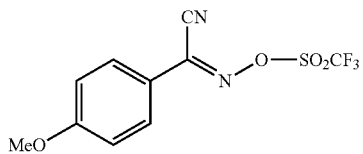
(z34) 
(z35)
(z36) 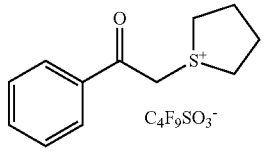
(z37)
(z38) 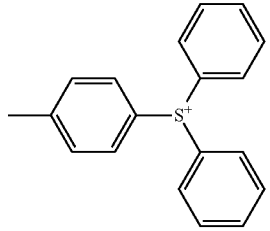
(z39)
(z40) 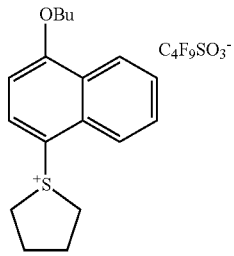

-continued
(z41) 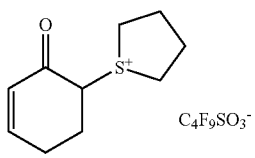
(z42) 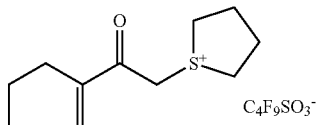
(z43) 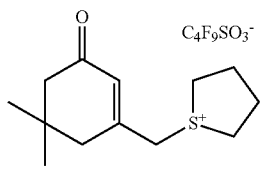
(z44) 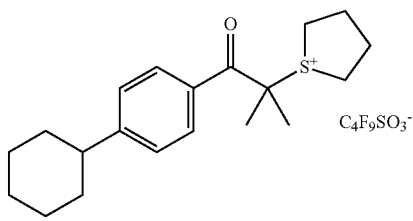
(z45) 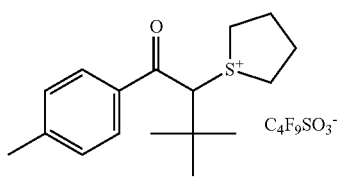
(z46) 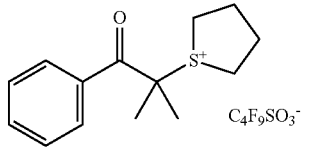
(z47) 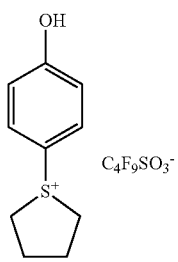
(z48) 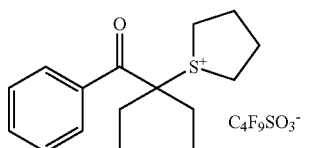
(z49) 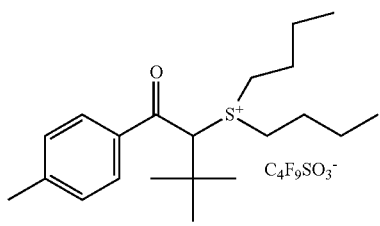
(z50) 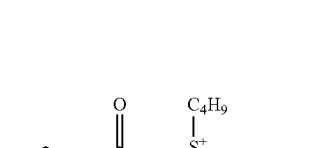
(z51) 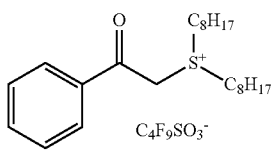
(z52) 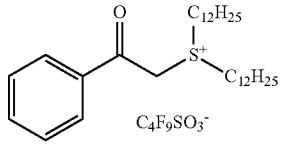
(z53) 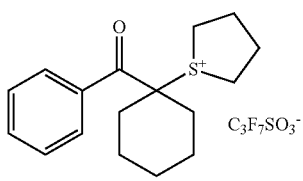
(z54) 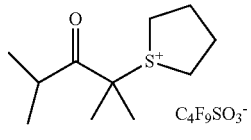
(z55) 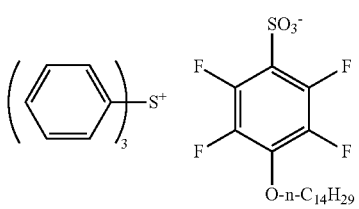
(z56) 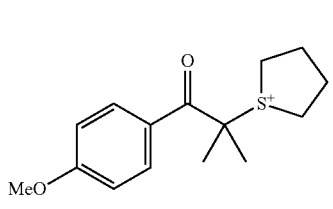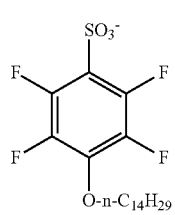

-continued
(z57) 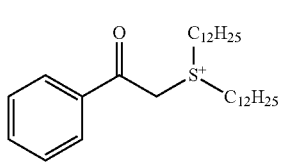 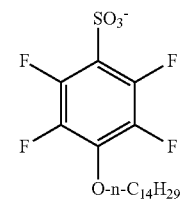
(z58) 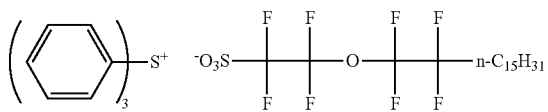
(z59) 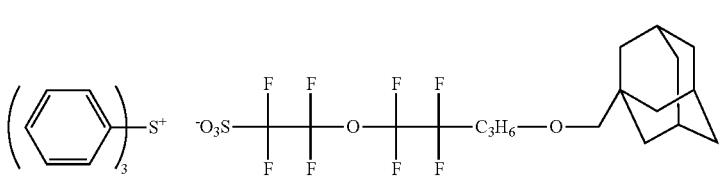
(z60) 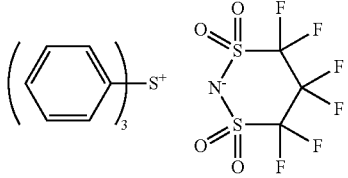
(z61) 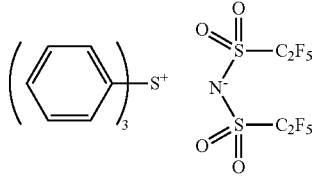
(z62) 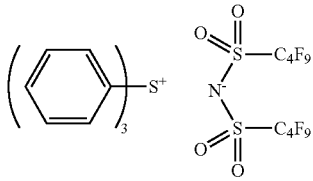
(z63) 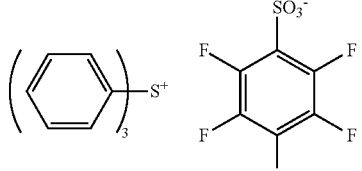
(z64) 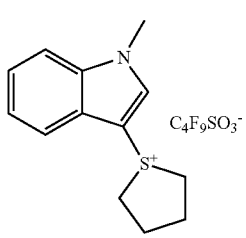
(z65) 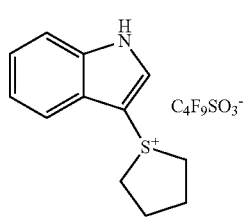
(z66) 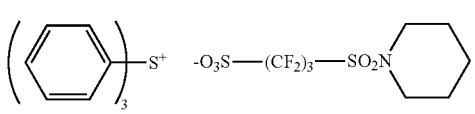
(z67) 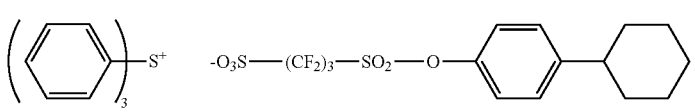
(z68) 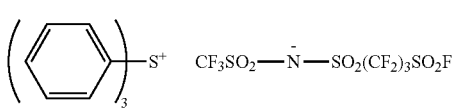
(z69) 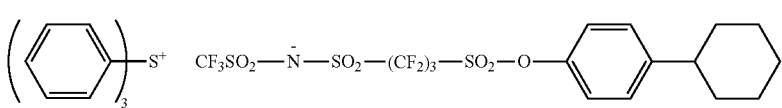
(z70)

-continued
(z71) 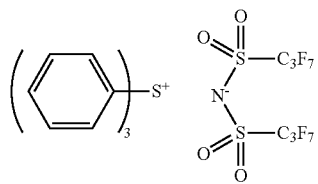
(z72) 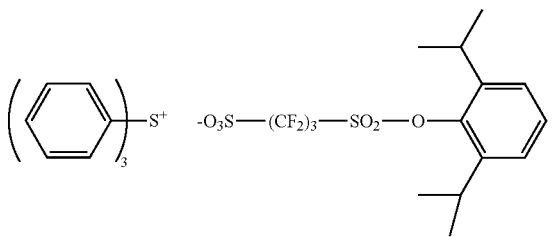
(z73) 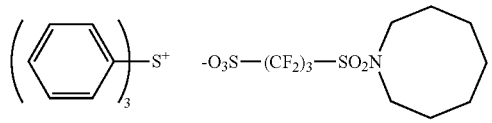
(z74) 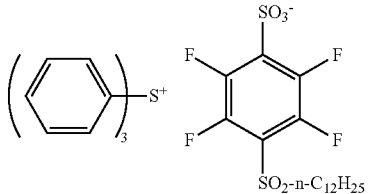
(z75) 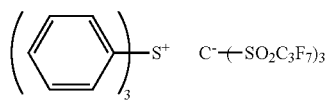
(z76) 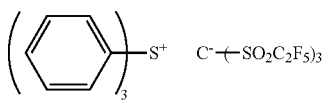
(z77) 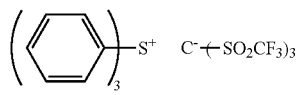
(z78) 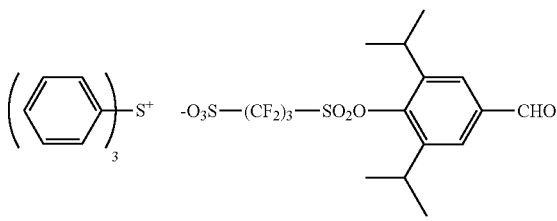
(z79) 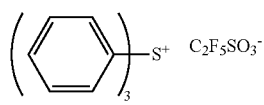
(z80) 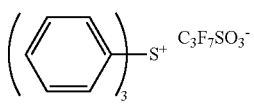
(z81) 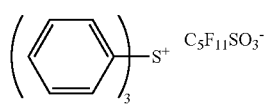
(z82) 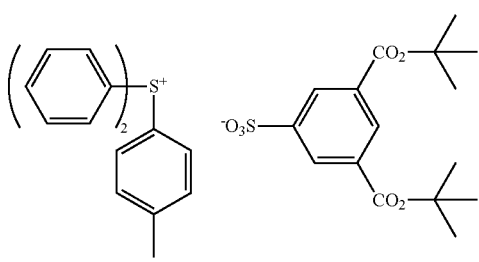
(z83) 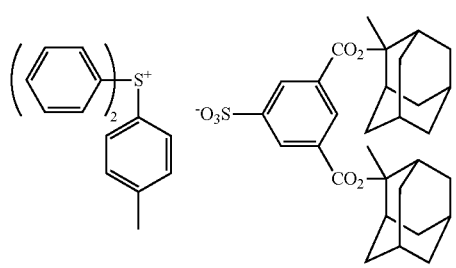
(z84) 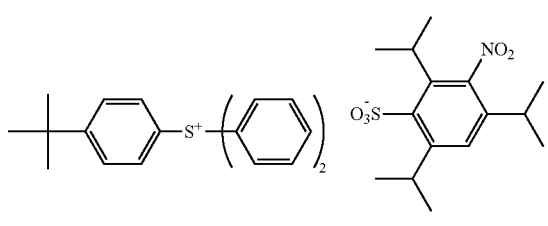

-continued
(z85) 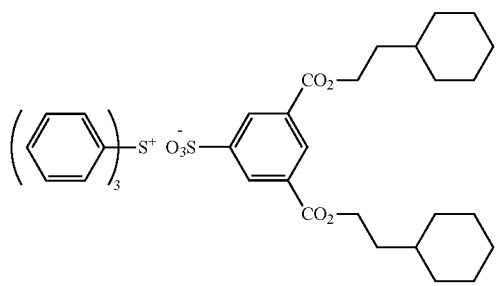
(z86) 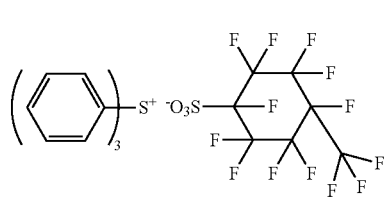
(z87) 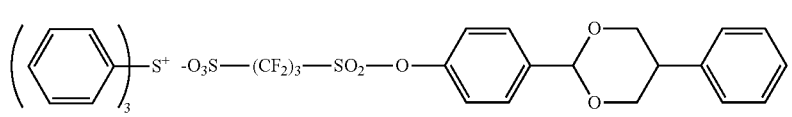
(z88) 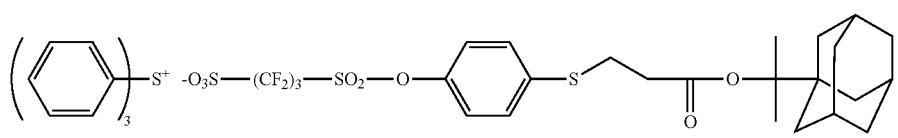
(z89) 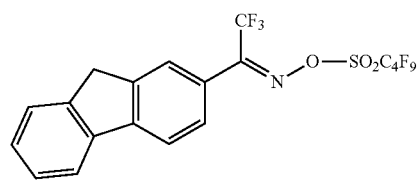
(z90) 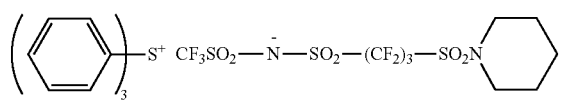
(z91) 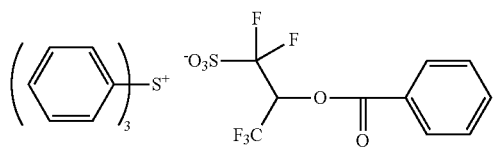
(Y-1) 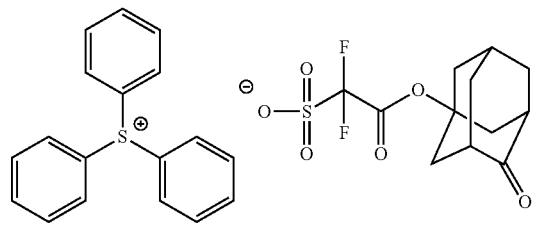
(Y-2) 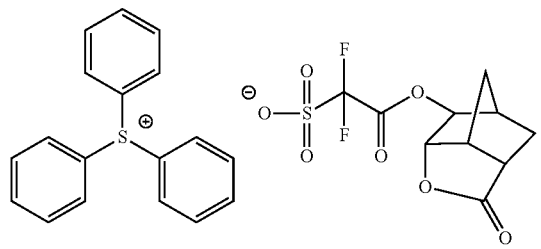
(Y-3) 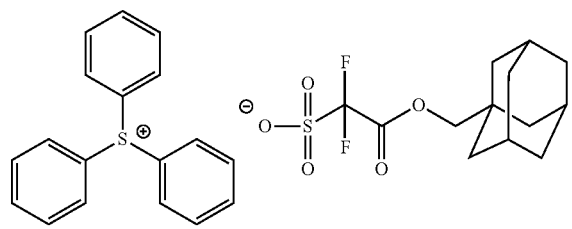
(Y-4) 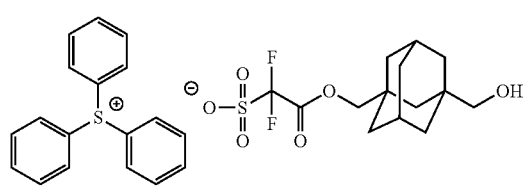
(Y-5) 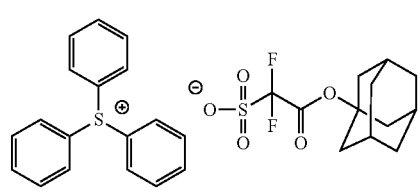

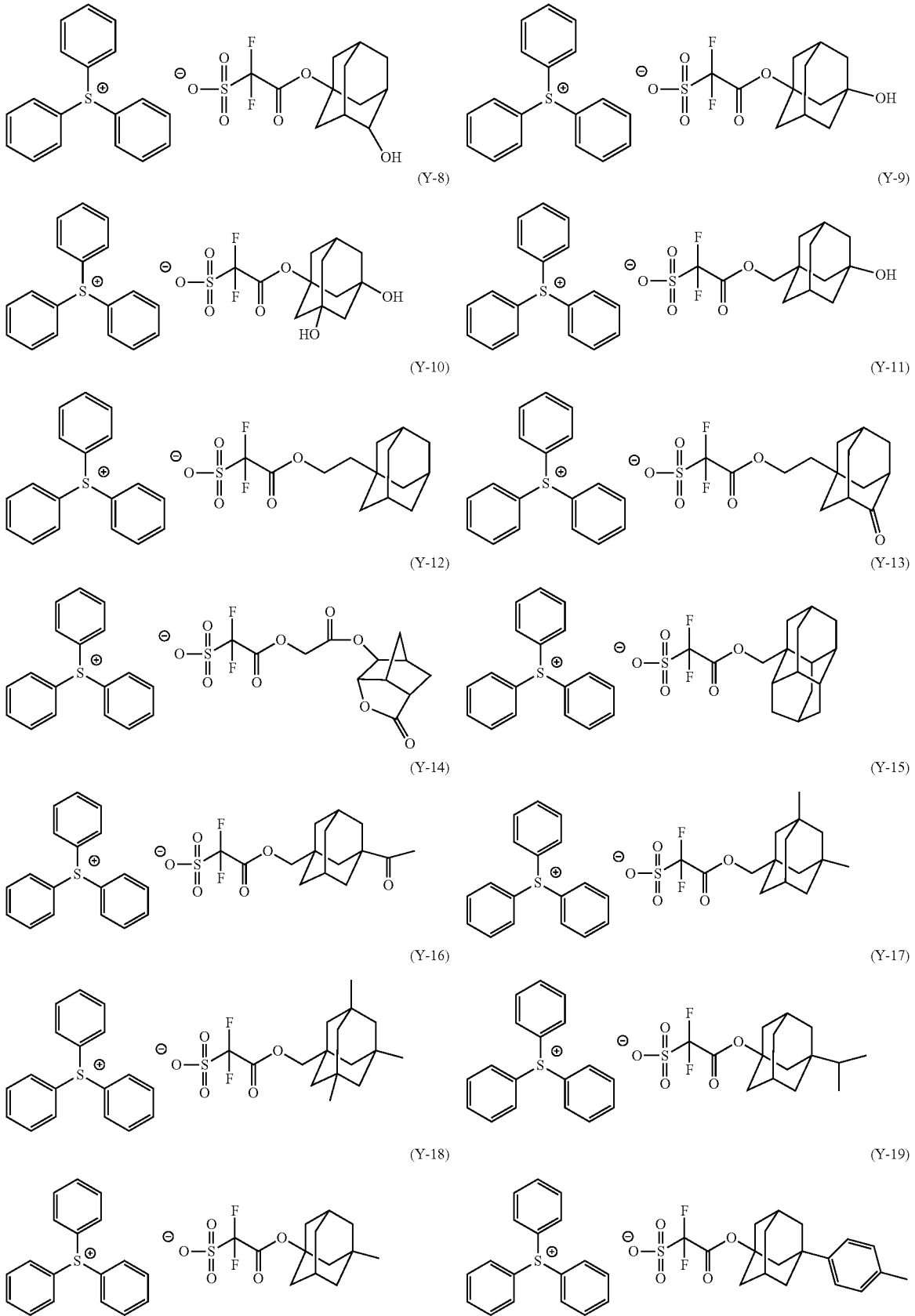

-continued
(Y-20)
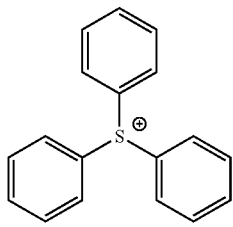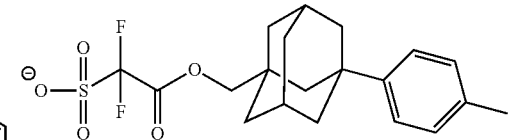
(Y-21)
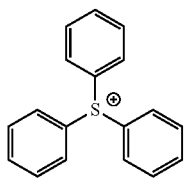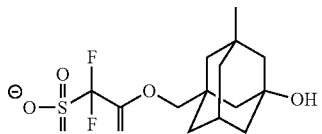
(Y-22)
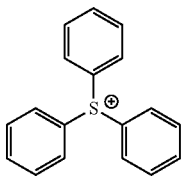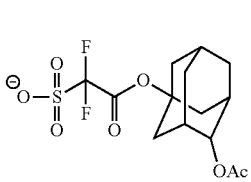
(Y-23)
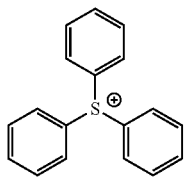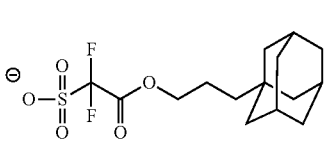
(Y-24)
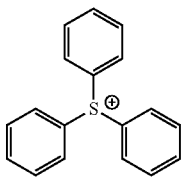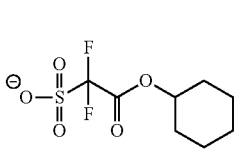
(Y-25)
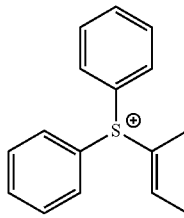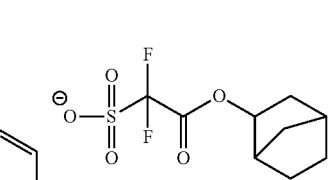
(Y-26)
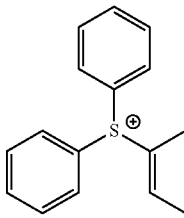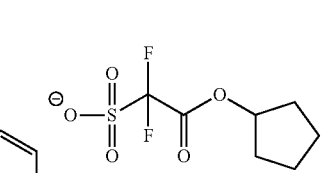
(Y-27)
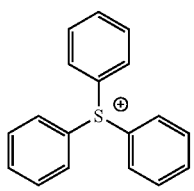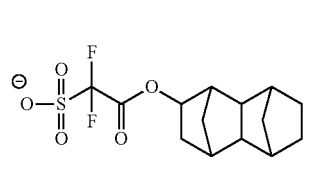
(Y-28)
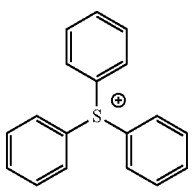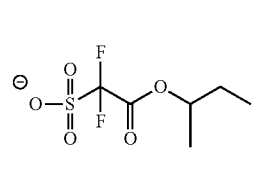
(Y-29)
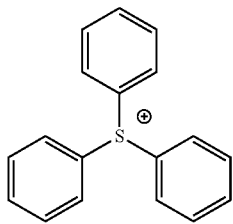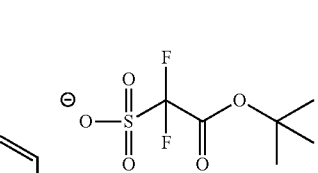
(Y-30)
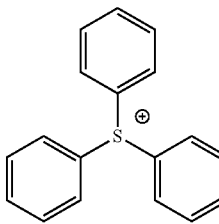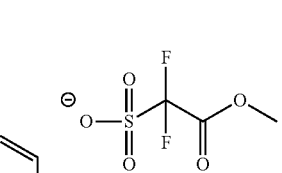
(Y-31)
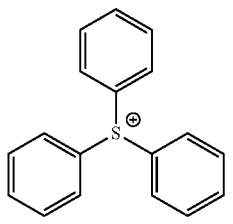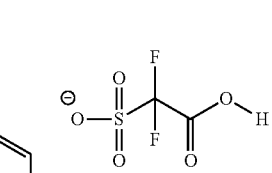
(Y-32)
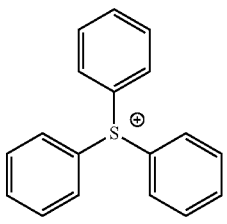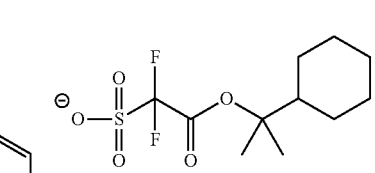

-continued (Y-33) (Y-34) (Y-35) (Y-36) (Y-37) (Y-38) (Y-39) (Y-40) (Y-41) (Y-42) (Y-43) (Y-44) (Y-45)

-continued
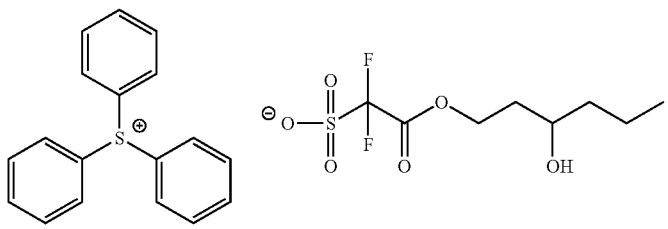
(Y-46)
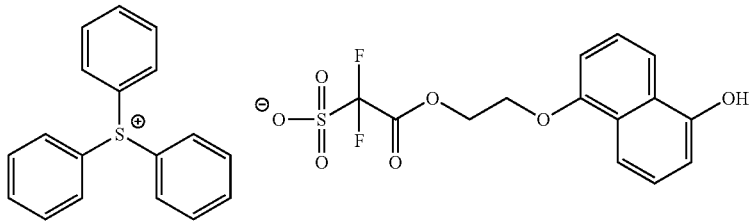
(Y-47)
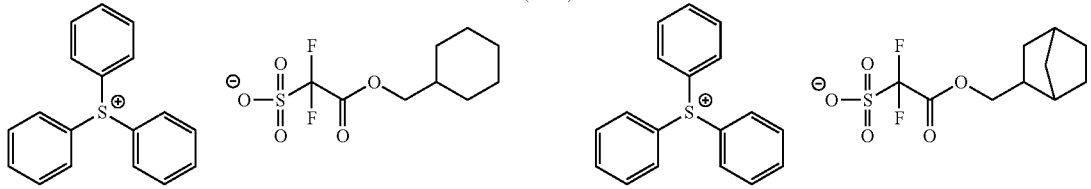
(Y-48)            (Y-49)
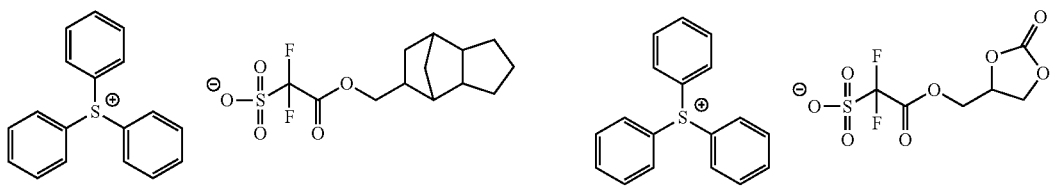
(Y-50)            (Y-51)
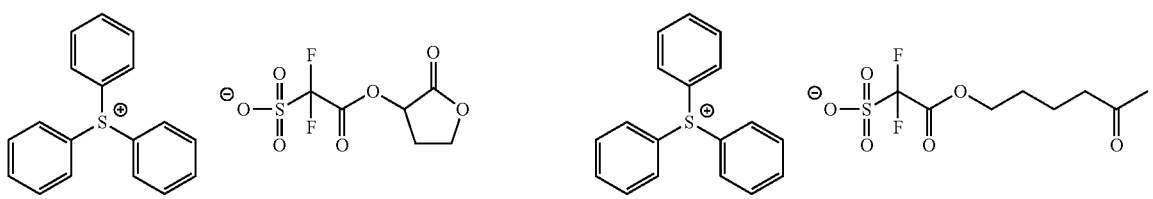
(Y-52)            (Y-53)
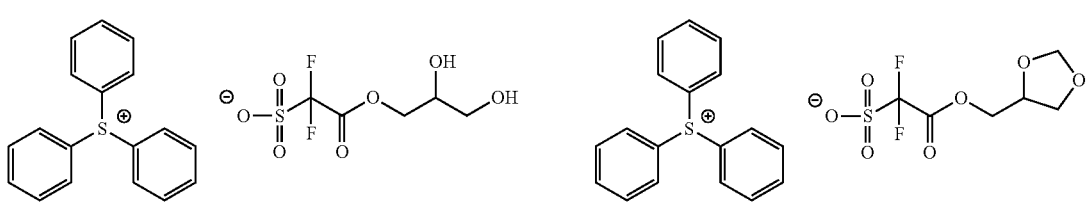
(Y-54)            (Y-55)
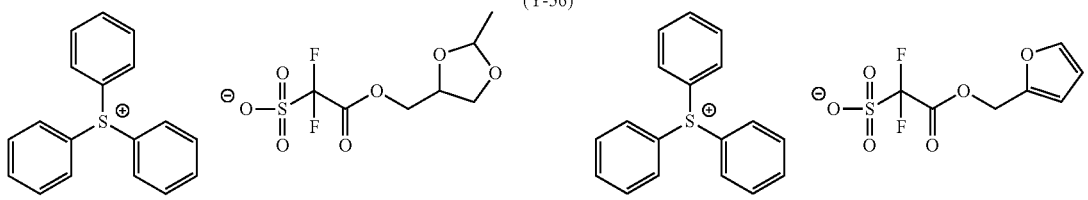
(Y-56)            (Y-57)

-continued
| | |
|---|---|
| (Y-58) 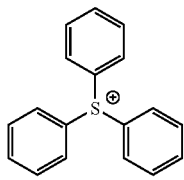 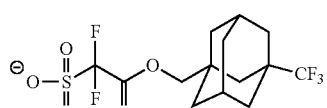 | (Y-59) 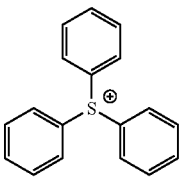 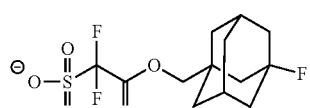 |
| (Y-60) 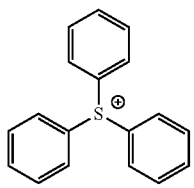 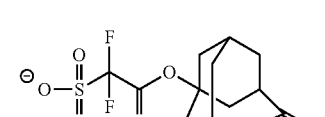 | (Y-61) 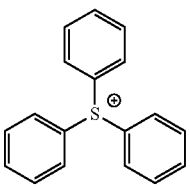 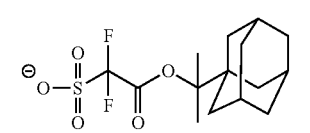 |
| (Y-62) 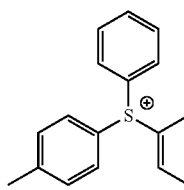 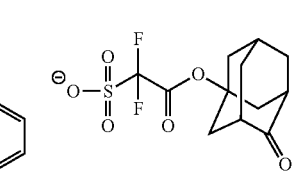 | (Y-63) 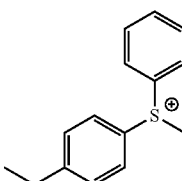 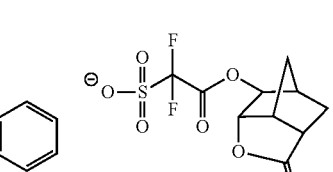 |
| (Y-64) 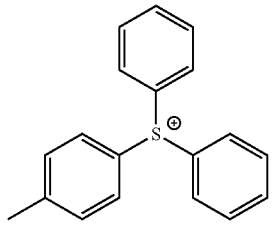 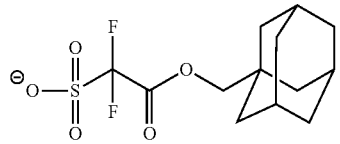 | |
| (Y-65) 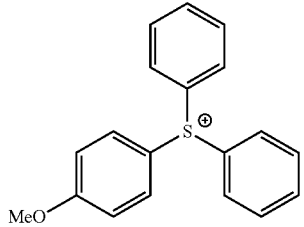 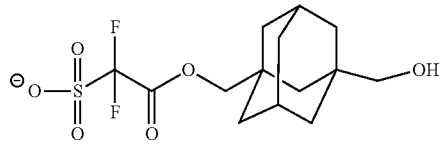 | |
| (Y-66) 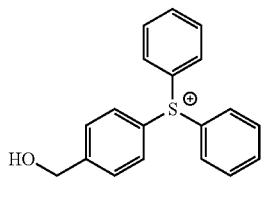 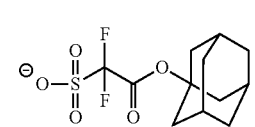 | (Y-67) 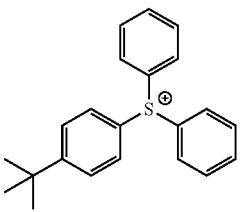 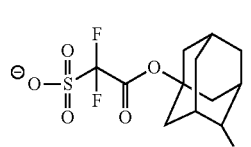 |
| (Y-68) 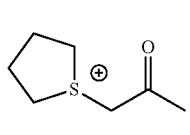 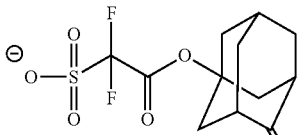 | (Y-69) 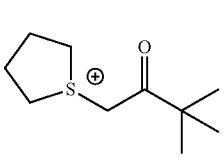 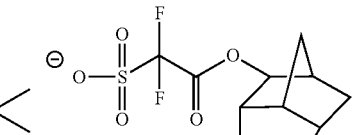 |

-continued
(Y-70)
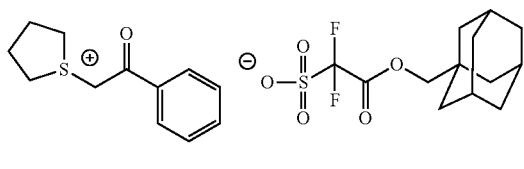
(Y-71)
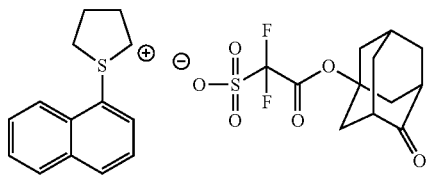
(Y-72)
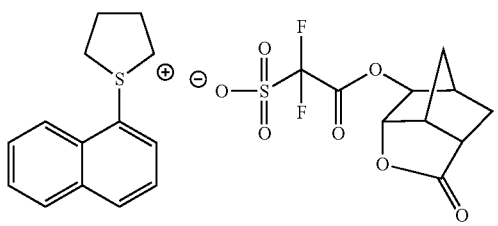
(Y-73)
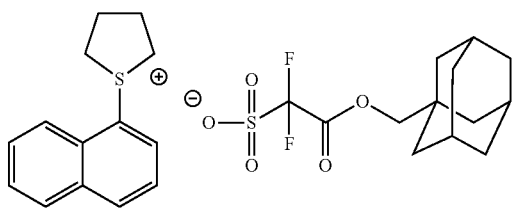
(Y-74)
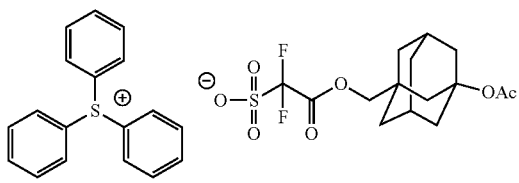
(Y-75)
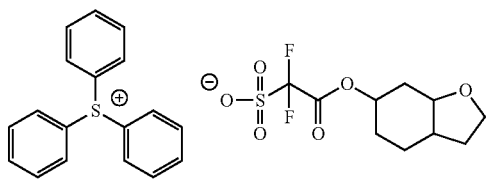
(Y-76)
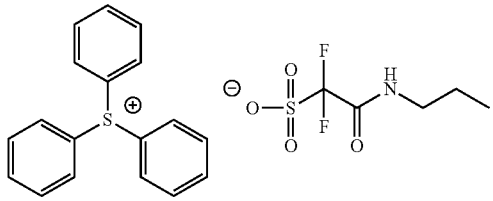
(Y-77)
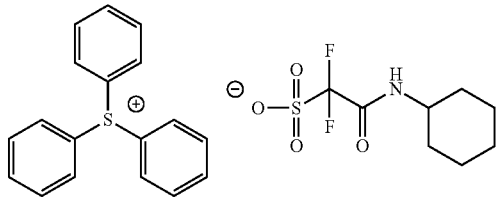
(Y-78)
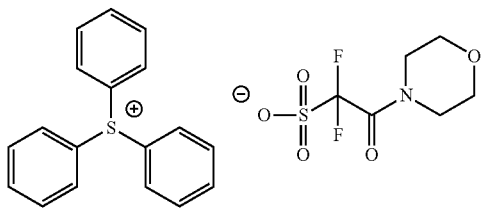
(Y-79)
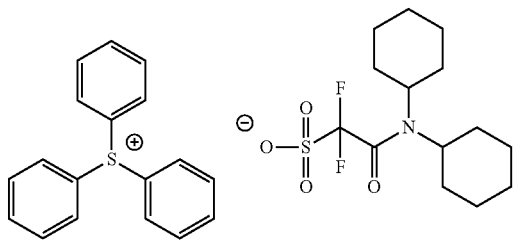
(Y-80)
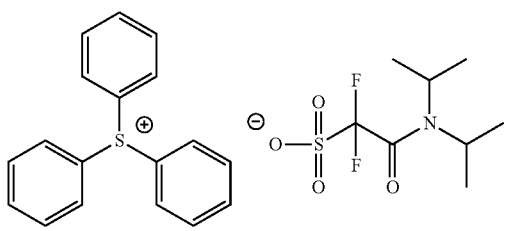
(Y-81)
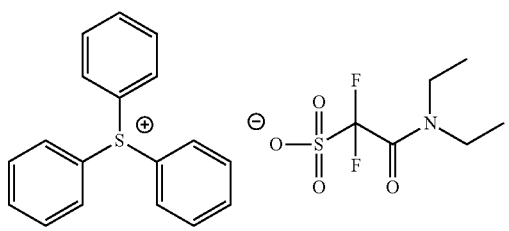

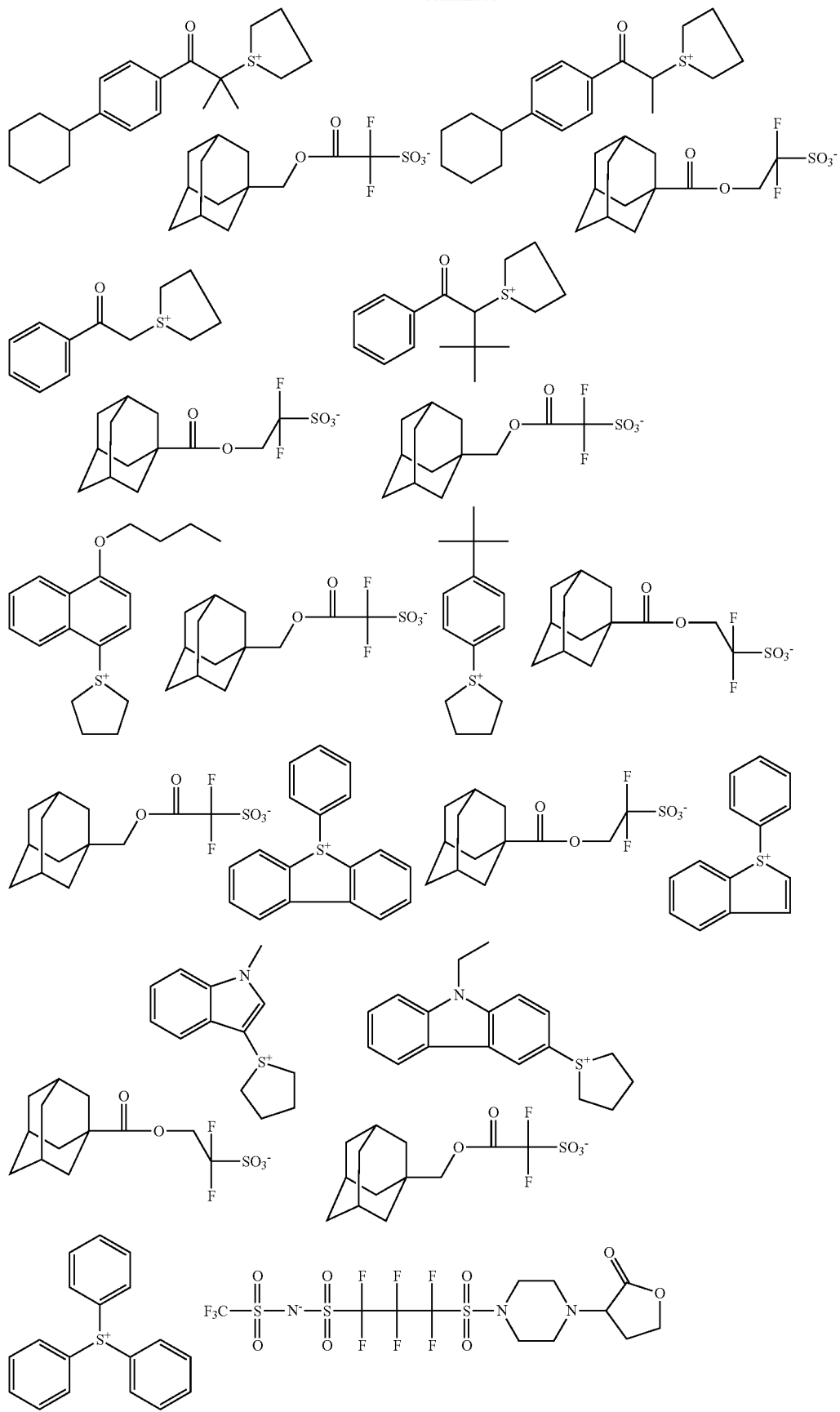

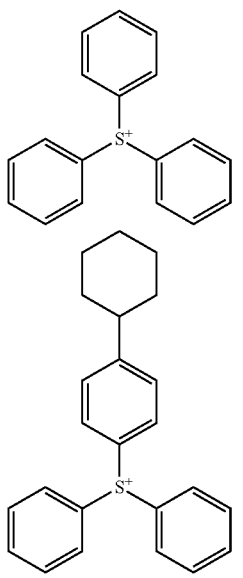
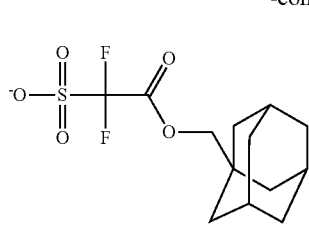
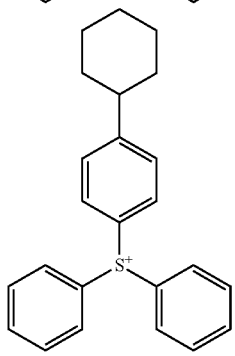
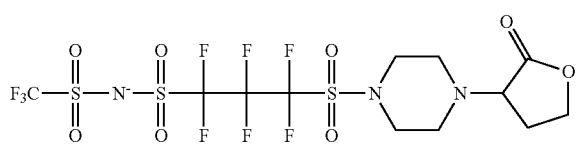

(B) Resin whose rate of dissolution into an alkali developer is increased by the action of an acid The actinic-ray- or radiation-sensitive resin composition of the present invention contains a resin (B) whose solubility in an alkali developer is increased by the action of an acid.

The resin whose solubility in an alkali developer is increased by the action of an acid (acid-decomposable resin) contains a group that is decomposed by the action of an acid to thereby produce an alkali-soluble group (hereinafter also referred to as "acid-decomposable group") in the principal chain or side chain, or both the principal chain and the side chain, of the resin.

The resin (B) is preferably insoluble or poorly soluble in alkali developers.

The acid-decomposable group is preferably a group as obtained by protecting the alkali soluble group with a protective group that is decomposed by the action of an acid, and eliminated.

As the alkali soluble group, there can be mentioned a phenolic hydroxyl group, a carboxyl group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali soluble groups, there can be mentioned a carboxyl group, a fluoroalcohol group (preferably hexafluoroisopropanol) and a sulfonate group.

The acid-decomposable group is preferably a group as obtained by substituting the hydrogen atom of any of these alkali soluble groups with an acid eliminable group.

As the acid eliminable group, there can be mentioned, for example, —C($R_{36}$)($R_{37}$)($R_{38}$), —C($R_{36}$)($R_{37}$)(O$R_{39}$), —C($R_{01}$)($R_{02}$)(O$R_{39}$) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ to $R_{02}$ independently represents a hydrogen atom, an alkyl group, a cycloalkyl group, an aryl group, an aralkyl group or an alkenyl group.

Preferably, the acid-decomposable group is a cumyl ester group, an enol ester group, an acetal ester group, a tertiary alkyl ester group or the like. A tertiary alkyl ester group is more preferred.

The repeating unit with an acid-decomposable group that may be contained in the resin (B) is preferably any of those of the following general formula (AI).

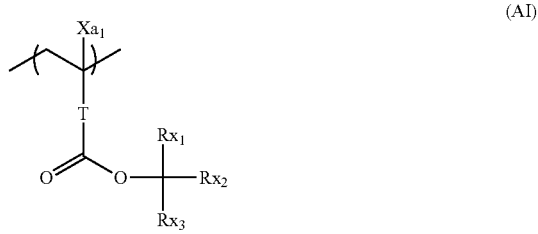

In general formula (AI), $Xa_1$ represents a hydrogen atom, an optionally substituted methyl group or any of the groups of the formula —$CH_2$—$R_9$. $R_9$ represents a hydroxyl group or a monovalent organic group. The monovalent organic group is, for example, an alkyl group having 5 or less carbon atoms or an acyl group. Preferably, the monovalent organic group is an alkyl group having 3 or less carbon atoms, more preferably a methyl group. $Xa_1$ is preferably a hydrogen atom, a methyl group, a trifluoromethyl group or a hydroxymethyl group.

T represents a single bond or a bivalent connecting group.

Each of $Rx_1$ to $Rx_3$ independently represents an alkyl group (linear or branched) or a cycloalkyl group (monocyclic or polycyclic).

At least two of $Rx_1$ to $Rx_3$ may be bonded with each other to thereby form a cycloalkyl group (monocyclic or polycyclic).

As the bivalent connecting group represented by T, there can be mentioned an alkylene group, a group of the formula —COO—Rt—, a group of the formula —O—Rt— or the like. In the formulae, Rt represents an alkylene group or a cycloalkylene group.

T is preferably a single bond or a group of the formula —COO—Rt—. Rt is preferably an alkylene group having 1 to 5 carbon atoms, more preferably a —CH$_2$— group or —(CH$_2$)$_3$— group.

The alkyl group represented by each of Rx$_1$ to Rx$_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of Rx$_1$ to Rx$_3$ is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

The cycloalkyl group formed by bonding of at least two of Rx$_1$ to Rx$_3$ is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

In a preferred mode, Rx$_1$ is a methyl group or an ethyl group, and Rx$_2$ and Rx$_3$ are bonded with each other to thereby form any of the above-mentioned cycloalkyl groups.

Each of the groups, above, may have a substituent. As the substituent, there can be mentioned, for example, an alkyl group (having 1 to 4 carbon atoms), a halogen atom, a hydroxyl group, an alkoxy group (having 1 to 4 carbon atoms), a carboxyl group, an alkoxycarbonyl group (having 2 to 6 carbon atoms) or the like. Substituents having 8 or less carbon atoms are preferred.

The total content ratio of the repeating units with acid-decomposable groups is preferably in the range of 20 to 70 mol %, more preferably 30 to 50 mol %, based on all the repeating units of the resin (B).

Specific examples of the preferred repeating units with acid-decomposable groups will be shown below, which however in no way limit the scope of the present invention.

In the following formulae, each of Rx and Xa$_1$ represents a hydrogen atom, CH$_3$, CF$_3$ or CH$_2$OH. Each of Rxa and Rxb represents an alkyl group having 1 to 4 carbon atoms. Z, each independently in the presence of two or more groups, represents a substituent containing a polar group. p represents 0 or a positive integer.

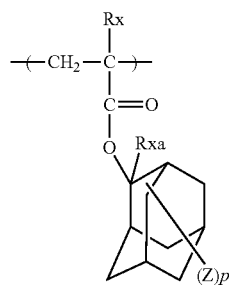

1

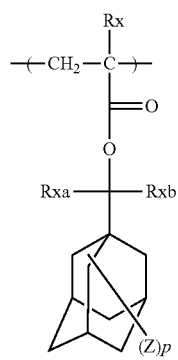

2

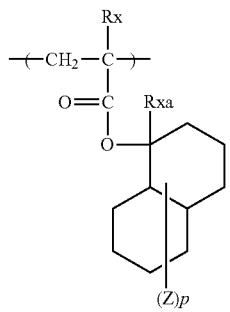

3

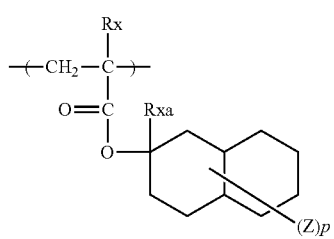

4

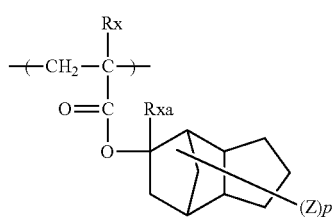

5

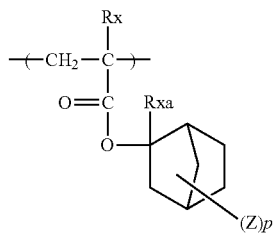

6

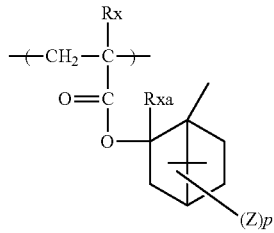

7

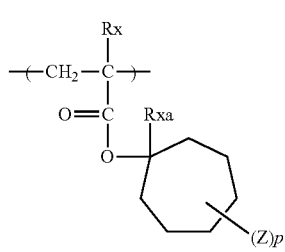

8

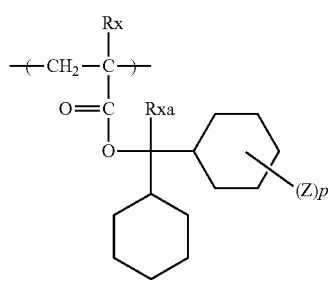
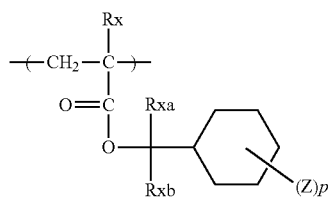
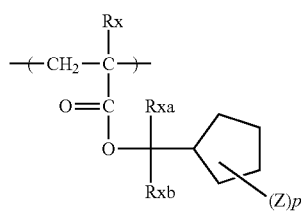
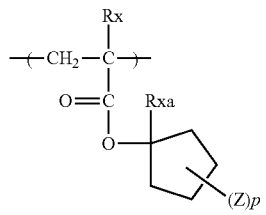
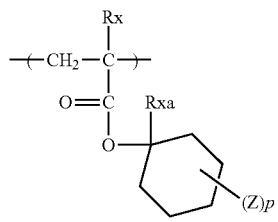
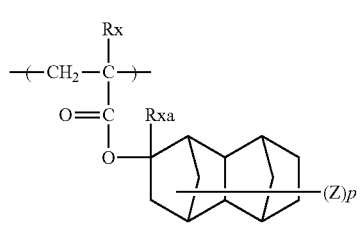
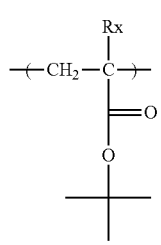
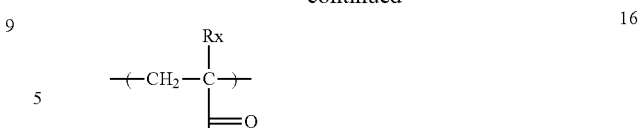
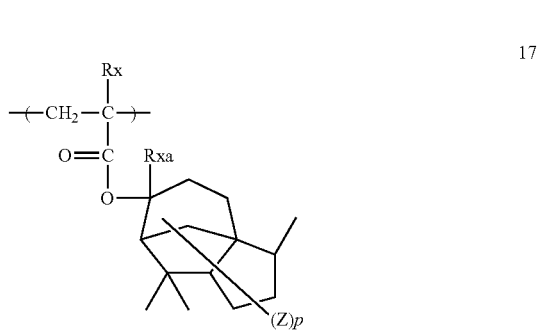
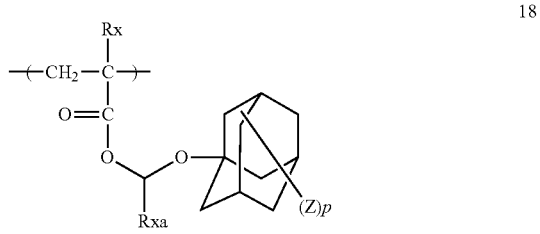
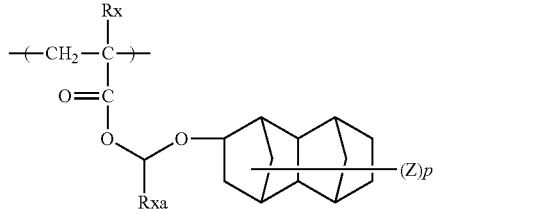
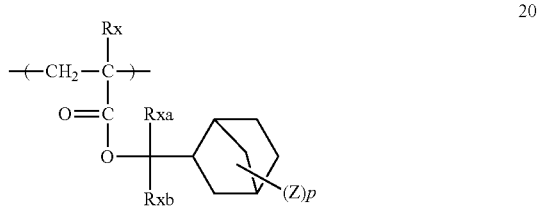
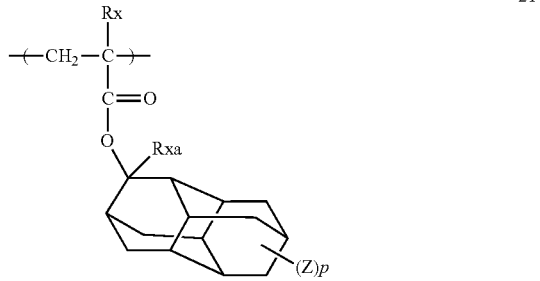

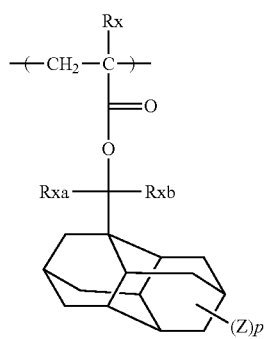
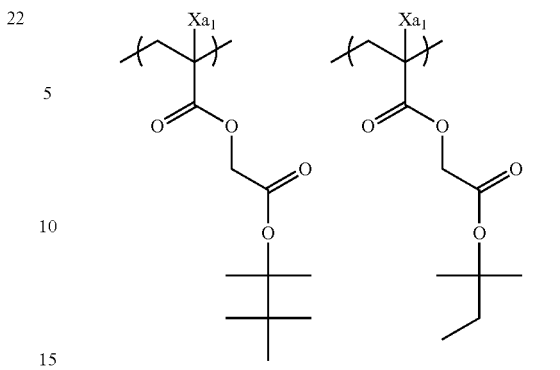
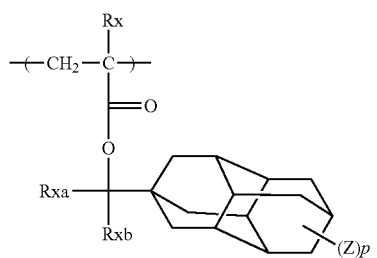
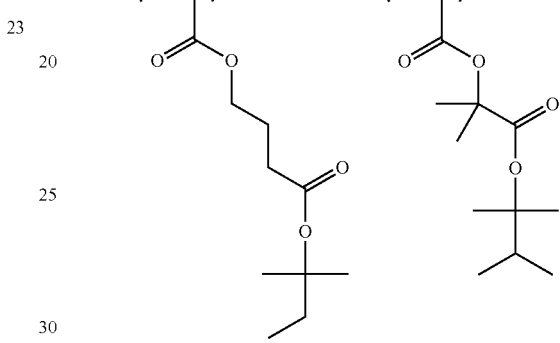
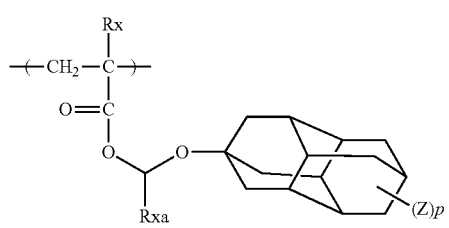
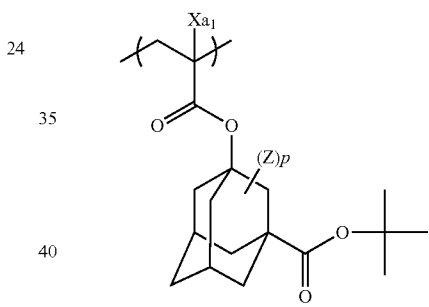
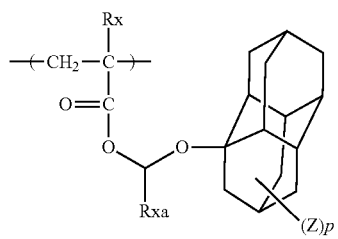
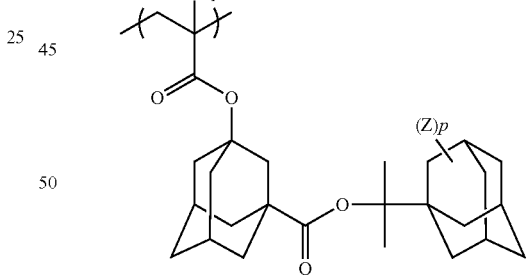
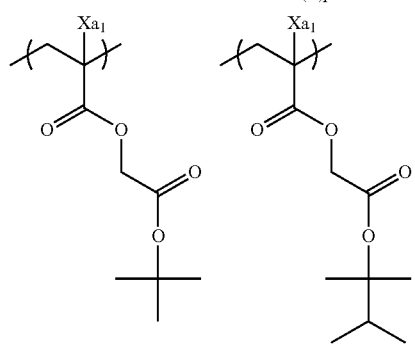
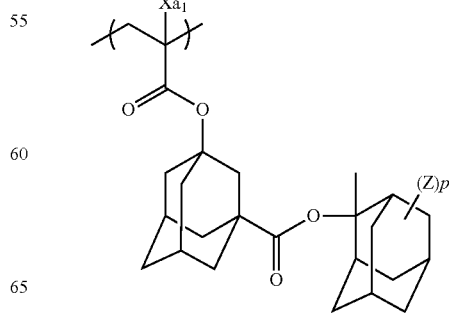

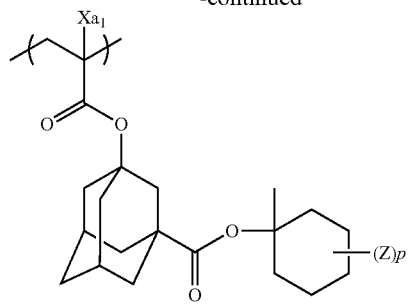
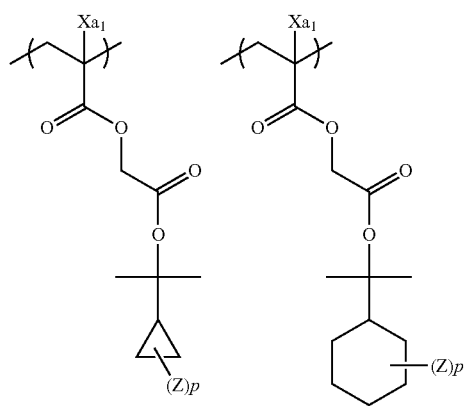
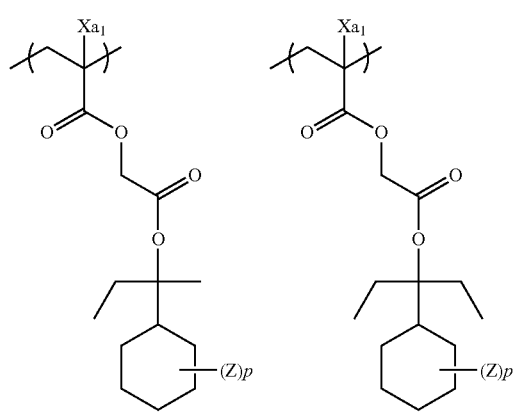
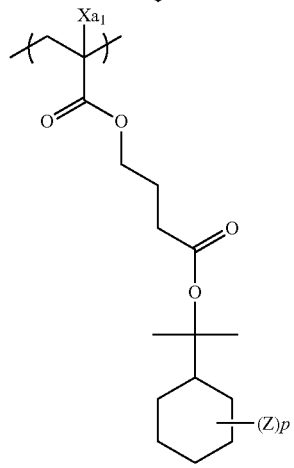
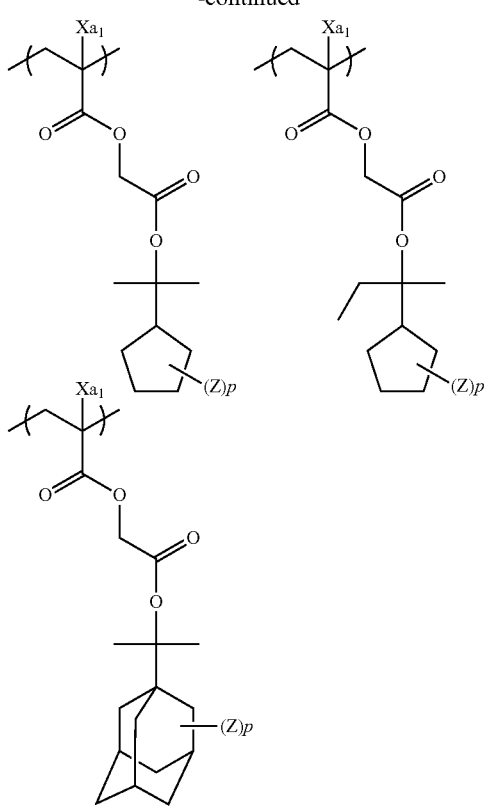
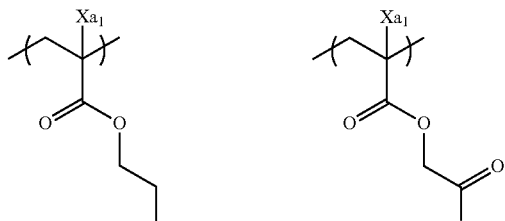
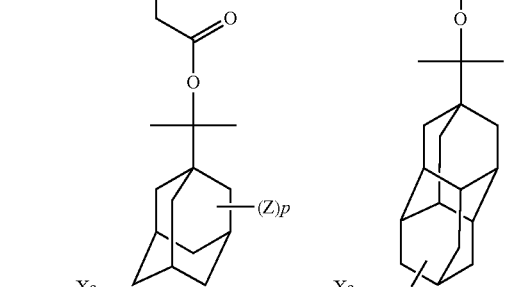
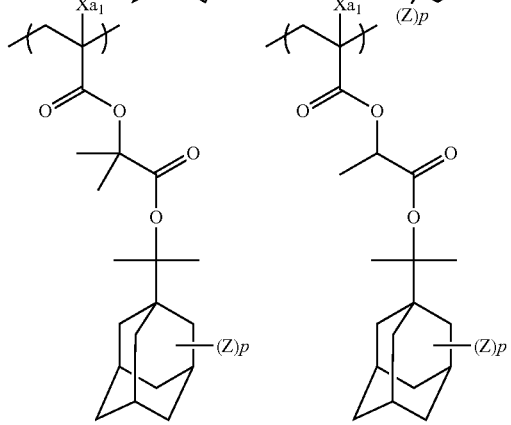

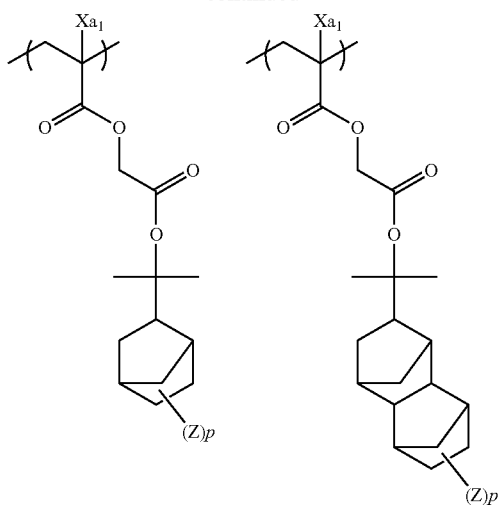
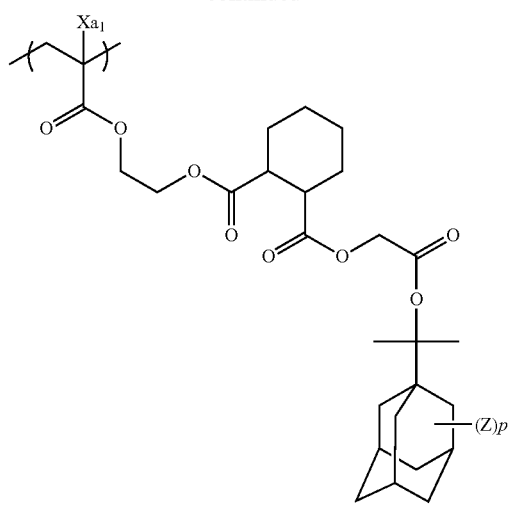
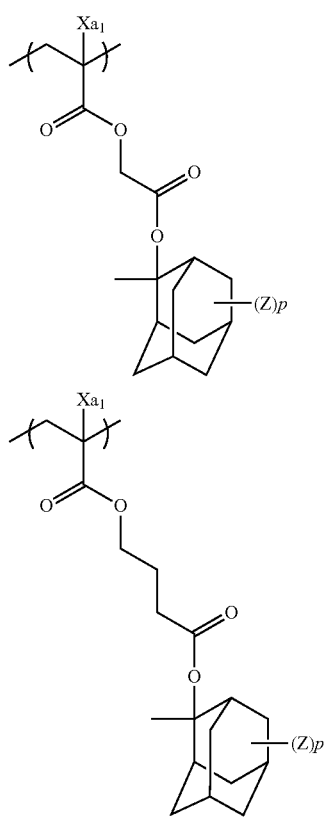
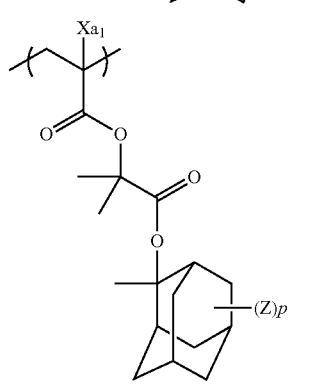

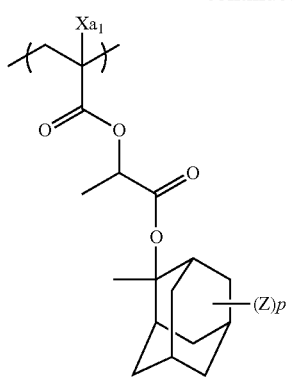
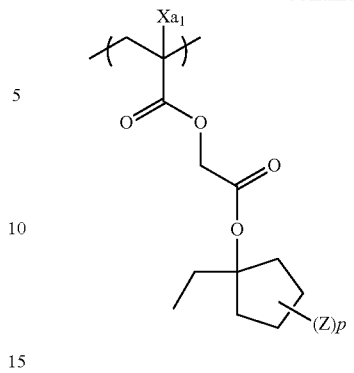
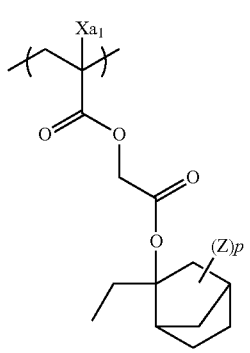
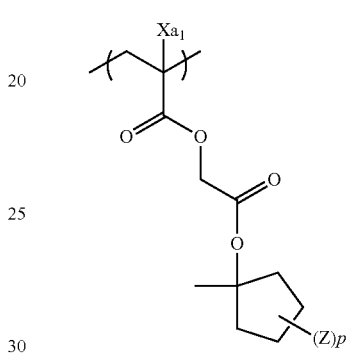
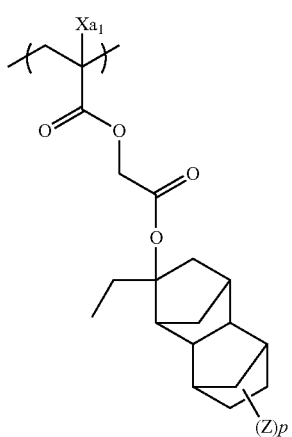
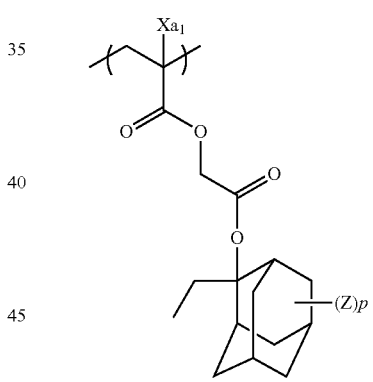
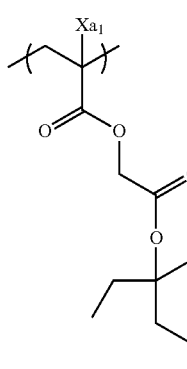
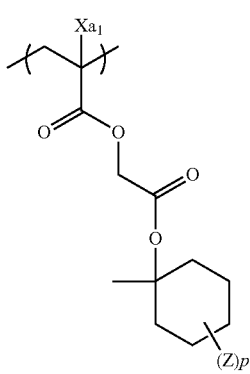
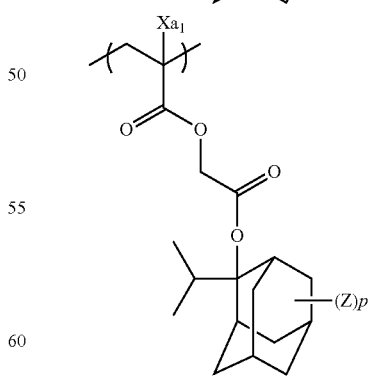
It is more preferred for the resin (B) to be a resin having, as the repeating units of the general formula (AI), at least any of the repeating units of general formula (I) below and repeating units of general formula (II) below.

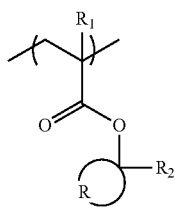

(I)

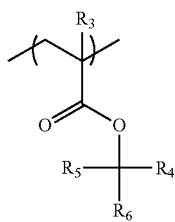

(II)

In general formulae (I) and (II), each of $R_1$ and $R_3$ independently represents a hydrogen atom, an optionally substituted methyl group or any of the groups of the formula —$CH_2$—$R_9$. $R_9$ represents a monovalent organic group.

Each of $R_2$, $R_4$, $R_5$ and $R_6$ independently represents an alkyl group or a cycloalkyl group.

R represents an atomic group required for forming an alicyclic structure in cooperation with a carbon atom.

$R_1$ preferably represents a hydrogen atom, a methyl group, a trifluoromethyl group or a hydroxymethyl group.

The alkyl group represented by $R_2$ may be linear or branched, and may have a substituent.

The cycloalkyl group represented by $R_2$ may be monocyclic or polycyclic, and may have a substituent.

$R_2$ preferably represents an alkyl group, more preferably an alkyl group having 1 to 10 carbon atoms, especially 1 to 5 carbon atoms. As examples thereof, there can be mentioned a methyl group and an ethyl group.

R represents an atomic group required for forming an alicyclic structure in cooperation with a carbon atom. The alicyclic structure formed by R is preferably an alicyclic structure of a single ring, and preferably has 3 to 7 carbon atoms, more preferably 5 or 6 carbon atoms.

$R_3$ preferably represents a hydrogen atom or a methyl group, more preferably a methyl group.

Each of the alkyl groups represented by $R_4$, $R_5$ and $R_6$ may be linear or branched, and may have a substituent. The alkyl groups preferably are those each having 1 to 4 carbon atoms, such as a methyl group, an ethyl group, an n-propyl group, an isopropyl group, an n-butyl group, an isobutyl group and a t-butyl group.

Each of the cycloalkyl groups represented by $R_4$, $R_5$ and $R_6$ may be monocyclic or polycyclic, and may have a substituent. The cycloalkyl groups are preferably a cycloalkyl group of a single ring, such as a cyclopentyl group or a cyclohexyl group, and a cycloalkyl group of multiple rings, such as a norbornyl group, a tetracyclodecanyl group, a tetracyclododecanyl group or an adamantyl group.

The repeating units of general formula (II) are preferably those of general formula (II-1) below.

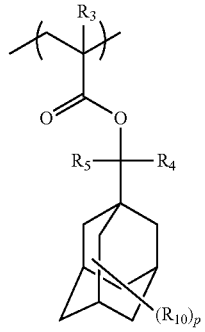

(II-1)

In the general formula (II-1), $R_3$ to $R_5$ have the same meaning as in the general formula (II).

$R_{10}$ represents a substituent containing a polar group. When a plurality of $R_{10}$s exist, they may be identical to or different from each other. As the substituent containing a polar group, there can be mentioned, for example, a linear or branched alkyl group, or cycloalkyl group, having a hydroxyl group, a cyano group, an amino group, an alkylamido group or a sulfonamido group. An alkyl group having a hydroxyl group is preferred. An isopropyl group is especially preferred as the branched alkyl group.

In the formula, p is an integer of 0 to 15, preferably in the range of 0 to 2, and more preferably 0 or 1.

When a plurality of acid-decomposable repeating units are simultaneously used in the resin (B), preferred combinations thereof are shown below. In the following formulae, each of Rs independently represents a hydrogen atom or a methyl group.

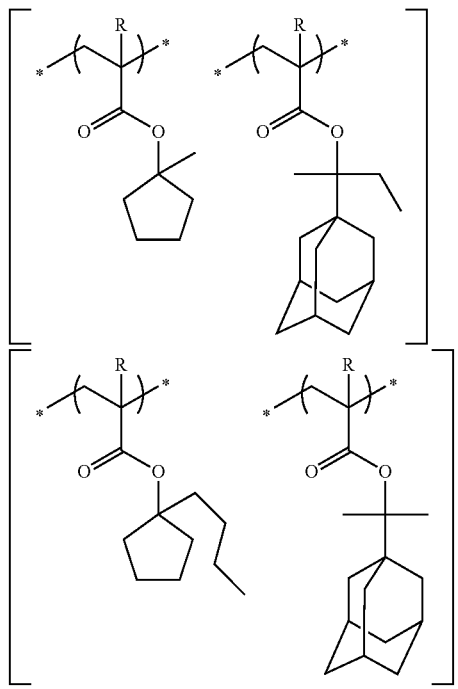

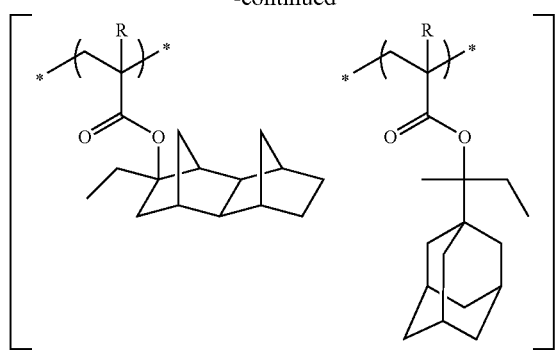

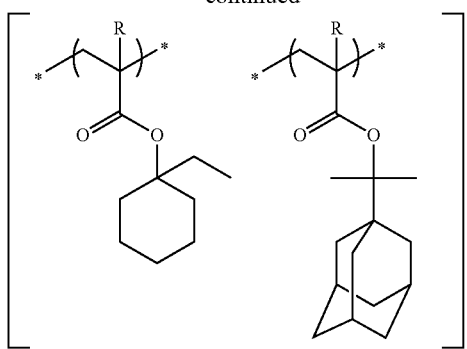
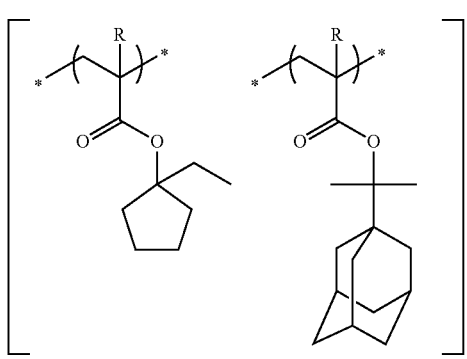
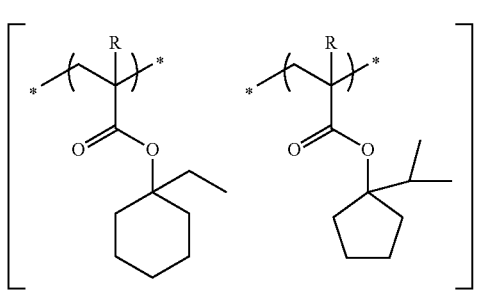
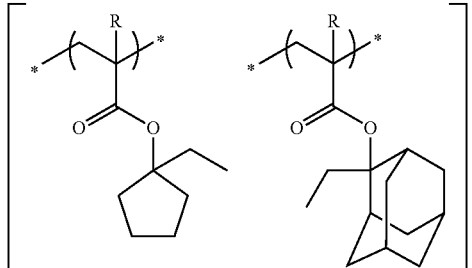
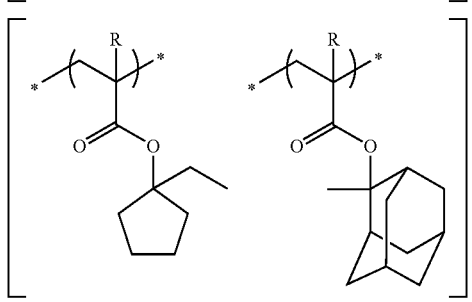
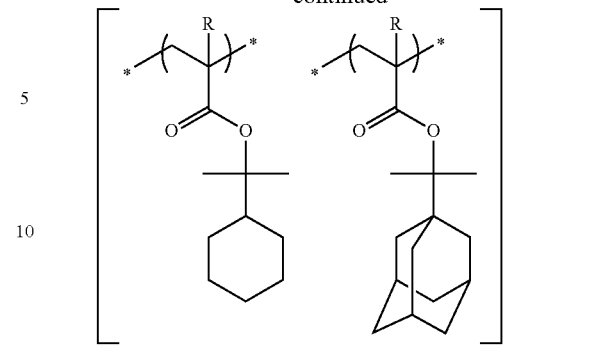
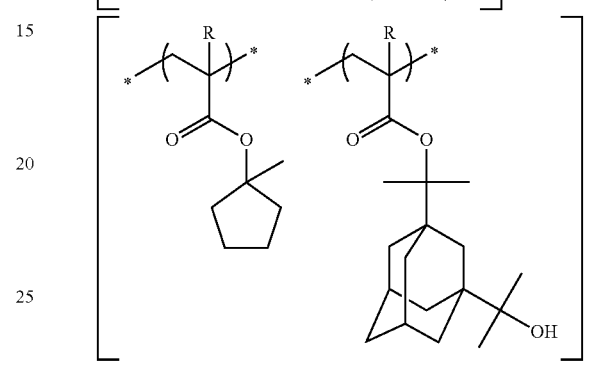
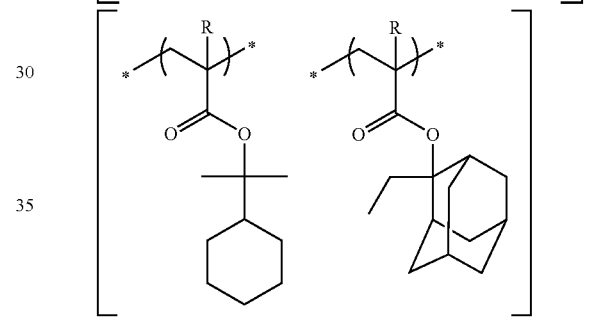
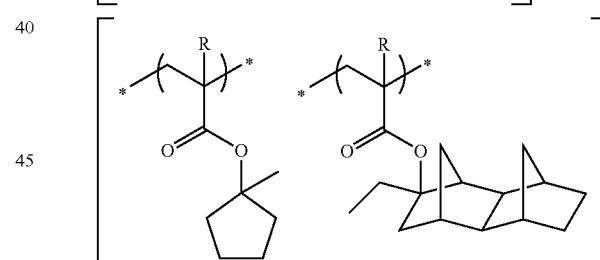
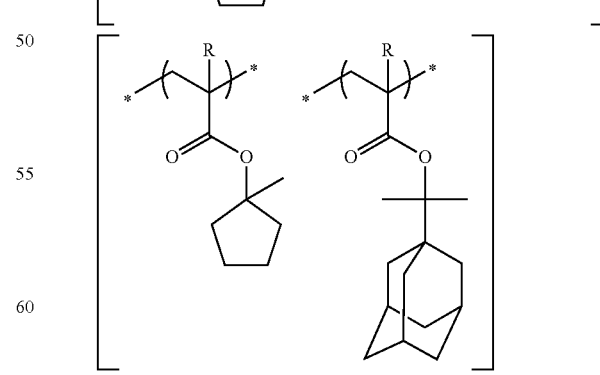
It is preferred for resin (B) to contain any of the repeating units having a lactone group represented by the following general formula (III).

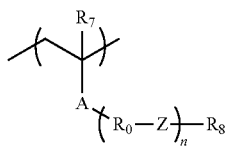
(III)

In formula (III),

A represents an ester bond (—COO—) or an amido bond (—CONH—).

$R_0$, each independently in the presence of two or more groups, represents an alkylene group, a cycloalkylene group or a combination thereof.

Z, each independently in the presence of two or more groups, represents an ether bond, an ester bond, an amido bond, a urethane bond
(a group represented by

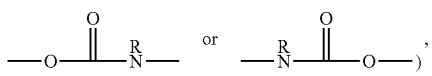

or a urea bond
(a group represented by

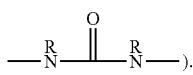

Each of Rs independently represents a hydrogen atom, an alkyl group, cycloalkyl group or an aryl group.

$R_8$ represents a monovalent organic group with a lactone structure.

n represents the number of repetitions of the structure of the formula —$R_0$—Z— and is an integer of 1 to 5.

$R_7$ represents a hydrogen atom, a halogen atom or an optionally substituted alkyl group.

Each of the alkylene group and cycloalkylene group represented by $R_0$ may have a substituent.

Z preferably represents an ether bond or an ester bond, most preferably an ester bond.

The alkyl group represented by $R_7$ is preferably an alkyl group having 1 to 4 carbon atoms, more preferably a methyl group or an ethyl group and most preferably a methyl group. The alkyl group represented by $R_7$ may be substituted. As substituents on $R_7$, there can be mentioned, for example, a halogen atom such as a fluorine atom, a chlorine atom or a bromine atom, a mercapto group, a hydroxyl group, an alkoxy group such as a methoxy group, an ethoxy group, an isopropoxy group, a t-butoxy group or a benzyloxy group, an acyl group such as an acetyl group or a propionyl group, an acetoxy group and the like. $R_7$ preferably represents a hydrogen atom, a methyl group, a trifluoromethyl group or a hydroxymethyl group.

The alkylene group represented by $R_0$ is preferably a chain alkylene group having 1 to 10 carbon atoms, more preferably 1 to 5 carbon atoms, for example, a methylene group, an ethylene group, a propylene group or the like. The cycloalkylene group is preferably a cycloalkylene group having 3 to 20 carbon atoms. As such, there can be mentioned, for example, cyclohexylene, cyclopentylene, norbornylene, adamantylene or the like. The chain alkylene groups are preferred from the viewpoint of the exertion of the effect of the present invention. A methylene group is most preferred.

The substituent with a lactone structure represented by $R_8$ is not limited as long as the lactone structure is contained. As particular examples thereof, there can be mentioned the lactone structures of the above general formulae (LC1-1) to (LC1-17). Of these, the structures of general formula (LC1-4) are most preferred. In general formulae (LC1-1) to (LC1-17), $n_2$ is more preferably 2 or less.

$R_8$ preferably represents a monovalent organic group with an unsubstituted lactone structure or a monovalent organic group with a lactone structure substituted with a methyl group, a cyano group or an alkoxycarbonyl group. More preferably, $R_8$ represents a monovalent organic group with a lactone structure substituted with a cyano group (cyanolactone).

Specific examples of the repeating units having groups with a lactone structure of general formula (III) will be shown below, which however in no way limit the scope of the present invention.

In the following specific examples, R represents a hydrogen atom, an optionally substituted alkyl group or a halogen atom. Preferably, R represents a hydrogen atom, a methyl group, a hydroxymethyl group or an acetoxymethyl group.

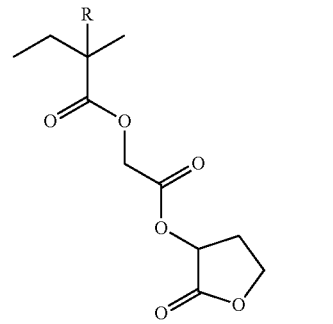

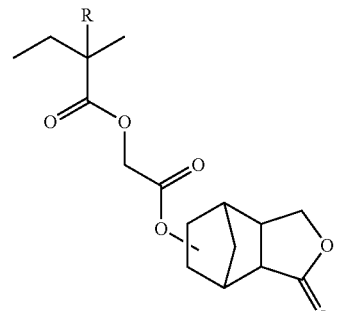

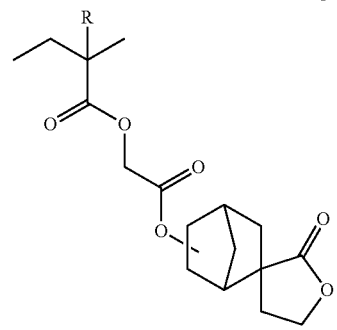

-continued

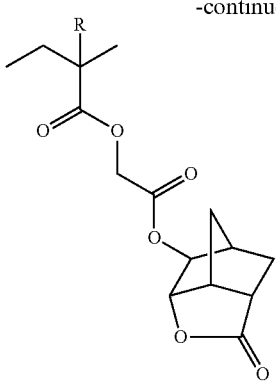

As more preferred repeating units with a lactone structure, there can be mentioned the repeating units of general formula (III-1), below.

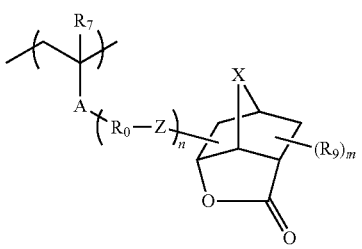
(III-1)

In general formula (III-1), $R_7$, A, $R_0$, Z and n are as defined above with respect to general formula (III).

$R_9$, each independently in the presence of two or more groups, represents an alkyl group, a cycloalkyl group, an alkoxycarbonyl group, a cyano group, a hydroxyl group or an alkoxy group. In the presence of two or more groups, two $R_9$s may be bonded to each other to thereby form a ring.

X represents an alkylene group, an oxygen atom or a sulfur atom, and m is the number of substituents and is an integer of 0 to 5. Preferably, m is 0 or 1.

The alkyl group represented by $R_9$ is preferably an alkyl group having 1 to 4 carbon atoms, more preferably a methyl group or an ethyl group and most preferably a methyl group. As the cycloalkyl group, there can be mentioned a cyclopropyl group, a cyclobutyl group, a cyclopentyl group or a cyclohexyl group. As the alkoxycarbonyl group, there can be mentioned a methoxycarbonyl group, an ethoxycarbonyl group, an n-butoxycarbonyl group, a t-butoxycarbonyl group or the like. As the substituent therefor, there can be mentioned a hydroxyl group, an alkoxy group such as a methoxy group or an ethoxy group, a cyano group, or a halogen atom such as a fluorine atom. More preferably, $R_9$ represents a methyl group, a cyano group or an alkoxycarbonyl group, still more preferably a cyano group.

As the alkylene group represented by X, there can be mentioned a methylene group, an ethylene group or the like. Preferably, X represents an oxygen atom or a methylene group, more preferably a methylene group.

When m is 1 or greater, the substitution site of at least one $R_9$ is preferably the α-position or β-position of the carbonyl group of the lactone. The substitution at the α-position is especially preferred.

Specific examples of the repeating units having groups with a lactone structure expressed by general formula (III-1) will be shown below, which however in no way limit the scope of the present invention. In the following specific examples, R represents a hydrogen atom, an optionally substituted alkyl group or a halogen atom. Preferably, R represents a hydrogen atom, a methyl group, a hydroxymethyl group or an acetoxymethyl group.

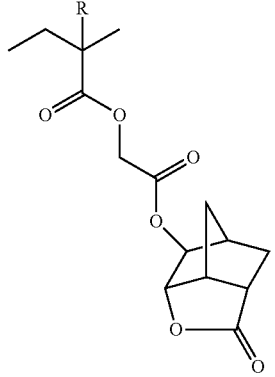

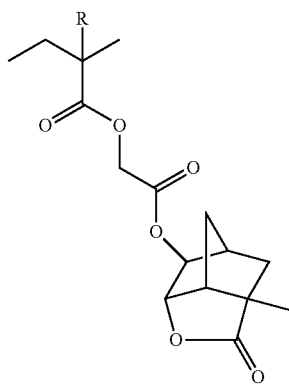

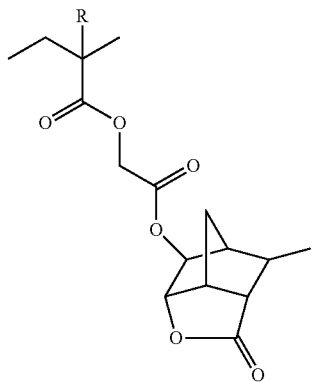

| 91 | 92 |
|---|---|
| -continued | -continued |
| 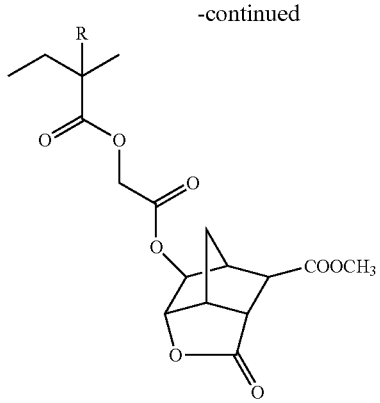 | 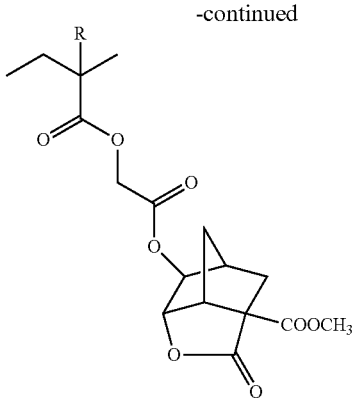 |
| 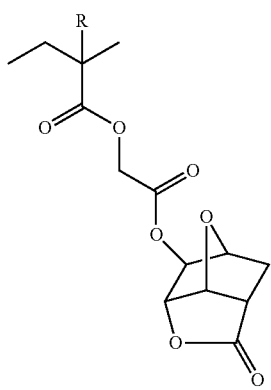 | 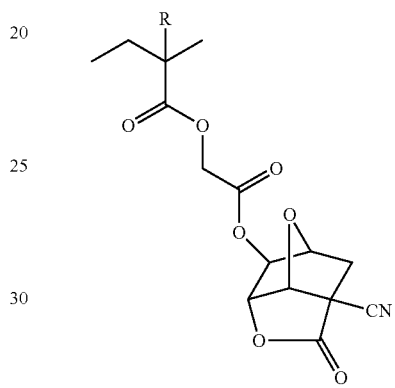 |
|  | 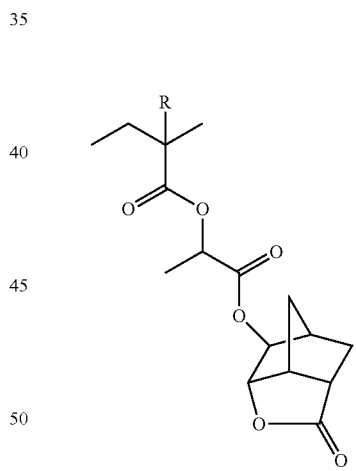 |
| 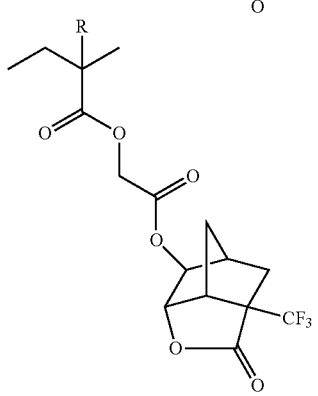 | 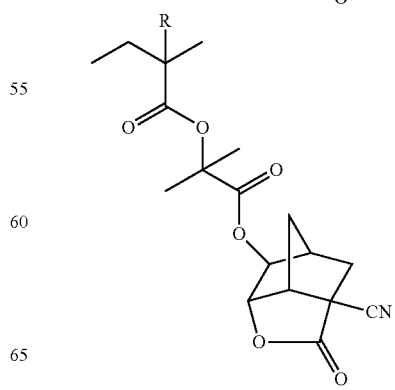 |

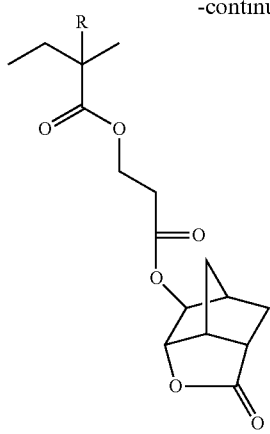
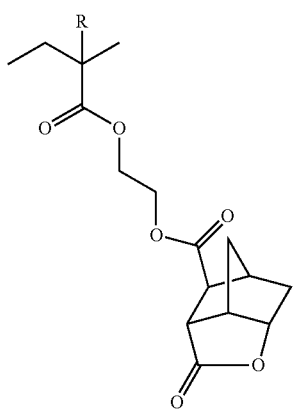
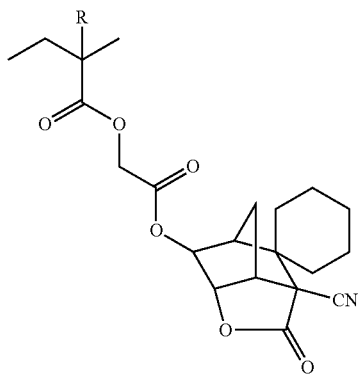
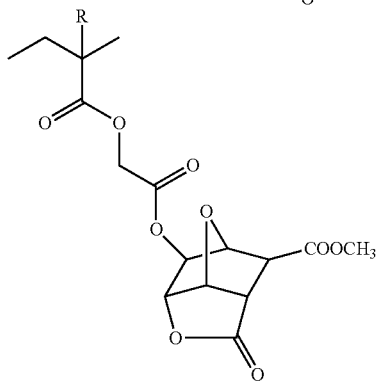
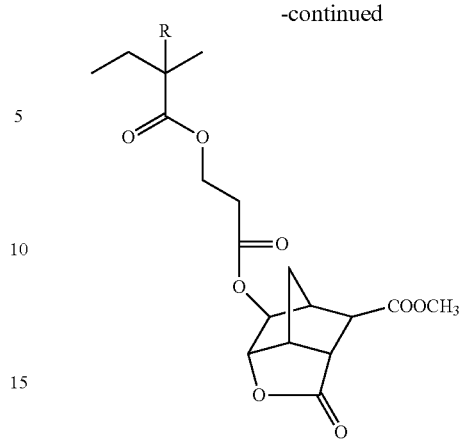
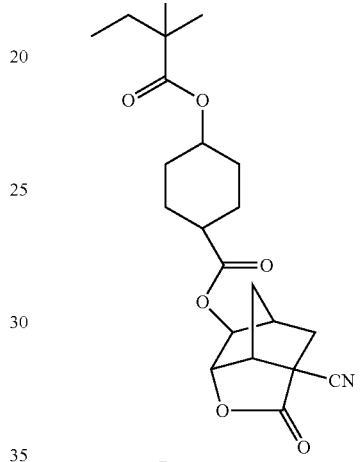
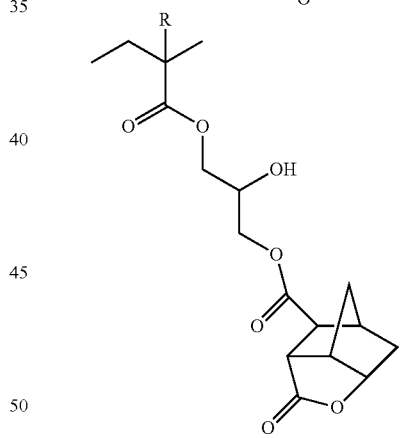
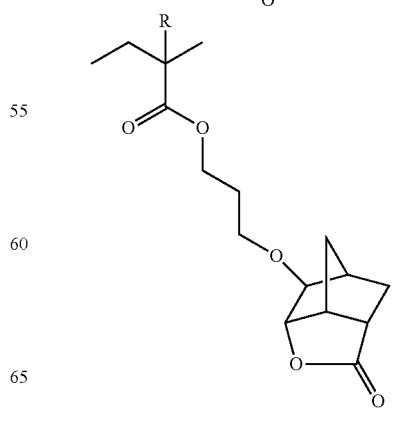

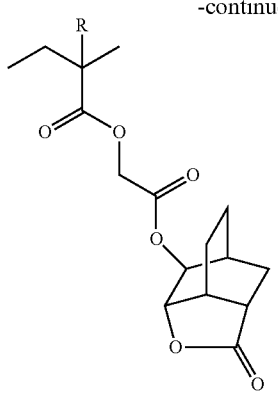
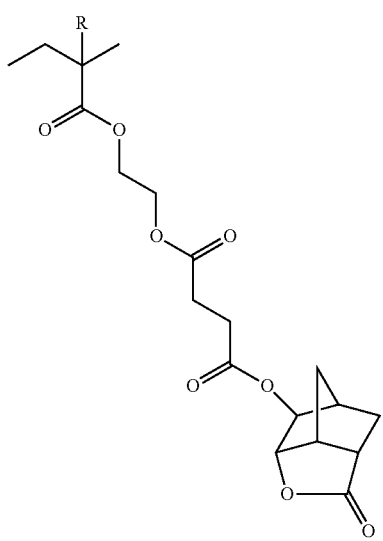
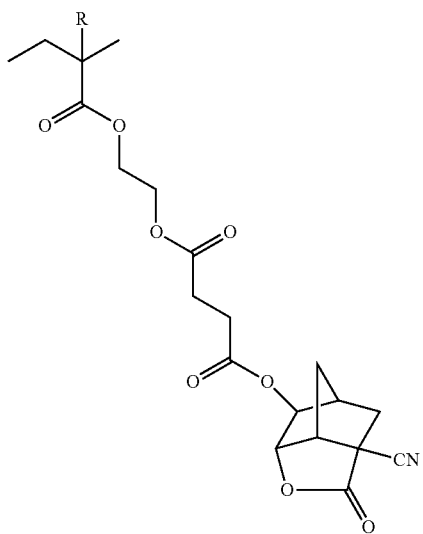

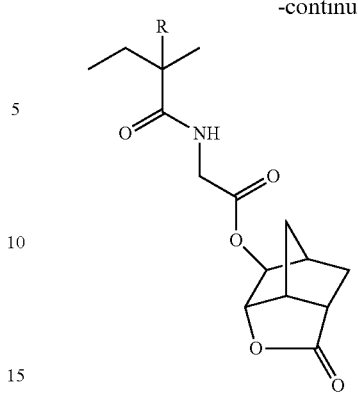
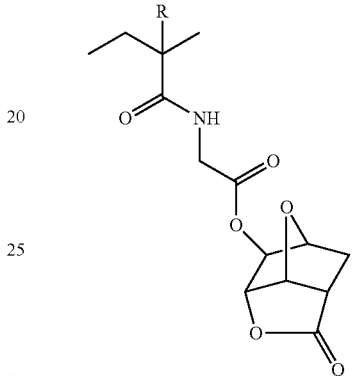
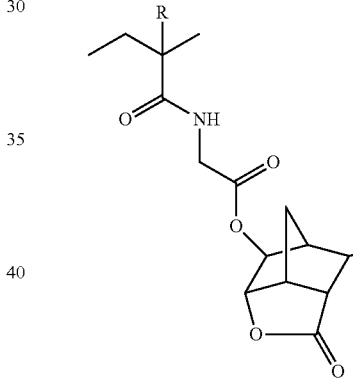

The content ratio of any of the repeating units, in the instance of two or more the sum thereof, of general formula (III) in the resin based on all the repeating units of the resin is preferably in the range of 15 to 60 mol %, more preferably 20 to 60 mol % and further more preferably 30 to 50 mol %.

The resin (B) may contain a repeating unit having a lactone group other than the units of general formula (III).

Any lactone groups can be employed as long as a lactone structure is possessed therein. However, lactone structures of a 5 to 7-membered ring are preferred, and in particular, those resulting from condensation of lactone structures of a 5 to 7-membered ring with other cyclic structures effected in a fashion to form a bicyclo structure or spiro structure are preferred. The possession of repeating units having a lactone structure represented by any of the following general formulae (LC1-1) to (LC1-17) is more preferred. The lactone structures may be directly bonded to the principal chain of the resin. Preferred lactone structures are those of formulae (LC1-1), (LC1-4), (LC1-5), (LC1-6), (LC1-13), (LC1-14) and (LC1-17). The use of these specified lactone structures would ensure improvement in the LWR and development defect.

-continued
| | |
|---|---|
| 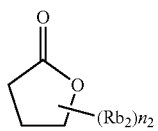 LC1-1 | 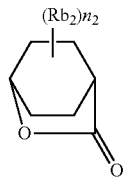 LC1-9 |
| 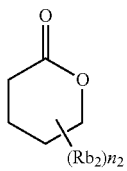 LC1-2 | 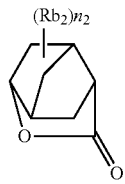 LC1-10 |
| 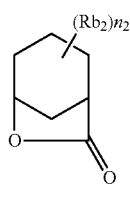 LC1-3 | 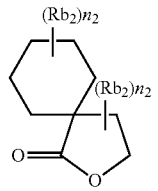 LC1-11 |
| 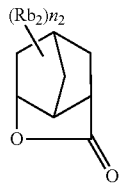 LC1-4 | 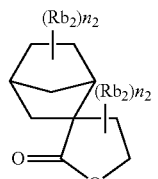 LC1-12 |
| 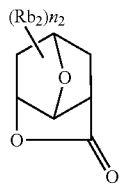 LC1-5 | 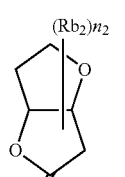 LC1-13 |
| 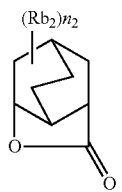 LC1-6 | 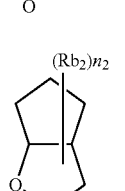 LC1-14 |
| 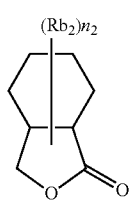 LC1-7 | 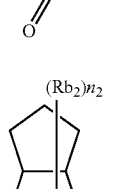 LC1-15 |
| 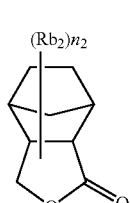 LC1-8 | 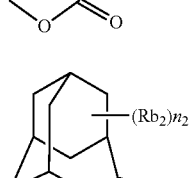 LC1-16 |

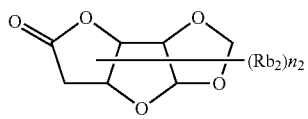
LC1-17

The presence of a substituent (Rb₂) on the portion of the lactone structure is optional. As a preferred substituent (Rb₂), there can be mentioned an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group or the like. Of these, an alkyl group having 1 to 4 carbon atoms, a cyano group and an acid-decomposable group are more preferred. In the formulae, $n_2$ is an integer of 0 to 4. When $n_2$ is 2 or greater, the plurality of present substituents (Rb₂) may be identical to or different from each other. Further, the plurality of present substituents (Rb₂) may be bonded to each other to thereby form a ring.

The repeating units of general formula (AII'), below, can preferably be employed as the repeating units with a lactone structure other than the units of general formula (III).

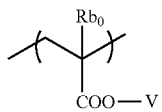
(AII')

In general formula (AII'),

Ab₀ represents a hydrogen atom, a halogen atom or an optionally substituted alkyl group having 1 to 4 carbon atoms. As a preferred substituent optionally contained in the alkyl group represented by Ab₀, there can be mentioned a hydroxyl group or a halogen atom. As the halogen atom represented by Ab₀, there can be mentioned a fluorine atom, a chlorine atom, a bromine atom or an iodine atom. The Ab₀ is preferably a hydrogen atom, a methyl group, a hydroxymethyl group or a trifluoromethyl group. A hydrogen atom and a methyl group are especially preferred.

V represents a group with a structure represented by any of general formulae (LC1-1) to (LC1-17).

Specific examples of the repeating units having a lactone group other than the units of general formula (III) will be shown below, which however in no way limit the scope of the present invention.

In the following formulae, Rx represents H, CH₃, CH₂OH or CF₃.

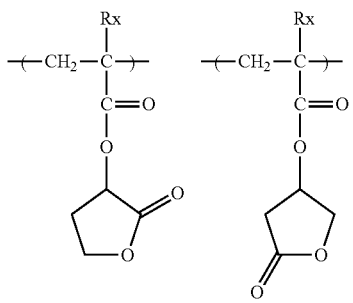

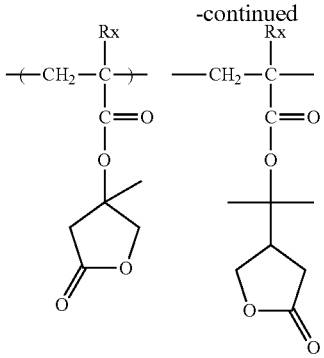

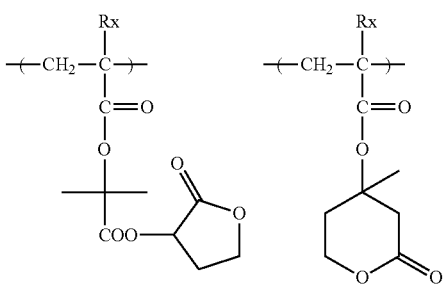

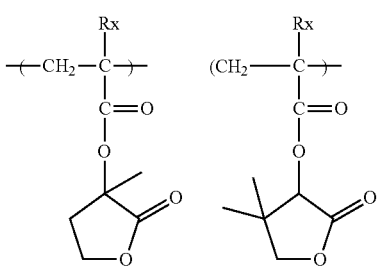

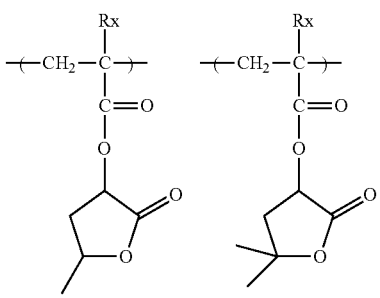

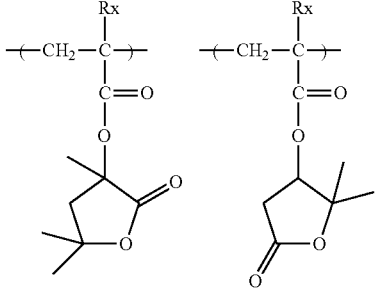

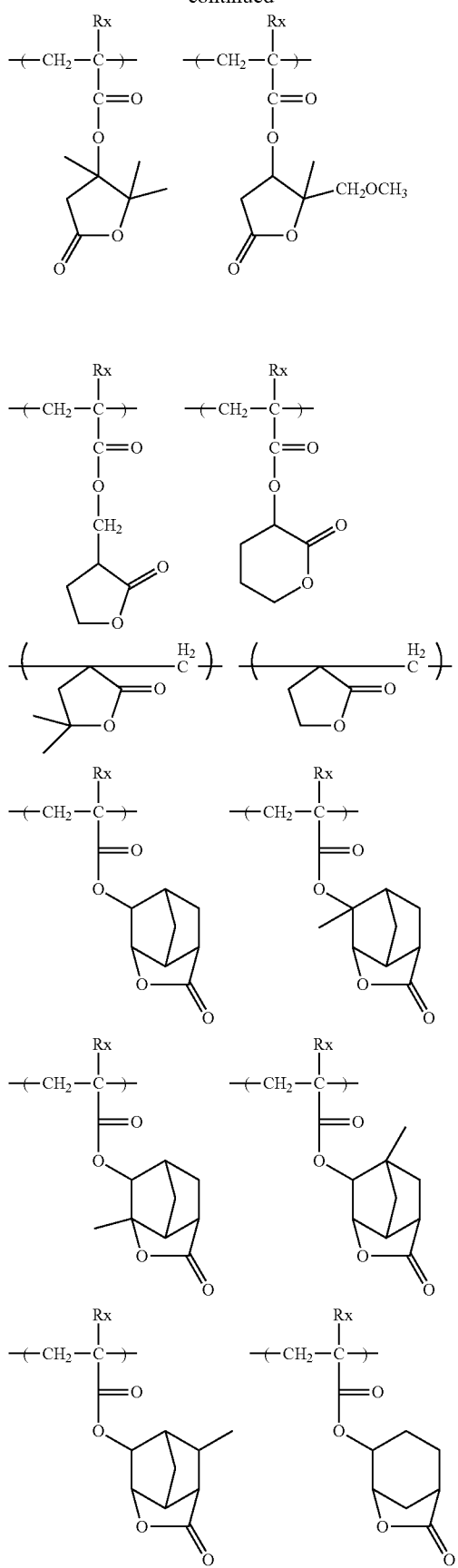
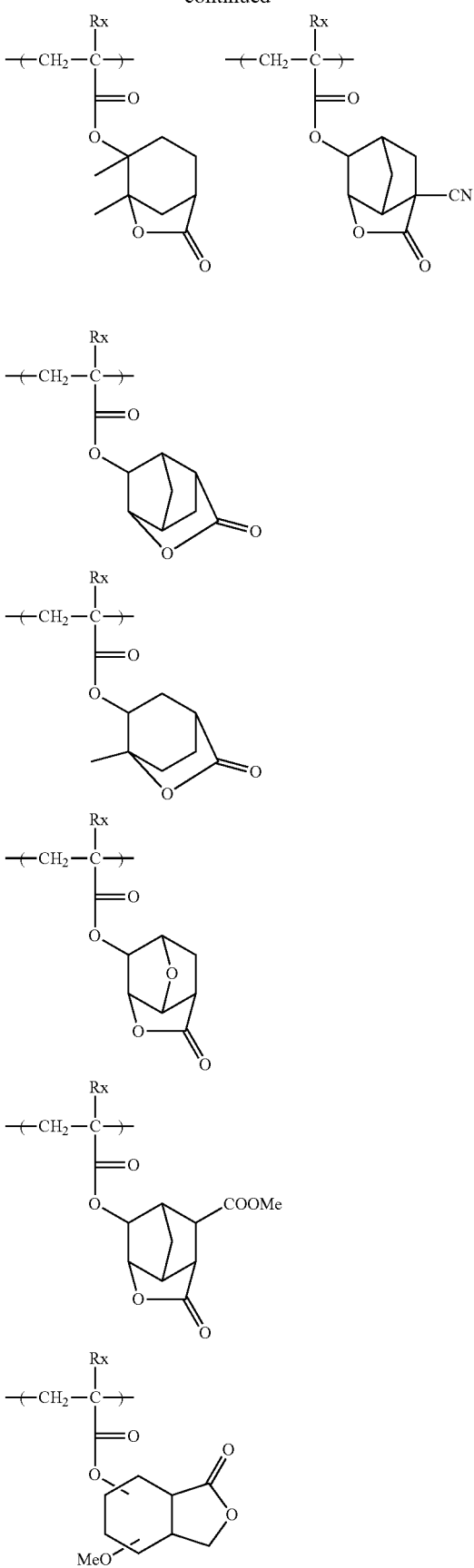

103
-continued
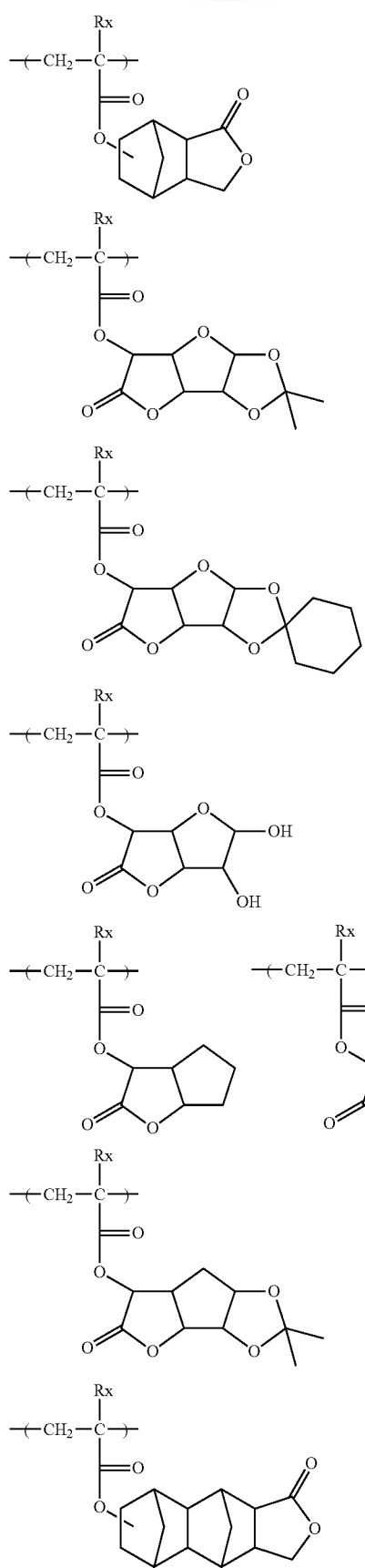
104
-continued
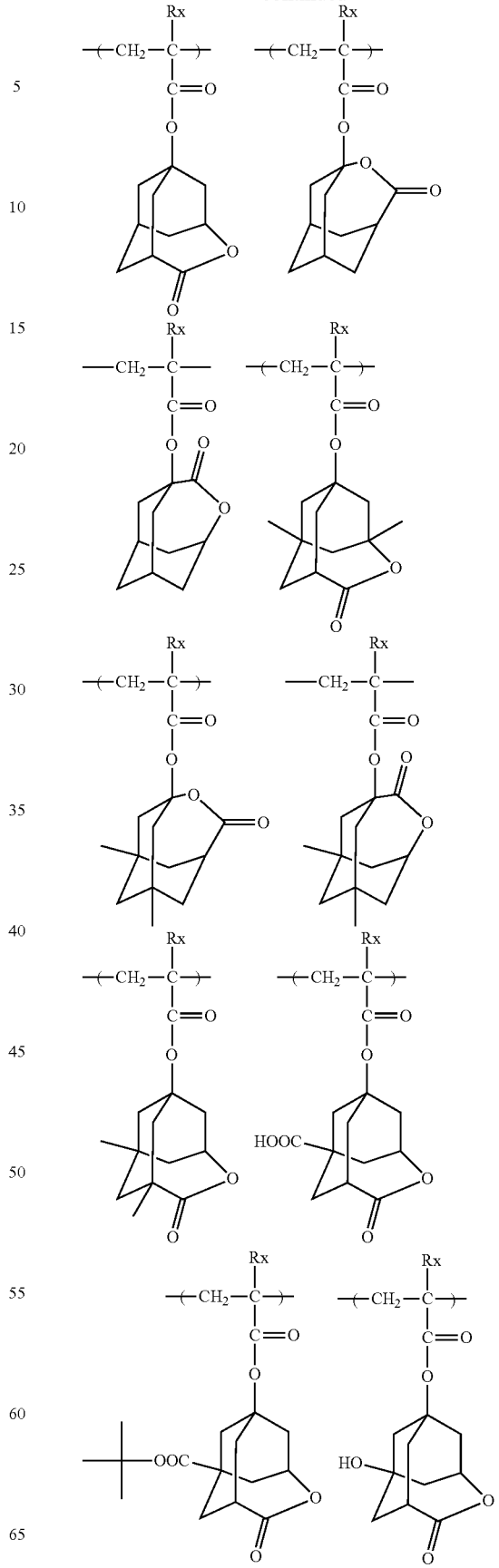

-continued

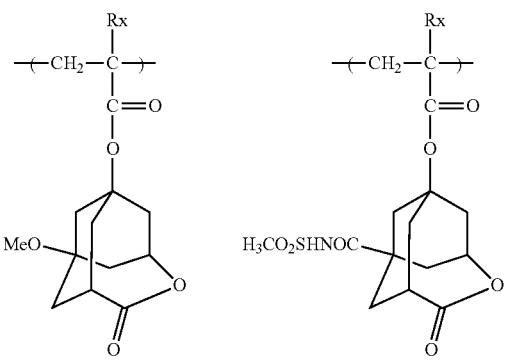

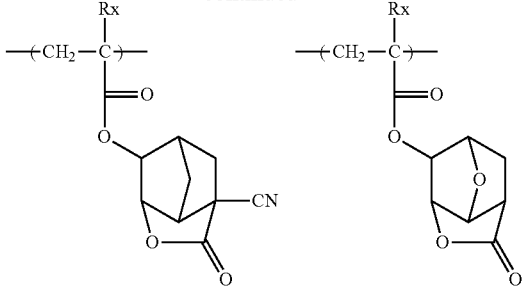

The repeating units other than the repeating units of general formula (III), having an especially preferred lactone group will be shown below. An improvement in pattern profile and iso-dense bias can be attained by selection of the most appropriate lactone group.

In the following formulae, Rs represents H, CH$_3$, CH$_2$OH or CF$_3$.

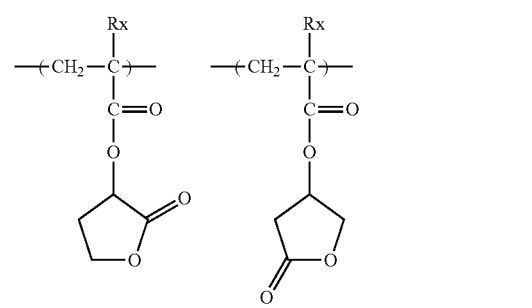

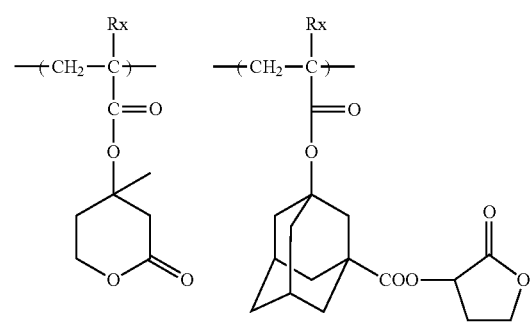

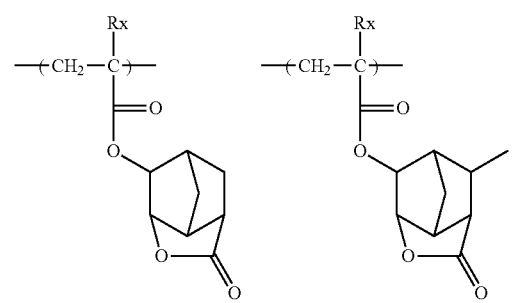

The repeating unit having a lactone group is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity (ee) thereof is preferably 90 or higher, more preferably 95 or higher.

The content ratio of the repeating units other than the repeating units of general formula (III), having a lactone group, the sum thereof when a plurality of repeating units are contained, is preferably in the range of 15 to 60 mol %, more preferably 20 to 50 mol % and still more preferably 30 to 50 mol %, based on all the repeating units contained in the resin (B).

Two or more types of lactone repeating units selected from among those of general formula (III) can be simultaneously employed in order to enhance the effects of the present invention. In the simultaneous employment, it is preferred to select the two or more types from the lactone repeating units of the general formula (III) in which n is 1.

It is preferred for the resin (B) to have a repeating unit other than the repeating units of general formulae (AI) and (III), having a hydroxyl group or a cyano group. The containment of this repeating unit would realize enhancements of adhesion to substrate and developer affinity.

The repeating unit having a hydroxyl group or a cyano group is preferably a repeating unit with a structure of alicyclic hydrocarbon substituted with a hydroxyl group or a cyano group, and preferably has no acid-decomposable group. In the alicyclic hydrocarbon structure substituted with a hydroxyl group or a cyano group, the alicyclic hydrocarbon structure preferably consists of an adamantyl group, a diamantyl group or a norbornane group. As preferred alicyclic hydrocarbon structures substituted with a hydroxyl group or a cyano group, there can be mentioned the partial structures of general formulae (VIIa) to (VIId), below.

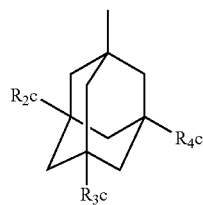

(VIIa)

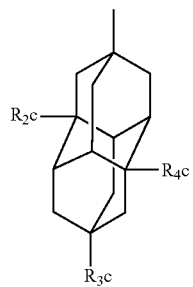

(VIIb)

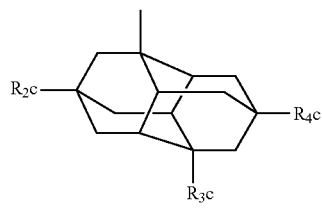

(VIIc)

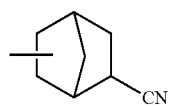

(VIId)

In the general formulae (VIIa) to (VIIc), each of $R_2c$ to $R_4c$ independently represents a hydrogen atom, a hydroxyl group or a cyano group, providing that at least one of the $R_2c$ to $R_4c$ represents a hydroxyl group or a cyano group. Preferably, one or two of the $R_2c$ to $R_4c$ are hydroxyl groups and the remainder is a hydrogen atom. In the general formula (VIIa), more preferably, two of the $R_2c$ to $R_4c$ are hydroxyl groups and the remainder is a hydrogen atom.

As the repeating units having any of the partial structures of the general formulae (VIIa) to (VIId), there can be mentioned those of the following general formulae (AIIa) to (AIId).

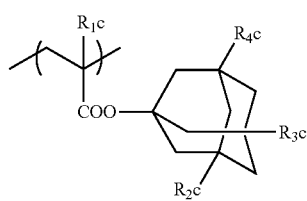

(AIIa)

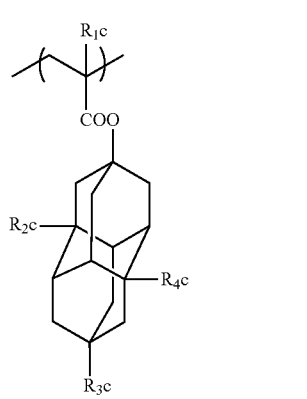

(AIIb)

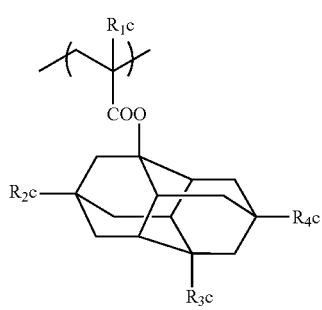

(AIIc)

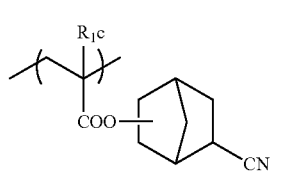

(AIId)

In the general formulae (AIIa) to (AIId), $R_1c$ represents a hydrogen atom, a methyl group, a trifluoromethyl group or a hydroxymethyl group.

$R_2c$ to $R_4c$ have the same meaning as those of the general formulae (VIIa) to (VIIc).

The content ratio of the repeating unit having a hydroxyl group or a cyano group, based on all the repeating units of the resin (B), is preferably in the range of 5 to 40 mol %, more preferably 5 to 30 mol % and still more preferably 10 to 25 mol %.

Specific examples of the repeating units having a hydroxyl group or a cyano group will be shown below, which however in no way limit the scope of the present invention.

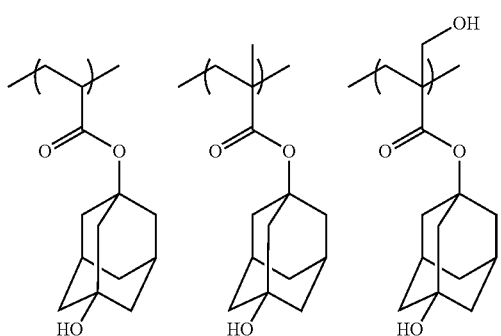
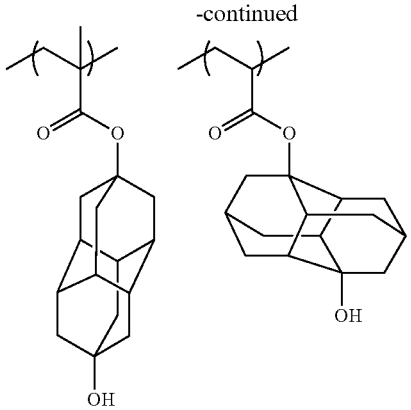
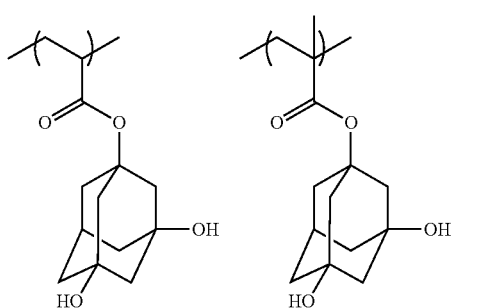
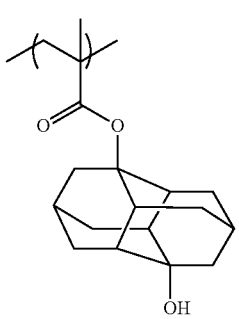
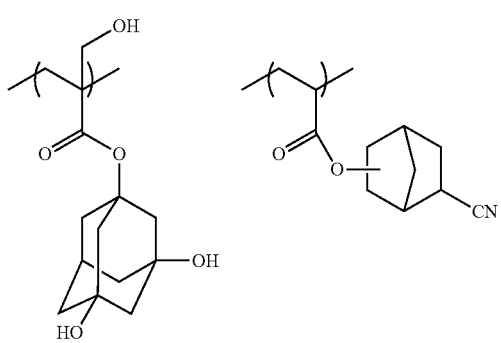
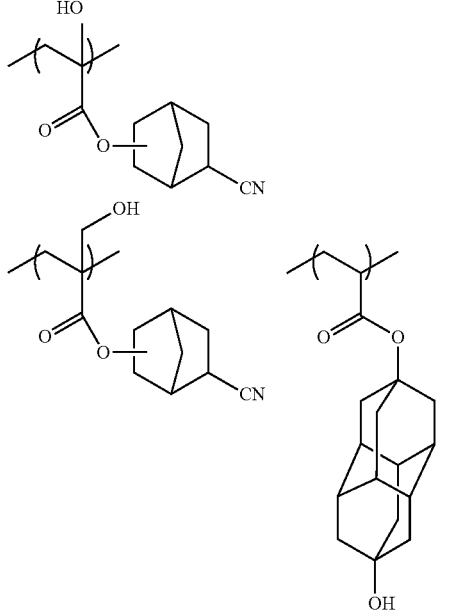

It is preferred for the resin (B) to contain a repeating unit having an alkali-soluble group. As the alkali-soluble group, there can be mentioned a carboxyl group, a sulfonamido group, a sulfonylimido group, a bisulfonylimido group or an aliphatic alcohol substituted at its α-position with an electron-withdrawing group (for example, a hexafluoroisopropanol group). The possession of a repeating unit having a carboxyl group is more preferred. The incorporation of the repeating unit having an alkali-soluble group would increase the resolving power in contact hole usage. The repeating unit having an alkali-soluble group is preferably any of a repeating unit wherein the alkali-soluble group is directly bonded to the principal chain of a resin such as a repeating unit of acrylic acid or methacrylic acid, a repeating unit wherein the alkali-soluble group is bonded via a connecting group to the principal chain of a resin and a repeating unit wherein the alkali-soluble group is introduced in a terminal of a polymer chain by the use of a chain transfer agent or polymerization initiator having the alkali-soluble group in the stage of polymerization. The connecting group may have a cyclohydrocarbon structure of a single ring or multiple rings. The repeating unit of acrylic acid or methacrylic acid is especially preferred.

The content ratio of the repeating unit having an alkali-soluble group based on all the repeating units of the resin (B) is preferably in the range of 0 to 20 mol %, more preferably 3 to 15 mol % and still more preferably 5 to 10 mol %.

Specific examples of the repeating units having an alkali-soluble group will be shown below, which however in no way limit the scope of the present invention.

In the formulae, Rx represents H, CH₃, CH₂OH or CF₃.

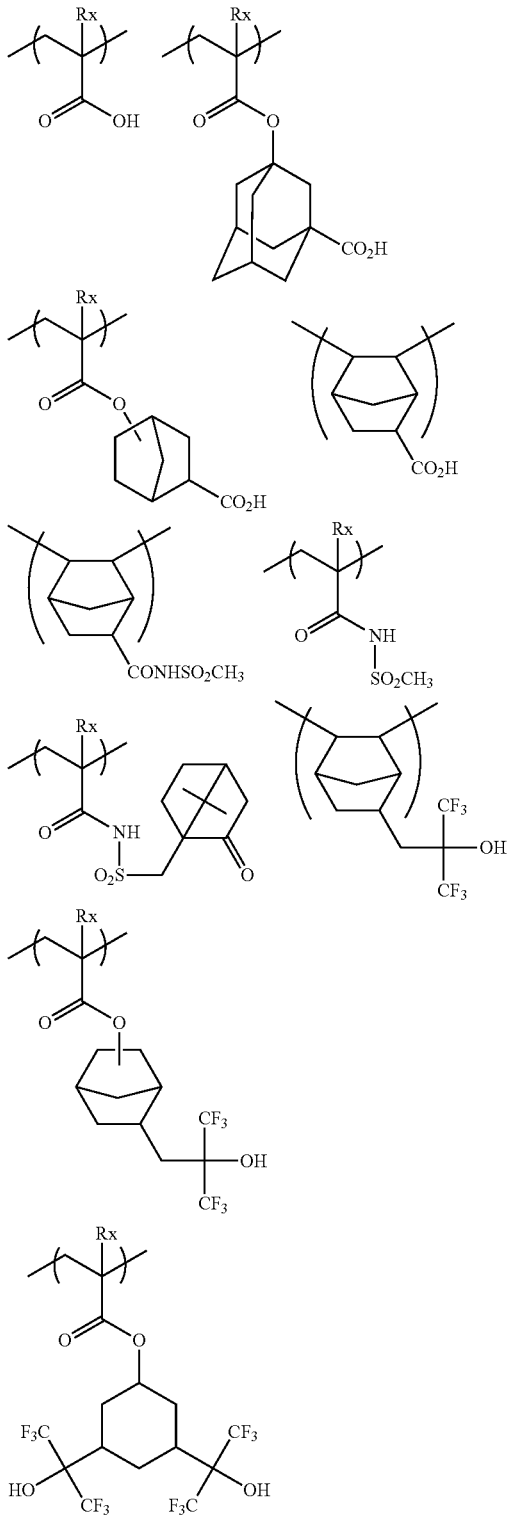

Resin (B) according to the present invention can further contain a repeating unit that has a structure of alicyclic hydrocarbon having no polar group, exhibiting no acid decomposability. As such a repeating unit, there can be mentioned any of the repeating units of general formula (IV) below.

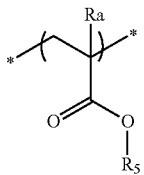

(IV)

In general formula (IV), $R_5$ represents a hydrocarbon group having at least one cyclic structure in which neither a hydroxyl group nor a cyano group is contained.

Ra represents a hydrogen atom, an alkyl group or a group of the formula —CH₂—O—Ra₂ in which Ra₂ represents a hydrogen atom, an alkyl group or an acyl group. Ra preferably represents a hydrogen atom, a methyl group, a trifluoromethyl group, a hydroxymethyl group or the like, more preferably a hydrogen atom and a methyl group.

The cyclic structures contained in $R_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group are more preferred.

The polycyclic hydrocarbon groups include ring-assembly hydrocarbon groups and crosslinked-ring hydrocarbon groups. Examples of the ring-assembly hydrocarbon groups include a bicyclohexyl group, a perhydronaphthalene group and the like. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[5.2.1.0²,⁶]decane and tricyclo[4.3.1.1²,⁵]undecane rings; and tetracyclic hydrocarbon rings, such as tetracyclo[4.4.0.1²,⁵.1⁷,¹⁰]dodecane and perhydro-1,4-methano-5,8-methanonaphthalene rings. Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenarene rings.

As preferred crosslinked-ring hydrocarbon rings, there can be mentioned, for example, a norbornyl group, an adamantyl group, a bicyclooctanyl group and a tricyclo[5,2,1,0²,⁶]decanyl group. As more preferred crosslinked-ring hydrocarbon rings, there can be mentioned a norbornyl group and an adamantyl group.

These alicyclic hydrocarbon groups may have substituents. As preferred substituents, there can be mentioned, for example, a halogen atom, an alkyl group, a hydroxyl group protected by a protective group and an amino group protected by a protective group. The halogen atom is preferably a bromine, chlorine or fluorine atom, and the alkyl group is preferably a methyl, ethyl, butyl or t-butyl group. The alkyl group may further have a substituent. As the optional further substituent, there can be mentioned a halogen atom, an alkyl group, a hydroxyl group protected by a protective group or an amino group protected by a protective group.

As the protective group, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably a 1-ethoxyethyl or 1-methyl-1-methoxyethyl group. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

The content ratio of any of the repeating units that have a structure of alicyclic hydrocarbon having no polar group, exhibiting no acid decomposability, based on all the repeating units of resin (B), is preferably in the range of 0 to 40 mol %, more preferably 0 to 20 mol %.

Specific examples of the repeating units that have a structure of alicyclic hydrocarbon having no polar group, exhibiting no acid decomposability will be shown below, which however in no way limit the scope of the present invention. In the formulae, Ra represents H, $CH_3$, $CH_2OH$ or $CF_3$.

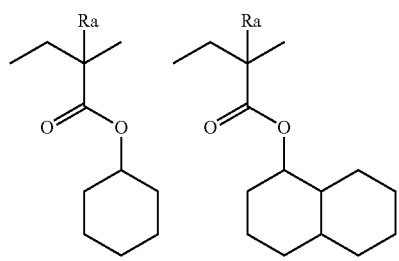

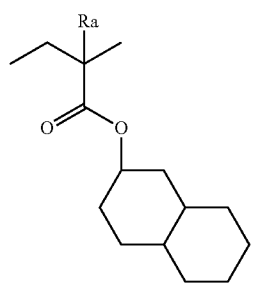

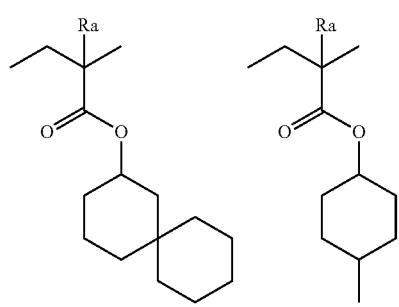

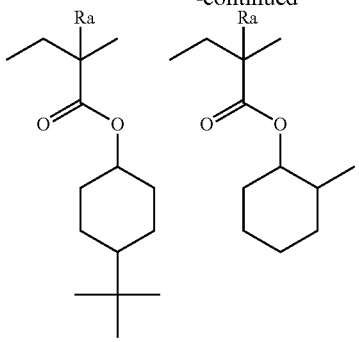

-continued

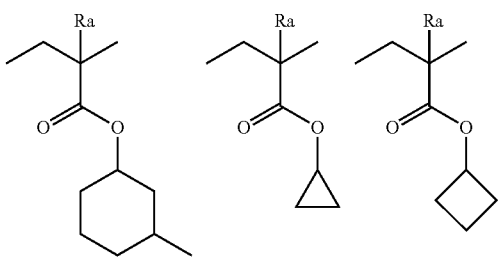

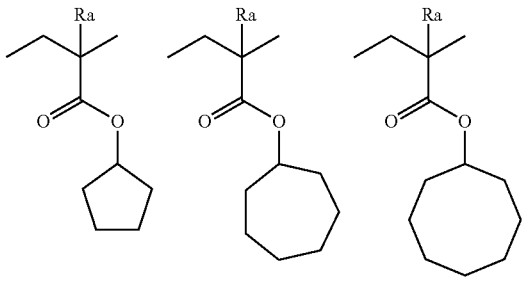

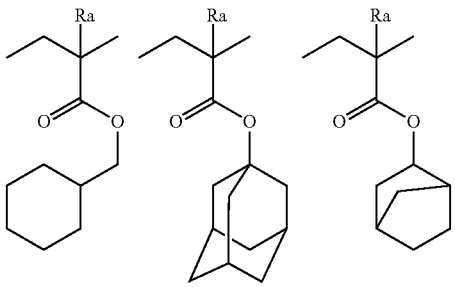

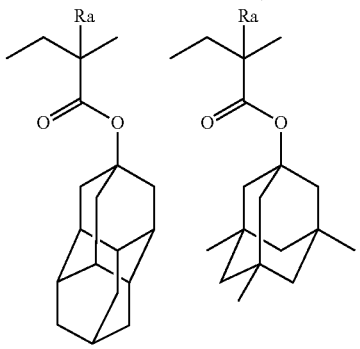

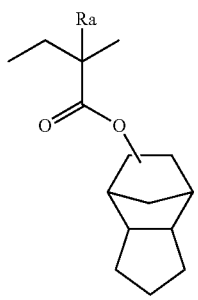

Resin (B) may have, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which however are nonlimiting.

The use of such repeating structural units would enable fine regulation of the required properties of resin (A), especially:
(1) solubility in applied solvents,
(2) film forming easiness (glass transition point),
(3) alkali developability,
(4) film thinning (selections of hydrophilicity/hydrophobicity and alkali-soluble group),
(5) adhesion of unexposed area to substrate,
(6) dry etching resistance, etc.

As appropriate monomers, there can be mentioned, for example, a compound having an unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

The molar ratios of individual repeating structural units contained in resin (B) are appropriately determined from the viewpoint of regulation of not only the dry etching resistance of the resist but also the standard developer adaptability, substrate adhesion, resist profile and generally required properties of the resist such as the resolving power, heat resistance and sensitivity.

When the composition of the present invention is one for ArF exposure, it is preferred for resin (B) to have no aromatic group and to have an alicyclic hydrocarbon structure of a single ring or multiple rings from the viewpoint of transparency to ArF beams.

From the viewpoint of the compatibility with hydrophobicresin (C) to be described hereinafter, it is preferred for resin (B) to contain neither a fluorine atom nor a silicon atom.

In resin (B), preferably, all the repeating units consist of (meth)acrylate repeating units. In that instance, use can be made of any of a resin wherein all the repeating units consist of methacrylate repeating units, a resin wherein all the repeating units consist of acrylate repeating units and a resin wherein all the repeating units consist of methacrylate repeating units and acrylate repeating units. However, it is preferred for the acrylate repeating units to account for 50 mol % or less of all the repeating units. It is more preferred to employ a copolymer containing 20 to 50 mol % of (meth)acrylate repeating units having an acid-decomposable group, 20 to 50 mol % of (meth)acrylate repeating units having a lactone group, 5 to 30 mol % of (meth)acrylate repeating units having an alicyclic hydrocarbon structure substituted with a hydroxyl group or a cyano group and 0 to 20 mol % of other (meth)acrylate repeating units.

In the event of exposing the actinic-ray- or radiation-sensitive resin composition of the present invention to KrF excimer laser beams, electron beams, X-rays or high-energy light rays of wavelength 50 nm or less (EUV, etc.), it is preferred for resin (B) to further have hydroxystyrene repeating units. More preferably, resin (B) has hydroxystyrene repeating units, hydroxystyrene repeating units protected by an acid-decomposable group and acid-decomposable repeating units of a (meth)acrylic acid tertiary alkyl ester, etc.

As preferred hydroxystyrene repeating units having an acid-decomposable group, there can be mentioned, for example, repeating units derived from t-butoxycarbonyloxystyrene, a 1-alkoxyethoxystyrene and a (meth)acrylic acid tertiary alkyl ester. Repeating units derived from a 2-alkyl-2-adamantyl(meth)acrylate and a dialkyl(1-adamantyl)methyl (meth)acrylate are more preferred.

Resin (B) of the present invention can be synthesized by conventional techniques (for example, radical polymerization). As general synthetic methods, there can be mentioned, for example, a batch polymerization method in which a monomer species and an initiator are dissolved in a solvent and heated so as to accomplish polymerization and a dropping polymerization method in which a solution of monomer species and initiator is added by dropping to a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or the solvent capable of dissolving the composition of the present invention, such as propylene glycol monomethyl ether acetate, propylene glycol monomethyl ether or cyclohexanone, to be described hereinafter. It is preferred to perform the polymerization with the use of the same solvent as employed in the actinic-ray- or radiation-sensitive resin composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis(2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10° to 150° C., preferably 30° to 120° C. and more preferably 60° to 100° C.

The weight average molecular weight of resin (B) in terms of polystyrene molecular weight as measured by GPC is preferably in the range of 1000 to 200,000, more preferably 2000 to 20,000, still more preferably 3000 to 15,000 and further preferably 5000 to 13,000. The regulation of the weight average molecular weight to 1000 to 200,000 would prevent deteriorations of heat resistance and dry etching resistance and also prevent deterioration of developability and increase of viscosity leading to poor film forming property.

Use is made of the resin whose dispersity (molecular weight distribution) is generally in the range of 1 to 3, preferably 1 to 2.6, more preferably 1 to 2 and most preferably 1.4 to 2.0. The lower the molecular weight distribution, the more excellent the resolving power and resist profile and the smoother the side wall of the resist pattern to thereby attain an excellence in roughness.

In the present invention, the content ratio of resin (B) based on the total solid content of the whole composition is preferably in the range of 30 to 99 mass %, more preferably 60 to 95 mass %.

In the present invention, the resins (B) may be used either individually or in combination.

(C) Hydrophobic Resin

In the exposure of the film of the composition of the present invention via the liquid immersion medium, a hydrophobic resin (HR) may be further added according to necessity. This would bring about uneven localization of the hydrophobic resin (HR) on the surface layer of the film. When the liquid immersion medium is water, there would be attained an improvement of receding contact angle on the surface of the film with reference to water upon formation of the film, and accordingly an enhancement of the liquid immersion water tracking property. Although the hydrophobic resin (HR) is not particularly limited as long as an improvement of receding contact angle on the surface is realized by the addition thereof, it is preferred to employ a resin having at least either a fluorine atom or a silicon atom. The receding contact angle of the film is preferably in the range of 60° to 90°, more preferably 70° or higher. The amount of resin added can be appropriately regulated so that the receding contact angle of the film falls within the above range. Although the hydrophobic resin (HR) is unevenly localized on the interface as aforementioned, differing from the surfactant, the hydrophobic resin does not necessarily have to have a hydrophilic group in its molecule and does not need to contribute toward uniform mixing of polar/nonpolar substances.

The receding contact angle refers to a contact angle determined when the contact line at a droplet-substrate interface draws back. It is generally known that the receding contact angle is useful in the simulation of droplet mobility in a dynamic condition. In a simple definition, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the resist film in dynamic condition is important, and it is required for the resist to be capable of tracking the high-speed scanning of the exposure head without leaving any droplets.

The fluorine atom or silicon atom of the hydrophobic resin (HR) may be present in the principal chain of the resin or may be a substituent on the side chain thereof.

The hydrophobic resin (HR) is preferably a resin having an alkyl group containing a fluorine atom, a cycloalkyl group containing a fluorine atom or an aryl group containing a fluorine atom as a partial structure containing a fluorine atom.

The alkyl group containing a fluorine atom (preferably having 1 to 10 carbon atoms, more preferably 1 to 4 carbon atoms) is a linear or branched alkyl group having at least one hydrogen atom thereof substituted with a fluorine atom. Further, other substituents may be possessed.

The cycloalkyl group containing a fluorine atom is a cycloalkyl group of a single ring or multiple rings having at least one hydrogen atom thereof substituted with a fluorine atom. Further, other substituents may be contained.

As the aryl group containing a fluorine atom, there can be mentioned one having at least one hydrogen atom of an aryl group, such as a phenyl or naphthyl group, substituted with a fluorine atom. Further, other substituents may be contained.

As preferred alkyl groups containing a fluorine atom, cycloalkyl groups containing a fluorine atom and aryl groups containing a fluorine atom, there can be mentioned groups of the following general formulae (F2) to (F4), which however in no way limit the scope of the present invention.

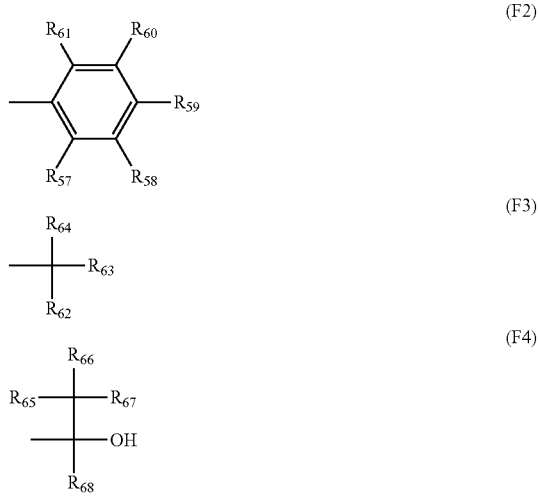

In the general formulae (F2) to (F4), each of $R_{57}$ to $R_{68}$ independently represents a hydrogen atom, a fluorine atom or an alkyl group, provided that at least one of each of $R_{57}$-$R_{61}$, $R_{62}$-$R_{64}$ and $R_{65}$-$R_{68}$ represents a fluorine atom or an alkyl group (preferably having 1 to 4 carbon atoms) having at least one hydrogen atom thereof substituted with a fluorine atom. It is preferred that all of $R_{57}$-$R_{61}$ and $R_{65}$-$R_{67}$ represent fluorine atoms. Each of $R_{62}$, $R_{63}$ and $R_{68}$ preferably represents an alkyl group (especially having 1 to 4 carbon atoms) having at least one hydrogen atom thereof substituted with a fluorine atom, more preferably a perfluoroalkyl group having 1 to 4 carbon atoms. $R_{62}$ and $R_{63}$ may be bonded with each other to thereby form a ring.

Specific examples of the groups of the general formula (F2) include a p-fluorophenyl group, a pentafluorophenyl group, a 3,5-di(trifluoromethyl)phenyl group and the like.

Specific examples of the groups of the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2, 3,3-tetrafluorocyclobutyl group, a perfluorocyclohexyl group and the like. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of the general formula (F4) include —C(CF$_3$)$_2$OH, —C(C$_2$F$_5$)$_2$OH, —C(CF$_3$)(CF$_3$)OH, —CH(CF$_3$)OH and the like. —C(CF$_3$)$_2$OH is preferred.

Specific examples of the repeating units having a fluorine atom will be shown below, which however in no way limit the scope of the present invention.

In the specific examples, $X_1$ represents a hydrogen atom, —CH$_3$, —F or —CF$_3$. $X_2$ represents —F or —CF$_3$.

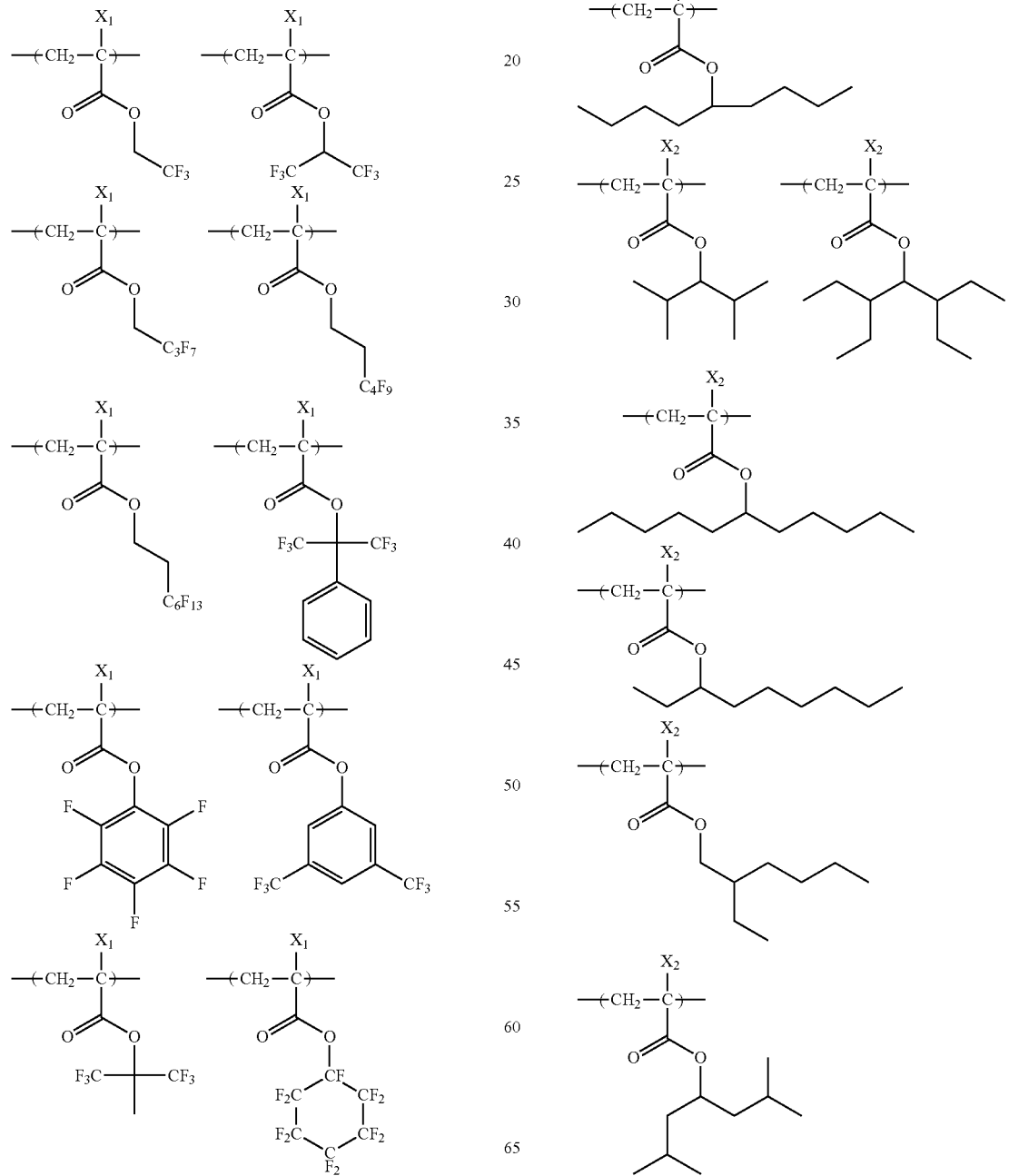

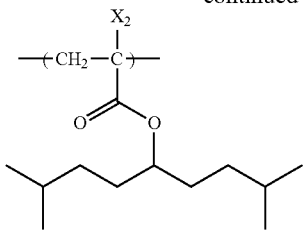

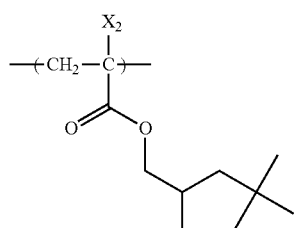

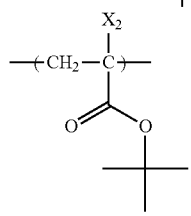

The hydrophobic resin (HR) may contain a silicon atom. It is preferred for the resin to have an alkylsilyl structure (preferably a trialkylsilyl group) or a cyclosiloxane structure as a partial structure having a silicon atom.

As the alkylsilyl structure or cyclosiloxane structure, there can be mentioned, for example, any of the groups of the following general formulae (CS-1) to (CS-3) or the like.

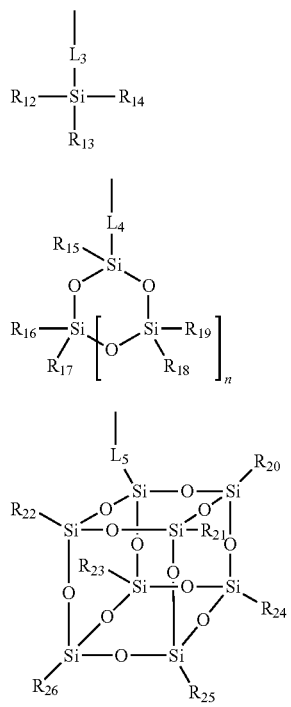

In the general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one or a combination of two or more groups selected from the group consisting of an alkylene group, a phenylene group, an ether group, a thioether group, a carbonyl group, an ester group, an amido group, a urethane group and a urea group.

In the formulae, n is an integer of 1 to 5.

Specific examples of the repeating units having the groups of the general formulae (CS-1) to (CS-3) will be shown below, which however in no way limit the scope of the present invention. Further, as the specific examples, there can be mentioned the repeating units having silicon atoms contained in the resins (HR-1) to (HR-65) below. In the specific examples, $X_1$ represents a hydrogen atom, —$CH_3$, —F or —$CF_3$.

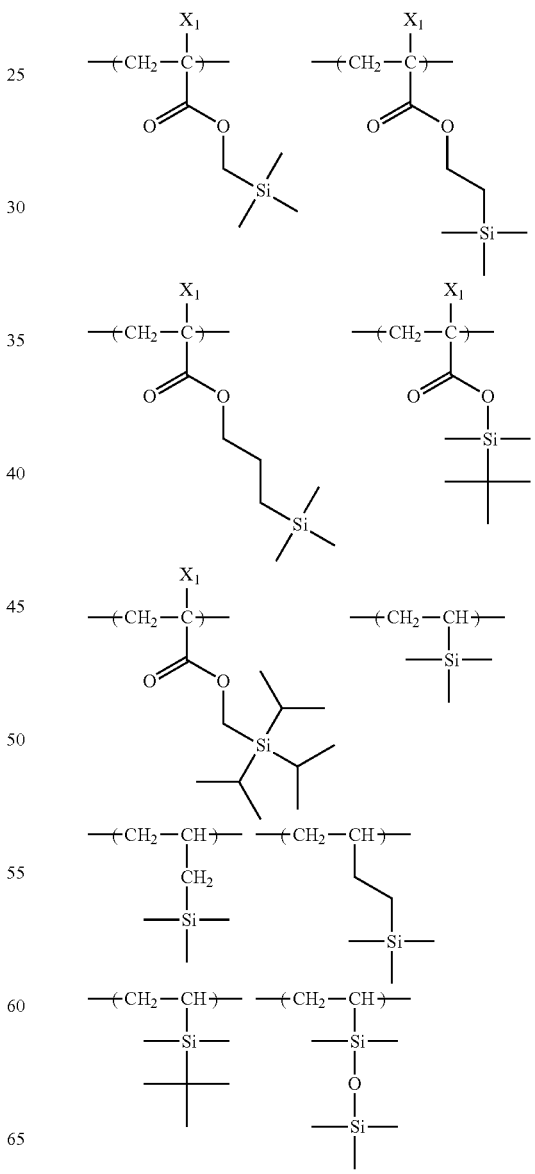

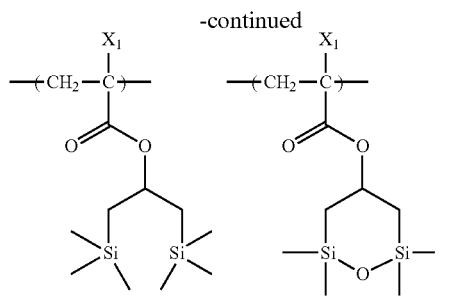
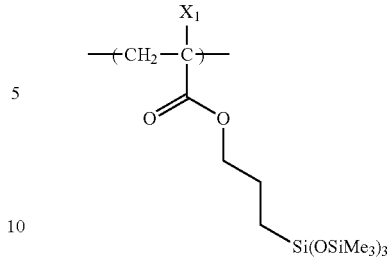
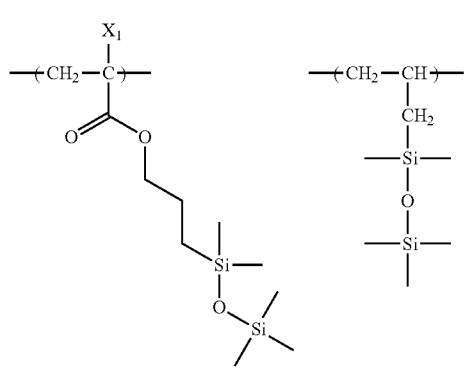
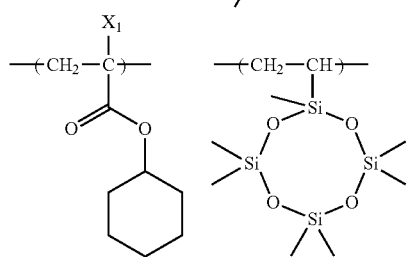
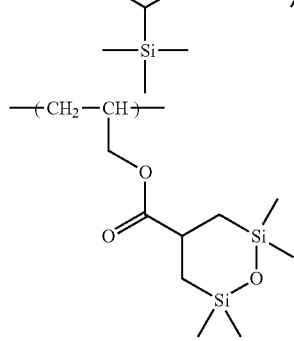
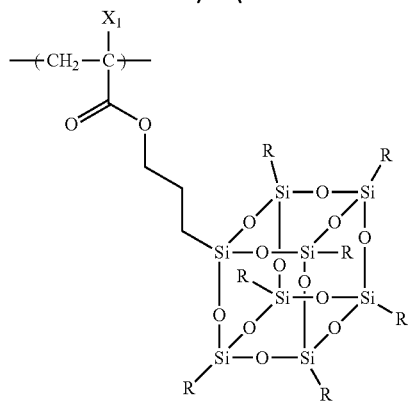

R = CH₃, C₂H₅, C₃H₇, C₄H₉

Moreover, the hydrophobic resin (HR) may have at least one group selected from among the following groups (x) to (z):

(x) an alkali soluble group,
(y) a group that is decomposed by the action of an alkali developer, resulting in an increase of solubility in the alkali developer, and
(z) a group that is decomposed by the action of an acid.

As the alkali soluble group (x), there can be mentioned a phenolic hydroxyl group, a carboxylate group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali soluble groups, there can be mentioned a fluoroalcohol group (preferably hexafluoroisopropanol), a sulfonimido group and a bis(carbonyl)methylene group.

As the repeating unit having an alkali soluble group (x), preferred use is made of any of a repeating unit resulting from direct bonding of an alkali soluble group to the principal chain of a resin like a repeating unit of acrylic acid or methacrylic acid, a repeating unit resulting from bonding, via a connecting group, of an alkali soluble group to the principal chain of a resin and a repeating unit resulting from polymerization with the use of a chain transfer agent or polymerization initiator having an alkali soluble group to thereby introduce the same in a polymer chain terminal.

The content of repeating units having an alkali soluble group (x) is preferably in the range of 1 to 50 mol %, more preferably 3 to 35 mol % and still more preferably 5 to 20 mol % based on all the repeating units of the polymer.

Specific examples of the repeating units having an alkali soluble group (x) will be shown below, which however in no way limit the scope of the present invention.

In the formulae, Rx represents H, CH₃, CF₃ or CH₂OH.

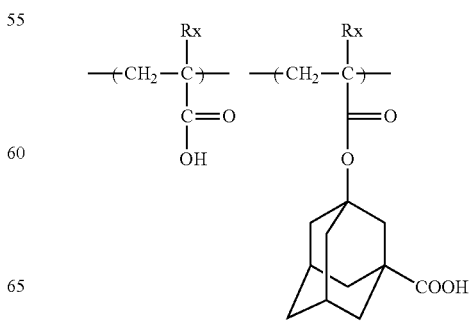

-continued
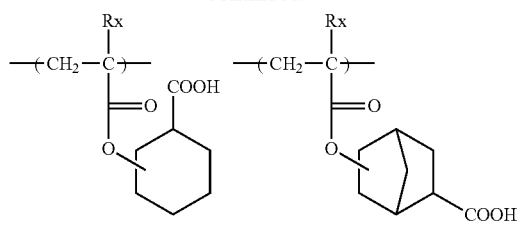
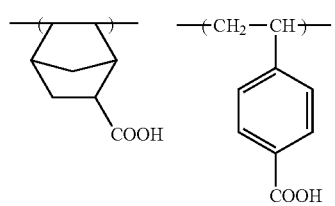
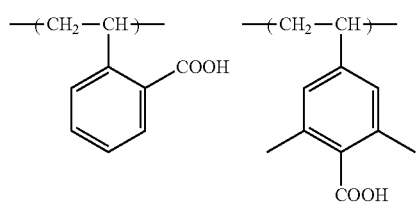
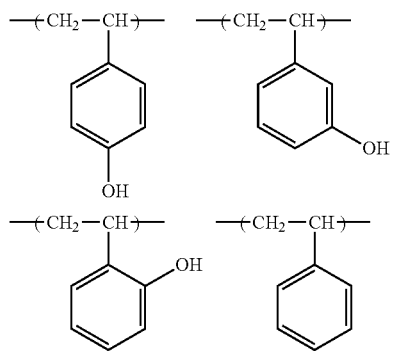
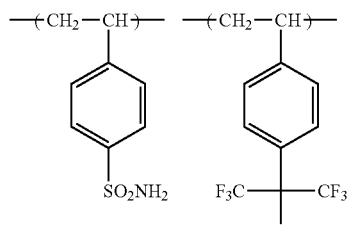
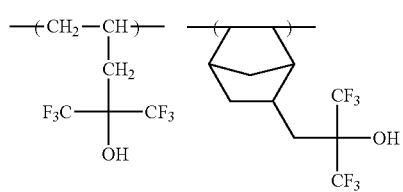
-continued
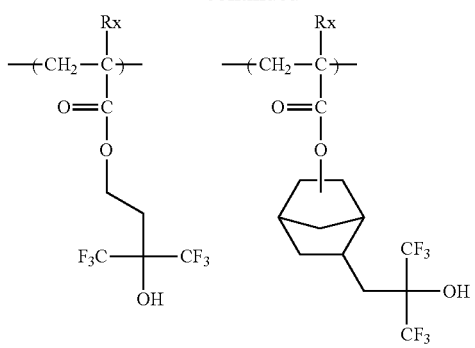
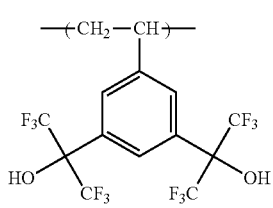
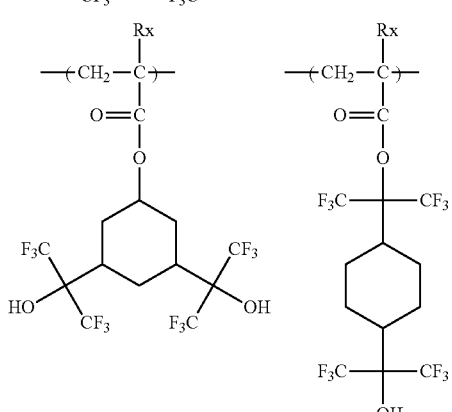
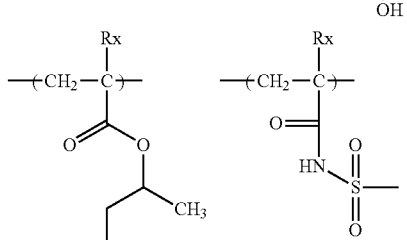
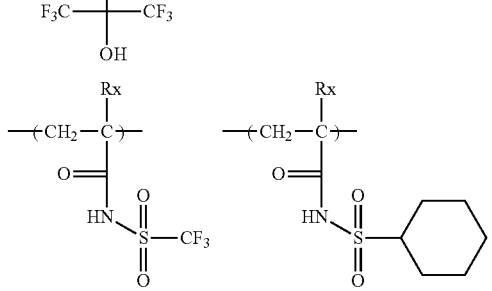
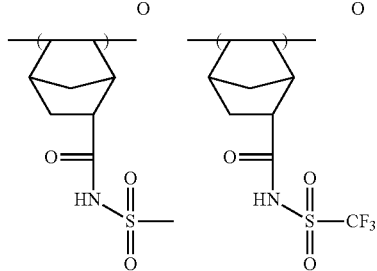

-continued

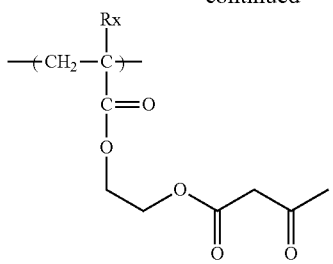

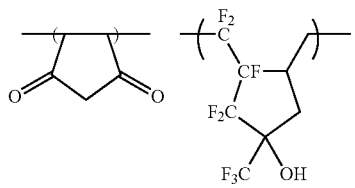

As the group (y) that is decomposed by the action of an alkali developer, resulting in an increase of solubility in the alkali developer, there can be mentioned, for example, a group having a lactone structure, an acid anhydride group, an acid imide group or the like. A group having a lactone structure is preferred.

As the repeating unit having a group (y) that is decomposed by the action of an alkali developer, resulting in an increase of solubility in the alkali developer, preferred use is made of both of a repeating unit resulting from bonding of a group (y) that is decomposed by the action of an alkali developer, resulting in an increase of solubility in the alkali developer, to the principal chain of a resin such as a repeating unit of acrylic ester or methacrylic ester, and a repeating unit resulting from polymerization with the use of a chain transfer agent or polymerization initiator having a group (y) resulting in an increase of solubility in an alkali developer to thereby introduce the same in a polymer chain terminal.

The content ratio of repeating units having a group (y) resulting in an increase of solubility in an alkali developer is preferably in the range of 1 to 40 mol %, more preferably 3 to 30 mol % and still more preferably 5 to 15 mol % based on all the repeating units of the polymer.

As specific examples of the repeating units having a group (y) resulting in an increase of solubility in an alkali developer, there can be mentioned those similar to the repeating units having a lactone structure set forth with respect to the resins as the component (B).

As the repeating unit having a group (z) that is decomposed by the action of an acid in the hydrophobic resin (HR), there can be mentioned those similar to the repeating units having an acid decomposable group set forth with respect to the resin (A). The content of repeating units having a group (z) that is decomposed by the action of an acid in the hydrophobic resin (HR) is preferably in the range of 1 to 80 mol %, more preferably 10 to 80 mol % and still more preferably 20 to 60 mol % based on all the repeating units of the polymer.

The hydrophobic resin (HR) may further have any of the repeating units of the following general formula (III).

In general formula (III), $R_{c31}$ represents a hydrogen atom, an alkyl group, an alkyl group substituted with a fluorine atom, a cyano group or —$CH_2$—O—$Rac_2$ group, wherein $Rac_2$ represents a hydrogen atom, an alkyl group or an acyl group. $R_{c31}$ is preferably a hydrogen atom, a methyl group, a hydroxymethyl group or a trifluoromethyl group, especially preferably a hydrogen atom or a methyl group.

$R_{c32}$ represents a group having any of an alkyl group, a cycloalkyl group, an alkenyl group and a cycloalkenyl group. These groups may optionally be substituted with a fluorine atom or a silicon atom.

$L_{c3}$ represents a single bond or a bivalent connecting group.

In general formula (III), the alkyl group represented by $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

Preferably, $R_{c32}$ represents an unsubstituted alkyl group or an alkyl group substituted with a fluorine atom.

The bivalent connecting group represented by $L_{c3}$ is preferably an alkylene group (preferably having 1 to 5 carbon atoms), an oxy group, a phenylene group or an ester bond (group of the formula —COO—).

Further, the hydrophobic resin (HR) may preferably have any of the repeating units of general formula (CII-AB) below.

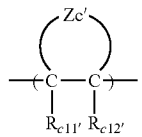

In general formula (CII-AB), each of $R_{c11'}$ and $R_{c12'}$ independently represents a hydrogen atom, a cyano group, a halogen atom or an alkyl group.

Zc' represents an atomic group for forming an alicyclic structure which contains two bonded carbon atoms (C—C).

Specific examples of the repeating units of general formula (III) and general formula (CII-AB) will be shown below, which however in no way limit the scope of the present invention. In the formulae, Ra represents H, $CH_3$, $CH_2OH$, $CF_3$ or CN.

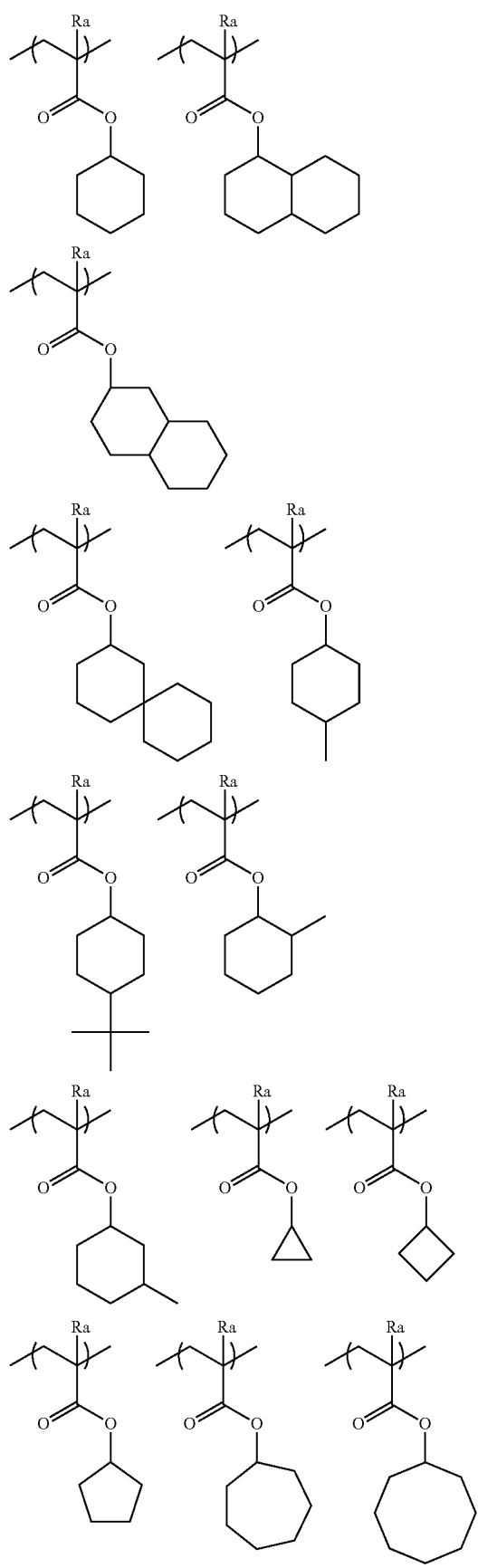
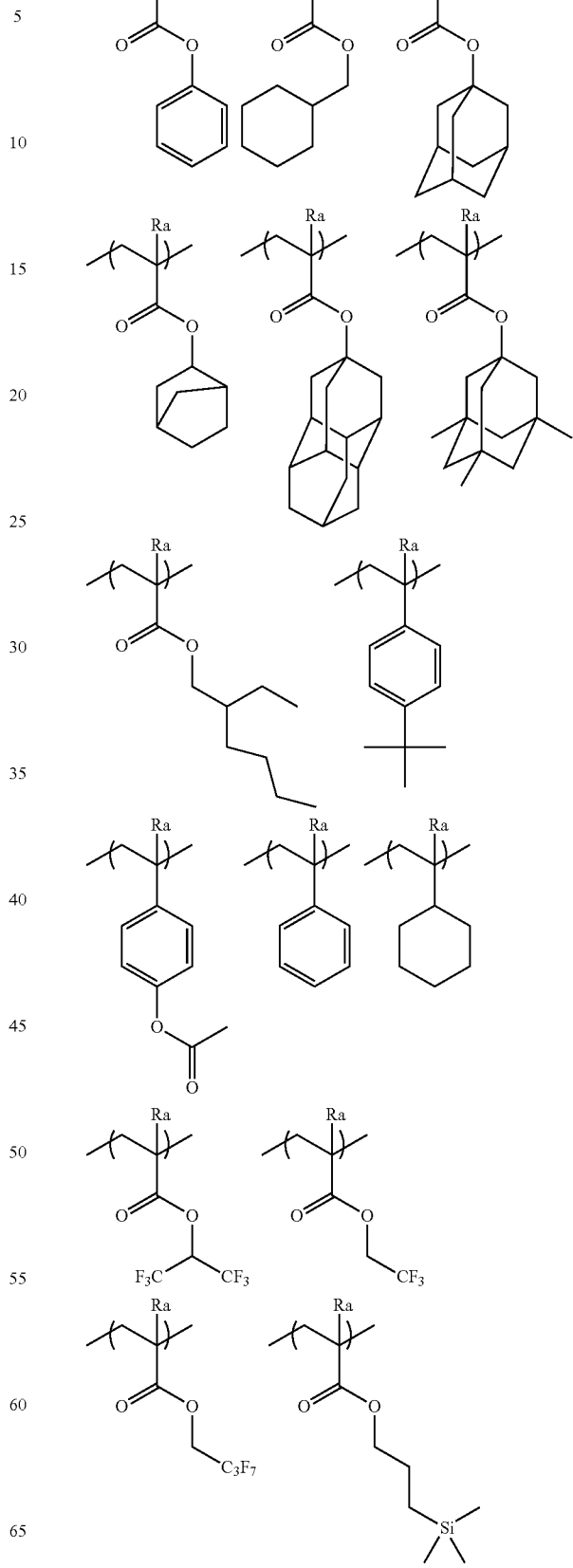
-continued

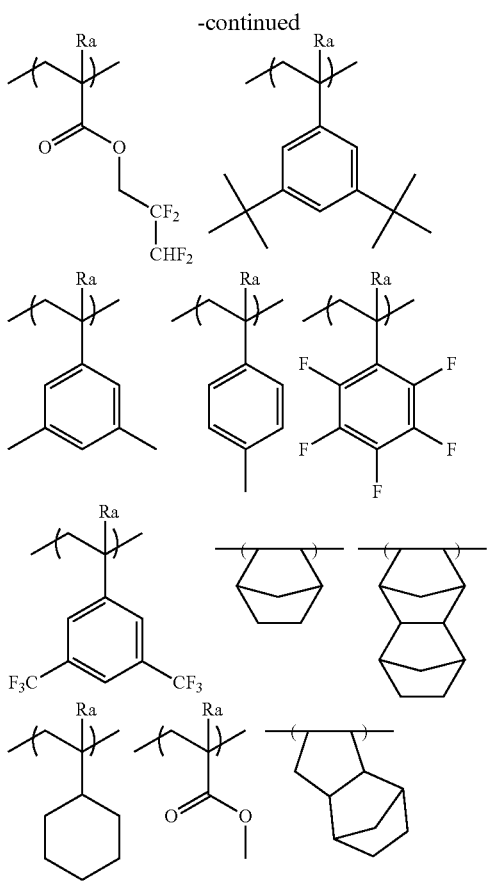

When the hydrophobic resin (HR) has a fluorine atom, the content of fluorine atom(s) is preferably in the range of 5 to 80 mass %, more preferably 10 to 80 mass %, based on the molecular weight of the hydrophobic resin (HR). The repeating unit containing a fluorine atom preferably exists in the hydrophobic resin (HR) in an amount of 10 to 100 mass %, more preferably 30 to 100 mass %.

When the hydrophobic resin (HR) has a silicon atom, the content of silicon atom(s) is preferably in the range of 2 to 50 mass %, more preferably 2 to 30 mass %, based on the molecular weight of the hydrophobic resin (HR). The repeating unit containing a silicon atom preferably exists in the hydrophobic resin (HR) in an amount of 10 to 100 mass %, more preferably 20 to 100 mass %.

The weight average molecular weight of the hydrophobic resin (HR) in terms of standard polystyrene molecular weight is preferably in the range of 1000 to 100,000, more preferably 1000 to 50,000 and still more preferably 2000 to 15,000.

The content of the hydrophobic resin (HR) in the composition is in the range or 0.01 to 10 mass %, more preferably 0.05 to 8 mass % and still more preferably 0.1 to 5 mass % based on the total solid of the composition of the present invention.

Impurities, such as metals, should naturally be of low quantity in the hydrophobic resin (HR), as for the resin as the component (B). The content of residual monomers and oligomer components is preferably 0 to 10 mass %, more preferably 0 to 5 mass % and still more preferably 0 to 1 mass %. Accordingly, there can be obtained a resist being free from a change of in-liquid foreign matter, sensitivity, etc. over time. From the viewpoint of resolving power, resist profile, side wall of resist pattern, roughness, etc., the molecular weight distribution (Mw/Mn, also referred to as the degree of dispersal) thereof is preferably in the range of 1 to 5, more preferably 1 to 3 and still more preferably 1 to 2.

A variety of commercially available products can be used as the hydrophobic resin (HR), and also the resin can be synthesized in accordance with conventional methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a hot solvent over a period of 1 to 10 hours, and the like. The dropping polymerization method is preferred. As a reaction solvent, there can be mentioned, for example, an ether such as tetrahydrofuran, 1,4-dioxane or diisopropyl ether, a ketone such as methyl ethyl ketone or methyl isobutyl ketone, an ester solvent such as ethyl acetate, an amide solvent such as dimethylformamide or dimethylacetamide, or the aforementioned solvent capable of dissolving the composition of the present invention, such as propylene glycol monomethyl ether acetate, propylene glycol monomethyl ether or cyclohexanone. Preferably, the polymerization is carried out with the use of the same solvent as that used in the photosensitive composition of the present invention. This would inhibit any particle generation during storage.

The polymerization reaction is preferably carried out in an atmosphere consisting of an inert gas, such as nitrogen or argon. In the initiation of polymerization, a commercially available radical initiator (azo initiator, peroxide, etc.) is used as the polymerization initiator. Among the radical initiators, an azo initiator is preferred, and azo initiators having an ester group, a cyano group and a carboxyl group are more preferred. As specific preferred initiators, there can be mentioned azobisisobutyronitrile, azobisdimethylvaleronitrile, dimethyl 2,2'-azobis(2-methylpropionate) and the like. The reaction concentration is in the range of 5 to 50 mass %, preferably 30 to 50 mass %. The reaction temperature is generally in the range of 10° to 150° C., preferably 30° to 120° C. and more preferably 60° to 100° C.

After the completion of the reaction, the mixture is allowed to stand still to cool to room temperature and purified. In the purification, use is made of routine methods, such as a liquid-liquid extraction method in which residual monomers and oligomer components are removed by water washing or by the use of a combination of appropriate solvents, a method of purification in solution form such as ultrafiltration capable of extraction removal of only components of a given molecular weight or below, a re-precipitation method in which a resin solution is dropped into a poor solvent to thereby coagulate the resin in the poor solvent and thus remove residual monomers, etc. and a method of purification in solid form such as washing of a resin slurry obtained by filtration with the use of a poor solvent. For example, the reaction solution is brought into contact with a solvent wherein the resin is poorly soluble or insoluble (poor solvent) amounting to 10 or less, preferably 10 to 5 times the volume of the reaction solution to thereby precipitate the resin as a solid.

The solvent for use in the operation of precipitation or re-precipitation from a polymer solution (precipitation or re-precipitation solvent) is not limited as long as the solvent is a poor solvent for the polymer. According to the type of polymer, use can be made of any one appropriately selected from among a hydrocarbon, a halogenated hydrocarbon, a nitro compound, an ether, a ketone, an ester, a carbonate, an alcohol, a carboxylic acid, water, a mixed solvent containing these solvents and the like. Of these, it is preferred to employ a solvent containing at least an alcohol (especially methanol or the like) or water as the precipitation or re-precipitation solvent.

The amount of precipitation or re-precipitation solvent used is generally in the range of 100 to 10,000 parts by mass, preferably 200 to 2000 parts by mass and more preferably 300 to 1000 parts by mass per 100 parts by mass of the polymer solution, according to intended efficiency, yield, etc.

The temperature at which the precipitation or re-precipitation is carried out is generally in the range of about 0° to 50° C., preferably about room temperature (for example, about 20° to 35° C.), according to efficiency and operation easiness. The operation of precipitation or re-precipitation can be carried out by a publicly known method, such as a batch or continuous method, with the use of a common mixing Vessel, such as an agitation vessel.

The polymer obtained by the precipitation or re-precipitation is generally subjected to common solid/liquid separation, such as filtration or centrifugal separation, and dried before use. The filtration is carried out with the use of a filter medium ensuring solvent resistance, preferably under pressure. The drying is performed at about 30° to 100° C., preferably about 30° to 50° C. at ordinary pressure or reduced pressure (preferably reduced pressure).

Alternatively, after the resin precipitation and separation, the obtained resin may be once more dissolved in a solvent and brought into contact with a solvent wherein the resin is poorly soluble or insoluble. Specifically, the method may include the steps of, after the completion of the radical polymerization reaction, bringing the polymer into contact with a solvent wherein the polymer is poorly soluble or insoluble to thereby precipitate a resin (step a), separating the resin from the solution (step b), re-dissolving the resin in a solvent to thereby obtain a resin solution (A) (step c), thereafter bringing the resin solution (A) into contact with a solvent wherein the resin is poorly soluble or insoluble amounting to less than 10 times (preferably 5 times or less) the volume of the resin solution (A) to thereby precipitate a resin solid (step d) and separating the precipitated resin (step e).

Specific examples of the hydrophobic resins (HR) will be shown below. The following Table 1 shows the molar ratio of individual repeating units (corresponding to individual repeating units in order from the left), weight average molecular weight and degree of dispersal with respect to each of the resins.

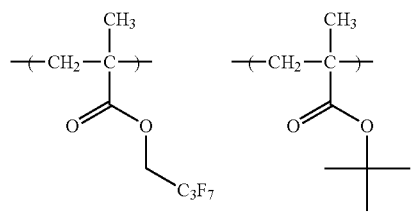

(HR-1)

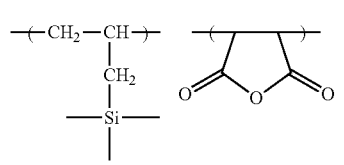

(HR-2)

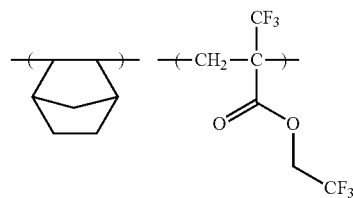

(HR-3)

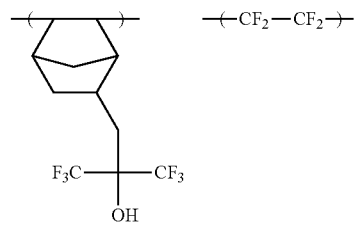

(HR-4)

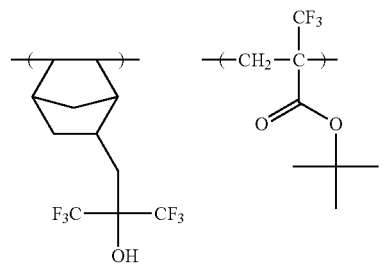

(HR-5)

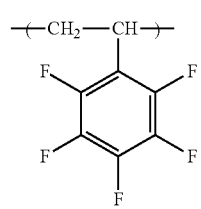

(HR-6)

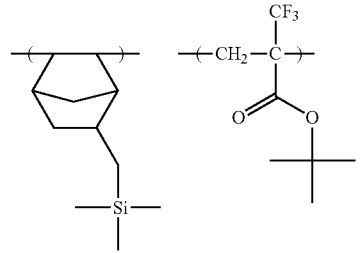

(HR-7)

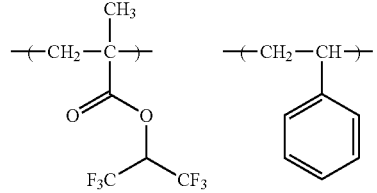

(HR-8)

(HR-9)
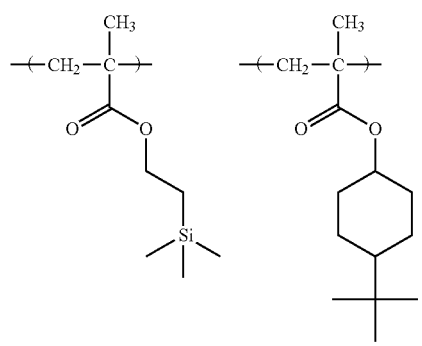
(HR-10)
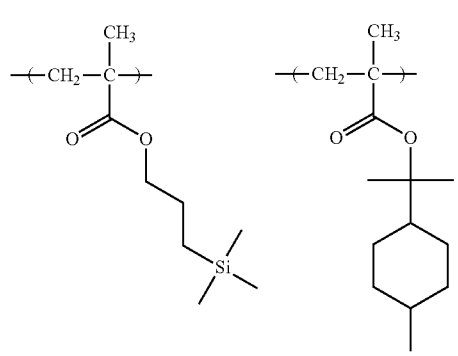
(HR-11)
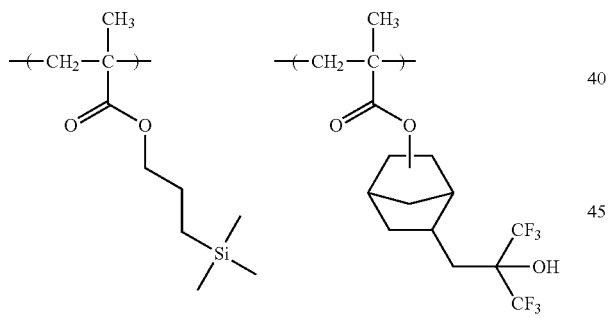
(HR-12)
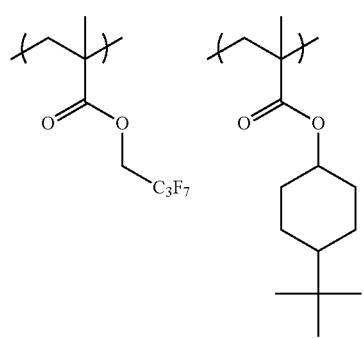
(HR-13)
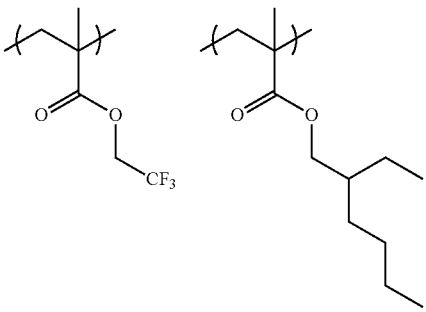
(HR-14)
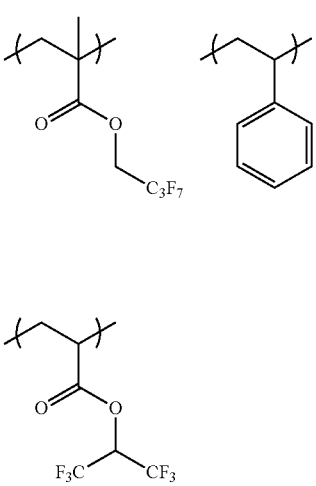
(HR-15)
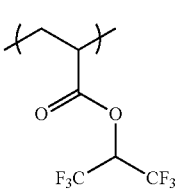
(HR-16)
(HR-17)
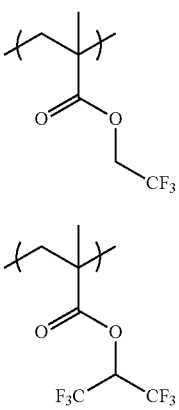
(HR-18)
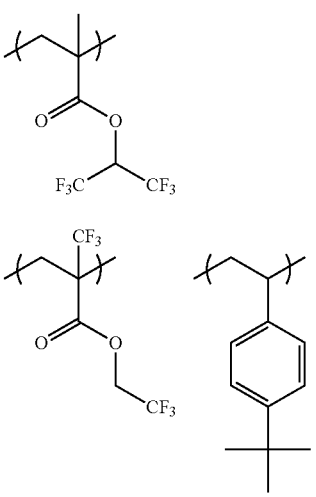

(HR-19) 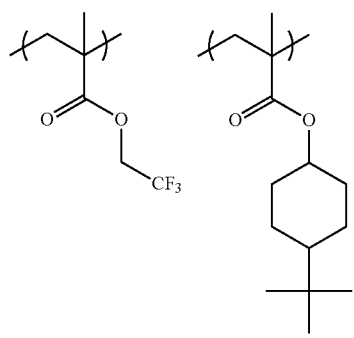
(HR-20) 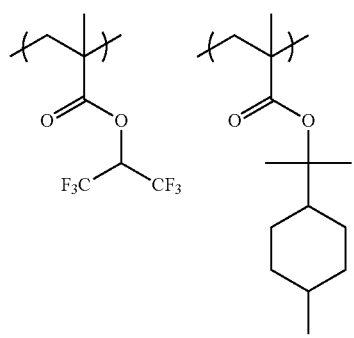
(HR-21) 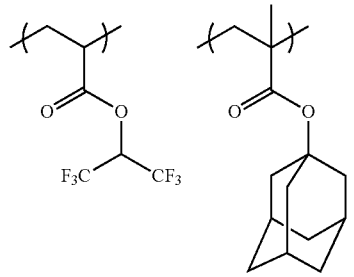
(HR-22) 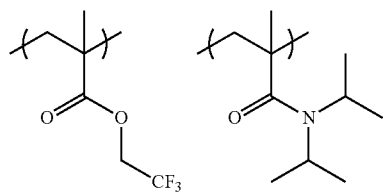
(HR-23) 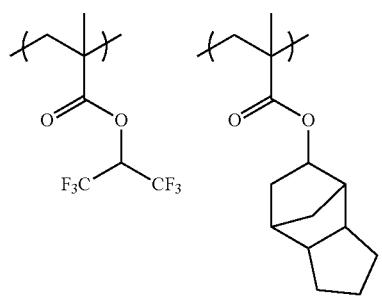
(HR-24) (HR-25) 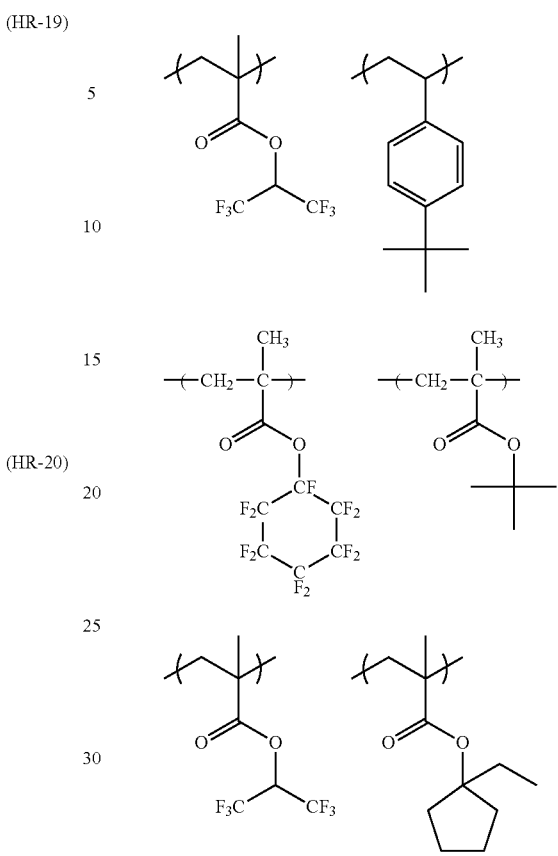
(HR-26) 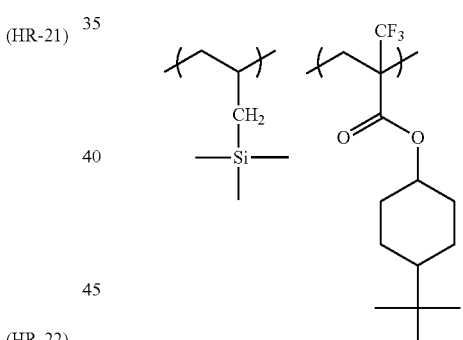
(HR-27) (HR-28) 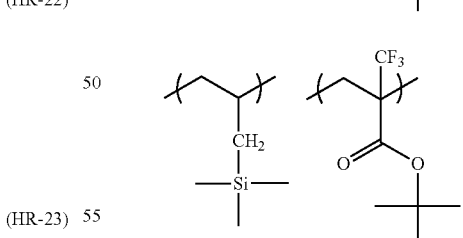
(HR-29) 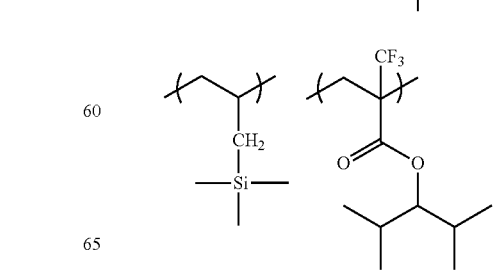

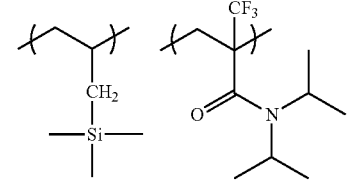
(HR-30)
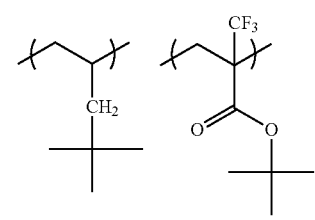
(HR-31)
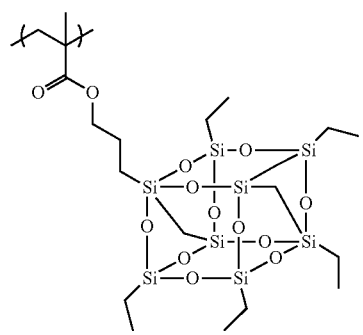
(HR-32)
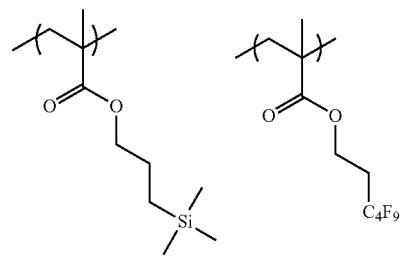
(HR-33)
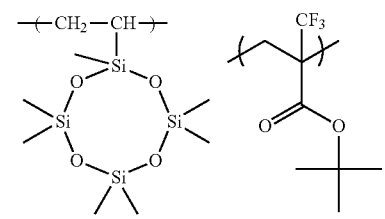
(HR-34)
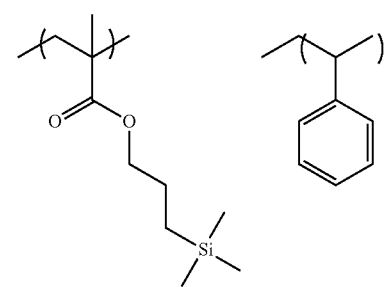
(HR-35)
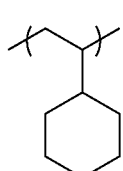
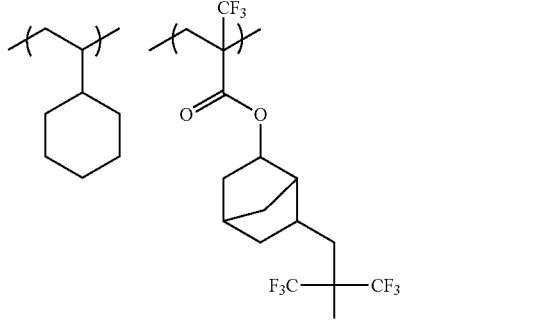
(HR-36)
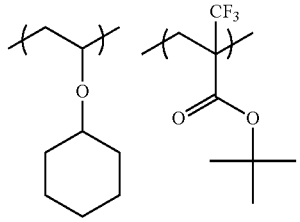
(HR-37)
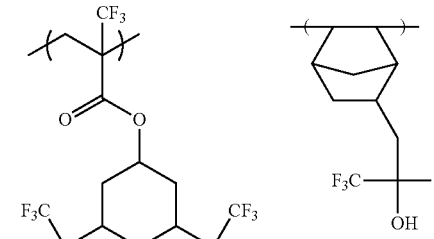
(HR-38)
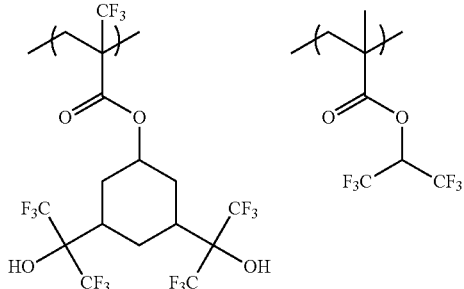
(HR-39)
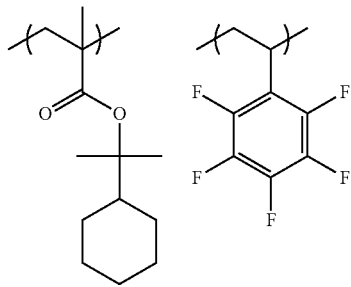
(HR-40)

(HR-41)
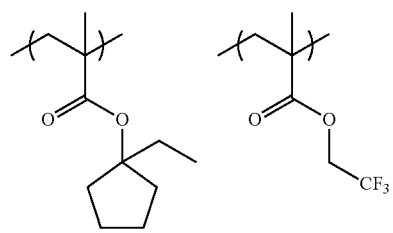
(HR-42)
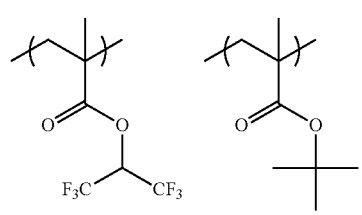
(HR-43)
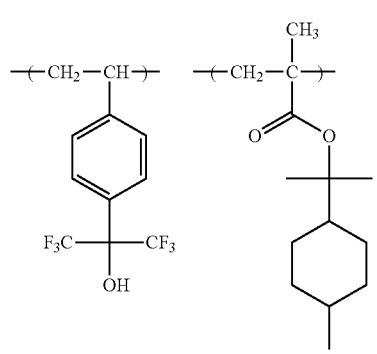
(HR-44)
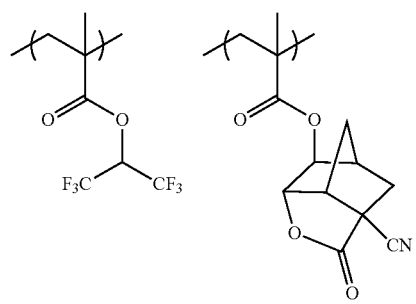
(HR-45)
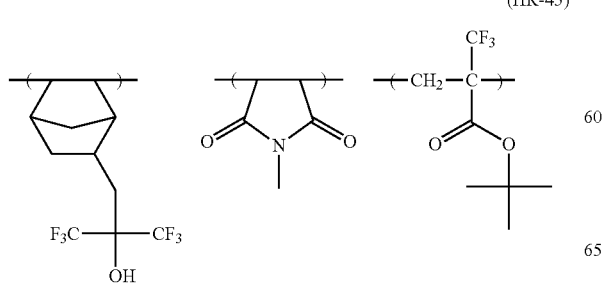
(HR-46)
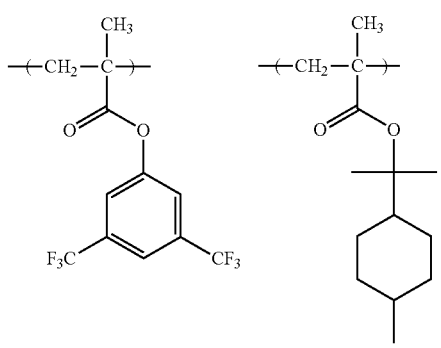
(HR-47)
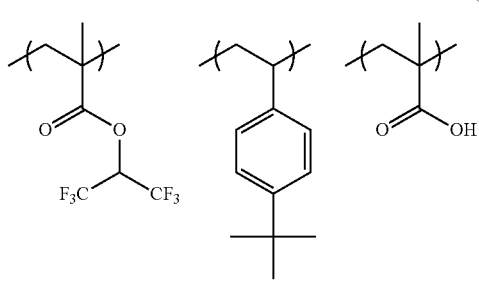
(HR-48)
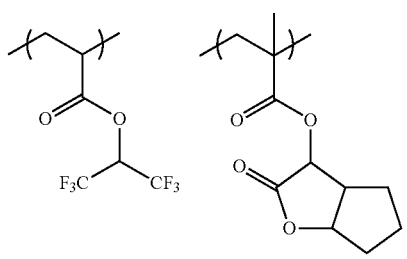
(HR-49)
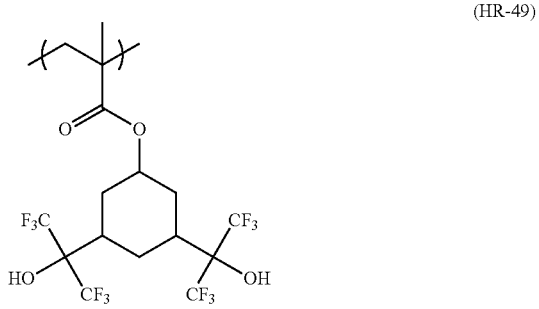
(HR-50)
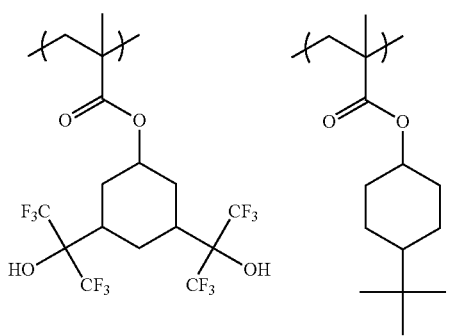

(HR-51)
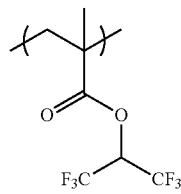 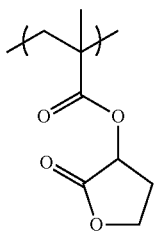 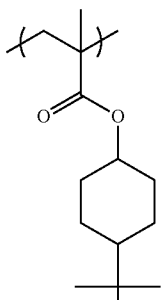
(HR-52)
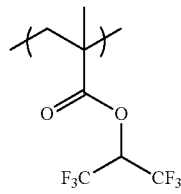 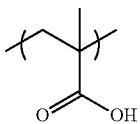
(HR-53)
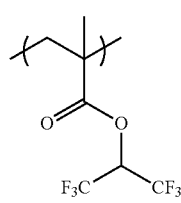 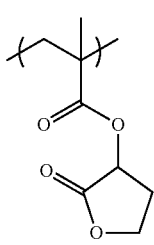 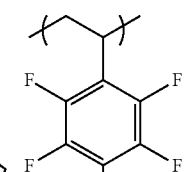
(HR-54)
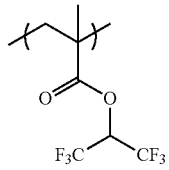 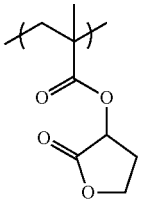 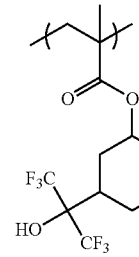
(HR-55)
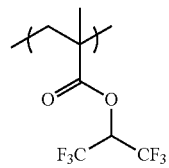 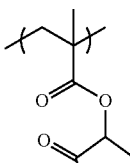 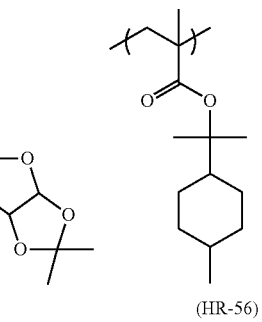
(HR-56)
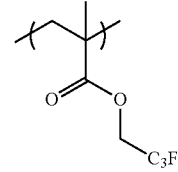 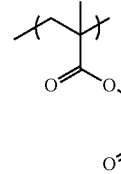
(HR-57)
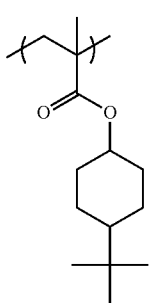 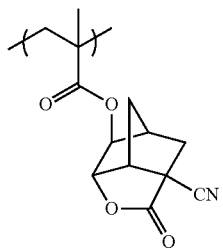
(HR-58)
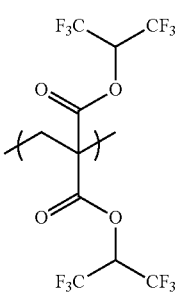 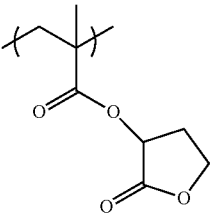
(HR-59)
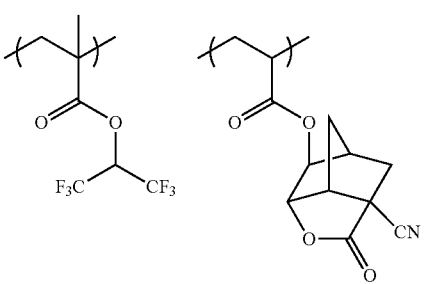
(HR-60)
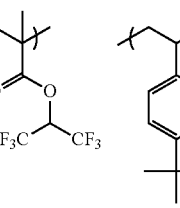 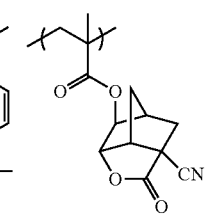
(HR-61)
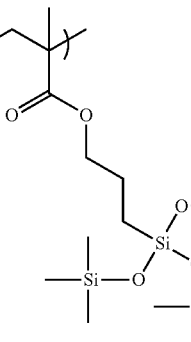 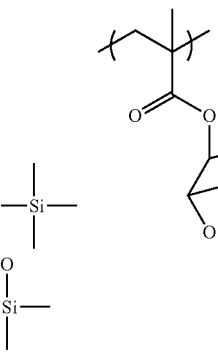

-continued

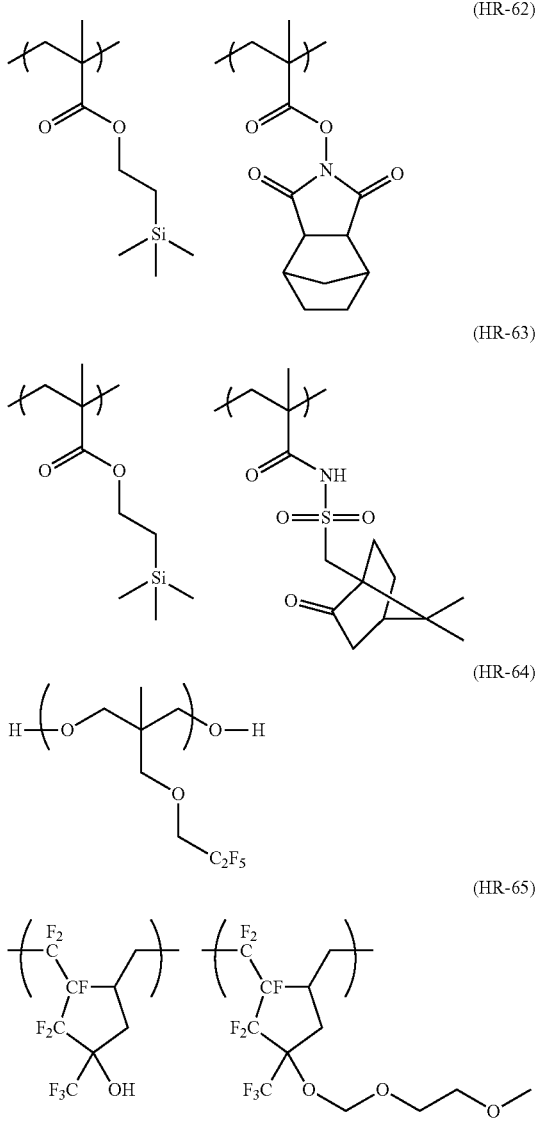

TABLE 1

| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |

TABLE 1-continued

| Resin | Composition | Mw | Mw/Mn |
|---|---|---|---|
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |

The film of the actinic-ray- or radiation-sensitive resin composition of the present invention may be exposed in the condition that the interstice between the film and a lens is filled with a liquid (immersion medium) whose refractive index is higher than that of air at the exposure to actinic rays or radiation (liquid-immersion exposure). This would bring about an enhancement of resolving power. Any liquid with a refractive index higher than that of air can be employed as the liquid immersion medium. Preferably, pure water is employed.

The liquid for liquid immersion for use in the liquid immersion exposure will now be described.

The liquid for liquid immersion preferably consists of a liquid being transparent in exposure wavelength whose temperature coefficient of refractive index is as low as possible so as to ensure minimization of any distortion of optical image projected on the film. Especially in the use of an ArF excimer laser (wavelength: 193 nm) as an exposure light source, however, it is more preferred to use water from not only the above viewpoints but also the viewpoints of easy procurement and easy handling.

Further, from the viewpoint of refractive index increase, use can be made of a medium of 1.5 or higher refractive index. Such a medium may be an aqueous solution or an organic solvent.

In the use of water as a liquid for liquid immersion, a slight proportion of additive (liquid) that would not dissolve the resist film on a wafer and would be negligible with respect to its influence on an optical coat for an under surface of lens element may be added in order to not only decrease the surface tension of water but also increase a surface activating power. The additive is preferably an aliphatic alcohol with a refractive index approximately equal to that of water, for example, methyl alcohol, ethyl alcohol, isopropyl alcohol or the like. The addition of an alcohol with a refractive index approximately equal to that of water is advantageous in that even when the alcohol component is evaporated from water to thereby cause a change of content concentration, the change of refractive index of the liquid as a whole can be minimized. On the other hand, when a substance being opaque in 193 nm rays or an impurity whose refractive index is greatly different from that of water is mixed therein, the mixing would invite a distortion of optical image projected on the resist film. Accordingly, it is preferred to use distilled water as the liquid immersion water. Furthermore, use may be made of pure water having been filtered through an ion exchange filter or the like.

Desirably, the electrical resistance of the water is 18.3 MQcm or higher, and the TOC (organic matter concentration) thereof is 20 ppb or below. Prior deaeration of the water is desired.

Raising the refractive index of the liquid for liquid immersion would enable an enhancement of lithography performance. From this viewpoint, an additive suitable for refractive index increase may be added to the water, or heavy water ($D_2O$) may be used in place of water.

In the exposure of the film of the composition of the present invention via the liquid immersion medium, a hydrophobic resin (HR) may be further added according to necessity. This would bring about uneven localization of the hydrophobic resin (HR) on the surface layer of the film. When the liquid immersion medium is water, there would be attained an improvement of receding contact angle on the surface of the film with reference to water upon formation of the film, and accordingly an enhancement of the liquid immersion water tracking property. By the addition of the hydrophobic resin (HR), the improvement of the receding contact angle on the surface of the film is realized. The receding contact angle of the film is preferably in the range of 60° to 90°, more preferably 70° or higher. Although the hydrophobic resin (HR) is unevenly localized on the interface as aforementioned, differing from the surfactant, the hydrophobic resin does not necessarily have to have a hydrophilic group in its molecule and does not need to contribute toward uniform mixing of polar/nonpolar substances.

The receding contact angle refers to a contact angle determined when the contact line at a droplet-substrate interface draws back. It is generally known that the receding contact angle is useful in the simulation of droplet mobility in a dynamic condition. In a simple definition, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the resist film in dynamic condition is important, and it is required for the resist to be capable of tracking the high-speed scanning of the exposure head without leaving any droplets.

For the prevention of direct contact of a film with a liquid for liquid immersion, a film that is highly insoluble in the liquid for liquid immersion (hereinafter also referred to as a "top coat") may be provided between the film from the composition of the present invention and the liquid for liquid immersion. The functions to be fulfilled by the top coat are applicability to an upper layer portion of the resist, transparency in radiation of especially 193 nm and being highly insoluble in the liquid for liquid immersion. Preferably, the top coat does not mix with the resist and is uniformly applicable to an upper layer of the resist.

From the viewpoint of 193 nm transparency, the top coat preferably consists of a polymer not abundantly containing an aromatic moiety. As such, there can be mentioned, for example, a hydrocarbon polymer, an acrylic ester polymer, polymethacrylic acid, polyacrylic acid, polyvinyl ether, a siliconized polymer, a fluoropolymer or the like. The aforementioned hydrophobic resins (HR) also find appropriate application in the top coat. From the viewpoint of contamination of an optical lens by leaching of impurities from the top coat into the liquid for liquid immersion, it is preferred to reduce the amount of residual monomer components of the polymer contained in the top coat.

At the detachment of the top coat, use may be made of a developer, or a separate peeling agent may be used. The peeling agent preferably consists of a solvent having a lower permeation into the resist film. Detachability by an alkali developer is preferred from the viewpoint of simultaneous attainment of the detachment step with the development processing step for the resist film. The top coat is preferred to be acidic from the viewpoint of detachment with the use of an alkali developer. However, from the viewpoint of non-intermixability with the resist film, the top coat may be neutral or alkaline.

The less the difference in refractive index between the top coat and the liquid for liquid immersion, the higher the resolving power. In an ArF excimer laser (wavelength: 193 nm), when water is used as the liquid for liquid immersion, the top coat for ArF liquid immersion exposure preferably has a refractive index close to that of the liquid for liquid immersion. From the viewpoint of approximation of the refractive index to that of the liquid for liquid immersion, it is preferred for the top coat to contain a fluorine atom. From the viewpoint of transparency and refractive index, it is preferred to reduce the thickness of the film.

Preferably, the top coat does not mix with the film and also does not mix with the liquid for liquid immersion. From this viewpoint, when the liquid for liquid immersion is water, it is preferred for the solvent used in the top coat to be highly insoluble in the solvent used in the composition of the present invention and be a non-water-soluble medium. When the liquid for liquid immersion is an organic solvent, the top coat may be soluble or insoluble in water.

[Solvent]

The photosensitive composition of the present invention may contain a solvent. The solvent is not limited as long as it can be used in the preparation of a positive resist composition through dissolution of the above-mentioned components. As the solvent, there can be mentioned, for example, an organic solvent, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate or an alkyl pyruvate.

As preferred alkylene glycol monoalkyl ether carboxylates, there can be mentioned, for example, propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

As preferred alkylene glycol monoalkyl ethers, there can be mentioned, for example, propylene glycol monomethyl ether, propylene glycol monoethyl ether, propylene glycol monopropyl ether, propylene glycol monobutyl ether, ethylene glycol monomethyl ether and ethylene glycol monoethyl ether.

As preferred alkyl lactates, there can be mentioned, for example, methyl lactate, ethyl lactate, propyl lactate and butyl lactate.

As preferred alkyl alkoxypropionates, there can be mentioned, for example, ethyl 3-ethoxypropionate, methyl 3-methoxypropionate, methyl 3-ethoxypropionate and ethyl 3-methoxypropionate.

As preferred cyclolactones, there can be mentioned, for example, β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

As preferred optionally cyclized monoketone compounds, there can be mentioned, for example, 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

As preferred alkylene carbonates, there can be mentioned, for example, propylene carbonate, vinylene carbonate, ethylene carbonate and butylene carbonate.

As preferred alkyl alkoxyacetates, there can be mentioned, for example, acetic acid 2-methoxyethyl ester, acetic acid 2-ethoxyethyl ester, acetic acid 2-(2-ethoxyethoxy)ethyl ester, acetic acid 3-methoxy-3-methylbutyl ester and acetic acid 1-methoxy-2-propyl ester.

As preferred alkyl pyruvates, there can be mentioned, for example, methyl pyruvate, ethyl pyruvate and propyl pyruvate.

As a preferably employable solvent, there can be mentioned a solvent having a boiling point of 130° C. or above measured at ordinary temperature under ordinary pressure. For example, there can be mentioned cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, acetic acid 2-ethoxyethyl ester, acetic acid 2-(2-ethoxyethoxy)ethyl ester or propylene carbonate.

In the present invention, these solvents may be used either individually or in combination.

In the present invention, a mixed solvent consisting of a mixture of a solvent having a hydroxyl group in its structure and a solvent having no hydroxyl group may be used as the organic solvent.

As the solvent having a hydroxyl group, there can be mentioned, for example, ethylene glycol, ethylene glycol monomethyl ether, ethylene glycol monoethyl ether, propylene glycol, propylene glycol monomethyl ether, propylene glycol monoethyl ether, ethyl lactate or the like. Of these, propylene glycol monomethyl ether and ethyl lactate are especially preferred.

As the solvent having no hydroxyl group, there can be mentioned, for example, propylene glycol monomethyl ether acetate, ethyl ethoxypropionate, 2-heptanone, γ-butyrolactone, cyclohexanone, butyl acetate, N-methylpyrrolidone, N,N-dimethylacetamide, dimethyl sulfoxide or the like. Of these, propylene glycol monomethyl ether acetate, ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent having a hydroxyl group and a solvent having no hydroxyl group is in the range of 0/100 to 99/1, preferably 0/100 to 60/40 and more preferably 0/100. The mixed solvent containing 50 mass % or more of a solvent having no hydroxyl group is especially preferred from the viewpoint of uniform applicability.

The solvent preferably contains propylene glycol monomethyl ether acetate. Two or more types of solvents may be used in combination as a mixed solvent.

[Basic Compound]

The composition of the present invention preferably contains a basic compound so as to decrease any performance alteration over time from exposure to heating.

As preferred basic compounds, there can be mentioned the compounds having the structures of the following formulae (A) to (E).

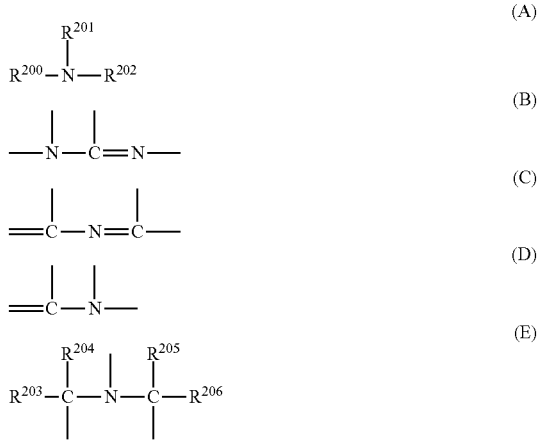

In the general formulae (A) and (E), $R^{200}$, $R^{201}$ and $R^{202}$ may be identical to or different from each other and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded with each other to thereby form a ring. $R^{203}$, $R^{204}$, $R^{205}$ and $R^{206}$ may be identical to or different from each other and each represent an alkyl group having 1 to 20 carbon atoms.

With respect to the above alkyl group, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

More preferably, in these general formulae (A) and (E) the alkyl group is unsubstituted.

As preferred compounds, there can be mentioned guanidine, aminopyrrolidine, pyrazole, pyrazoline, piperazine, aminomorpholine, aminoalkylmorpholine, piperidine and the like. Further, as preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole, 2-phenylbenzoimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned tetrabutylammonium hydroxide, triarylsulfonium hydroxide, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, acetate, adamantane-1-carboxylate, perfluoroalkyl carboxylate and the like. As the compounds with a trialkylamine structure, there can be mentioned tri(n-butyl)amine, tri(n-octyl)amine and the like. As the aniline compounds, there can be mentioned 2,6-diisopropylaniline, N,N-dimethylaniline, N,N-dibutylaniline, N,N-dihexylaniline and the like. As the alkylamine derivatives having a hydroxyl group and/or an ether bond, there can be mentioned ethanolamine, diethanolamine, triethanolamine, N-phenyldiethanolamine, tris(methoxyethoxyethyl)amine and the like. As the aniline derivatives having a hydroxyl group and/or an ether bond, there can be mentioned N,N-bis(hydroxyethyl)aniline and the like.

As preferred basic compounds, there can be further mentioned an amine compound having a phenoxy group, an ammonium salt compound having a phenoxy group, an amine compound having a sulfonic ester group and an ammonium salt compound having a sulfonic ester group.

As the amine compound, use can be made of primary, secondary and tertiary amine compounds. An amine compound having its at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the amine compounds, it is preferred for the alkyl chain to contain an oxygen atom so as to form an oxyalkylene group.

The number of oxyalkylene groups in each molecule is one or more, preferably 3 to 9 and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

As the ammonium salt compound, use can be made of primary, secondary, tertiary and quaternary ammonium salt compounds. An ammonium salt compound having its at least one alkyl group bonded to the nitrogen atom thereof is preferred. Of the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. Of the ammonium salt compounds, it is preferred for the alkyl chain to contain an oxygen atom so as to form an oxyalkylene group. The number of oxyalkylene groups in each molecule is one or more, preferably 3 to 9 and still more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

As the anion of the ammonium salt compounds, there can be mentioned a halide atom, a sulfonate, a borate, a phosphate or the like. Of these, a halide and a sulfonate are preferred. Among halides, chloride, bromide and iodide are especially preferred. Among sulfonates, an organic sulfonate having 1 to 20 carbon atoms is especially preferred. As the organic sulfonate, there can be mentioned an aryl sulfonate and an alkyl sulfonate having 1 to 20 carbon atoms. The alkyl group of the alkyl sulfonate may have a substituent. As the substituent, there can be mentioned, for example, fluorine, chlorine, bromine, an alkoxy group, an acyl group, an aryl group or the like. As specific examples of the alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group of the aryl sulfonate, there can be mentioned a benzene ring, a naphthalene ring or an anthracene ring. The benzene ring, naphthalene ring or anthracene ring may have a substituent. As preferred substituents, there can be mentioned a linear or branched alkyl group having 1 to 6 carbon atoms and a cycloalkyl group having 3 to 6 carbon atoms. As specific examples of the linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compound having a phenoxy group and ammonium salt compound having a phenoxy group are those having a phenoxy group at the end of the alkyl group of the amine compound or ammonium salt compound opposed to the nitrogen atom. The phenoxy group may have a substituent. As the substituent of the phenoxy group, there can be mentioned, for example, an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group or the like. The substitution position of the substituent may be any of 2- to 6-positions. The number of substituents is optional within the range of 1 to 5.

It is preferred that at least one oxyalkylene group exist between the phenoxy group and the nitrogen atom. The number of oxyalkylene groups in each molecule is one or more, preferably 3 to 9 and more preferably 4 to 6. The oxyalkylene group is preferably an oxyethylene group (—$CH_2CH_2O$—) or an oxypropylene group (—$CH(CH_3)CH_2O$— or —$CH_2CH_2CH_2O$—), more preferably an oxyethylene group.

The sulfonic ester group of the amine compound having a sulfonic ester group or ammonium salt compound having a sulfonic ester group may be any of an alkylsulfonic ester, a cycloalkylsulfonic ester and an arylsulfonic ester. In the alkylsulfonic ester, the alkyl group preferably has 1 to 20 carbon atoms. In the cycloalkylsulfonic ester, the cycloalkyl group preferably has 3 to 20 carbon atoms. In the arylsulfonic ester, the aryl group preferably has 6 to 12 carbon atoms. The alkylsulfonic ester, cycloalkylsulfonic ester and arylsulfonic ester may have substituents. As preferred substituents, there can be mentioned a halogen atom, a cyano group, a nitro group, a carboxyl group, a carboxylic ester group and a sulfonic ester group.

It is preferred that at least one oxyalkylene group exist between the sulfonic ester group and the nitrogen atom. The number of oxyalkylene groups in each molecule is one or more, preferably 3 to 9 and more preferably 4 to 6. The oxyalkylene group is preferably an oxyethylene group (—$CH_2CH_2O$—) or an oxypropylene group (—$CH(CH_3)CH_2O$— or —$CH_2CH_2CH_2O$—), more preferably an oxyethylene group.

These basic compounds are used either individually or in combination.

The amount of basic compound used is generally in the range of 0.001 to 10 mass %, preferably 0.01 to 5 mass % based on the solid contents of the composition of the invention.

With respect to the ratio of the acid generator to basic compound used in the composition, preferably, the acid generator/basic compound (molar ratio)=2.5 to 300. The reason for this is that the molar ratio is preferred to be 2.5 or higher from the viewpoint of sensitivity and resolving power. The molar ratio is preferred to be 300 or below from the viewpoint of the inhibition of any resolving power deterioration due to thickening of resist pattern over time from exposure to heating treatment. The acid generator/basic compound (molar ratio) is more preferably in the range of 5.0 to 200, still more preferably 7.0 to 150.

[Surfactant]

The composition of the present invention preferably further contains a surfactant, and more preferably contains any one, or two or more members, of fluorinated and/or siliconized surfactants (fluorinated surfactant, siliconized surfactant and surfactant containing both fluorine and silicon atoms).

The composition of the present invention when containing the above surfactant would, in the use of an exposure light source of 250 nm or below, especially 220 nm or below, realize favorable sensitivity and resolving power and produce a resist pattern with less adhesion and development defects.

As the fluorinated and/or siliconized surfactants, there can be mentioned, for example, those described in JP-A's-62-36663, 61-226746, 61-226745, 62-170950, 63-34540, 7-230165, 8-62834, 9-54432, 9-5988 and 2002-277862 and U.S. Pat. Nos. 5,405,720, 5,360,692, 5,529,881, 5,296,330, 5,436,098, 5,576,143, 5,294,511 and 5,824,451. Any of the following commercially available surfactants can be used as is.

As useful commercially available surfactants, there can be mentioned, for example, fluorinated surfactants/siliconized surfactants, such as Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by Dainippon Ink & Chemicals, Inc.), Surflon S-382, SC101, 102, 103, 104, 105 and 106 (produced by Asahi Glass Co., Ltd.), Troy Sol S-366 (produced by Troy Chemical Co., Ltd.), GF-300 and GF-150 (produced by TOAGOSEI CO., LTD.), Sarfron S-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as the siliconized surfactant.

As the surfactant, besides the above publicly known surfactants, use can be made of a surfactant based on a polymer having a fluorinated aliphatic group derived from a fluorinated aliphatic compound, produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and a poly(oxyalkylene) acrylate and/or poly(oxyalkylene)methacrylate, which copolymer may have an irregular distribution or may result from block copolymerization. As the poly(oxyalkylene) group, there can be mentioned a poly(oxyethylene) group, a poly(oxypropylene) group, a poly(oxybutylene) group or the like. Further, use can be made of a unit having alkylene groups of different chain lengths in a single chain, such as poly(oxyethylene-oxypropylene-oxyethylene block concatenation) or poly(oxyethylene-oxypropylene block concatenation). Moreover, the copolymer from a monomer having a fluorinated aliphatic group and a poly(oxyalkylene) acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene) acrylates (or methacrylates), etc.

For example, as a commercially available surfactant, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene) acrylate (or methacrylate), a copolymer from an acrylate (or methacrylate) having a $C_3F_7$ group, poly(oxyethylene) acrylate (or methacrylate) and poly(oxypropylene) acrylate (or methacrylate), or the like.

In the present invention, surfactants other than the fluorinated and/or siliconized surfactants can also be employed. In particular, there can be mentioned, for example, nonionic surfactants including a polyoxyethylene alkyl ether such as polyoxyethylene lauryl ether, polyoxyethylene stearyl ether, polyoxyethylene cetyl ether or polyoxyethylene oleyl ether, a polyoxyethylene alkylaryl ether such as polyoxyethylene octylphenol ether or polyoxyethylene nonylphenol ether, a polyoxyethylene-polyoxypropylene block copolymer, a sorbitan fatty acid ester such as sorbitan monolaurate, sorbitan monopalmitate, sorbitan monostearate, sorbitan monooleate, sorbitan trioleate or sorbitan tristearate, a polyoxyethylene sorbitan fatty acid ester such as polyoxyethylene sorbitan monolaurate, polyoxyethylene sorbitan monopalmitate, polyoxyethylene sorbitan monostearate, polyoxyethylene sorbitan trioleate or polyoxyethylene sorbitan tristearate, or the like.

These surfactants may be used either individually or in combination.

The amount of each surfactant used is preferably in the range of 0 to 2 mass %, more preferably 0.0001 to 2 mass % and still more preferably 0.0005 to 1 mass % based on the total mass of the composition of the present invention (excluding the solvent).

[Carboxylic Acid Onium Salt]

The composition of the present invention may contain a carboxylic acid onium salt. As the carboxylic acid onium salt, there can be mentioned, for example, a carboxylic acid sulfonium salt, a carboxylic acid iodonium salt, a carboxylic acid ammonium salt or the like. The especially preferred carboxylic acid onium salts are the iodonium salt and the sulfonium salt. It is preferred for the carboxylate residue of the carboxylic acid onium salt for use in the present invention to be one containing neither an aromatic group nor a carbon-carbon double bond. In particular, the especially preferred anion moiety thereof is a linear or branched cycloalkylcarboxylate anion of a single ring or multiple rings having 1 to 30 carbon atoms. A more preferred anion moiety is an anion of carboxylic acid wherein the alkyl group is partially or wholly fluorinated. The alkyl chain may contain an oxygen atom. Accordingly, there would be achieved securement of the transparency in 220 nm or shorter light, enhancement of the sensitivity and resolving power and improvement of the iso-dense bias and exposure margin.

As the fluorinated carboxylic acid anion, there can be mentioned any of the anions of fluoroacetic acid, difluoroacetic acid, trifluoroacetic acid, pentafluoropropionic acid, heptafluorobutyric acid, nonafluoropentanoic acid, perfluorododecanoic acid, perfluorotridecanoic acid, perfluorocyclohexanecarboxylic acid and 2,2-bistrifluoromethylpropionic acid, or the like.

These carboxylic acid onium salts can be synthesized by reacting a sulfonium hydroxide, an iodonium hydroxide or an ammonium hydroxide and a carboxylic acid with silver oxide in an appropriate solvent.

The content ratio of each carboxylic acid onium salt in the composition is generally in the range of 0.1 to 20 mass %, preferably 0.5 to 10 mass % and still more preferably 1 to 7 mass % based on the total solids of the composition.

[Dissolution Inhibiting Compound]

The composition of the present invention may contain a dissolution inhibiting compound of 3000 or less molecular weight that is decomposed by the action of an acid to thereby increase the solubility in an alkali developer (hereinafter referred to as "dissolution inhibiting compound").

From the viewpoint of preventing any lowering of 220 nm or shorter transmission, the dissolution inhibiting compound is preferably an alicyclic or aliphatic compound having an acid-decomposable group, such as any of cholic acid derivatives having an acid-decomposable group described in Proceeding of SPIE, 2724, 355 (1996). The acid-decomposable group and alicyclic structure are the same as described with respect to the resin as the component (B).

When the composition of the present invention is exposed to a KrF excimer laser or irradiated with electron beams, preferred use is made of one having a structure resulting from substitution of the phenolic hydroxyl group of a phenol compound with an acid-decomposable group. The phenol compound preferably contains 1 to 9 phenol skeletons, more preferably 2 to 6 phenol skeletons.

In the present invention, the molecular weight of each dissolution inhibiting compound is 3000 or less, preferably 300 to 3000 and more preferably 500 to 2500.

The amount of dissolution inhibiting compound added is preferably in the range of 3 to 50 mass %, more preferably 5 to 40 mass % based on the total solids of the composition of the present invention.

Specific examples of the dissolution inhibiting compounds will be shown below, which however in no way limit the scope of the present invention.

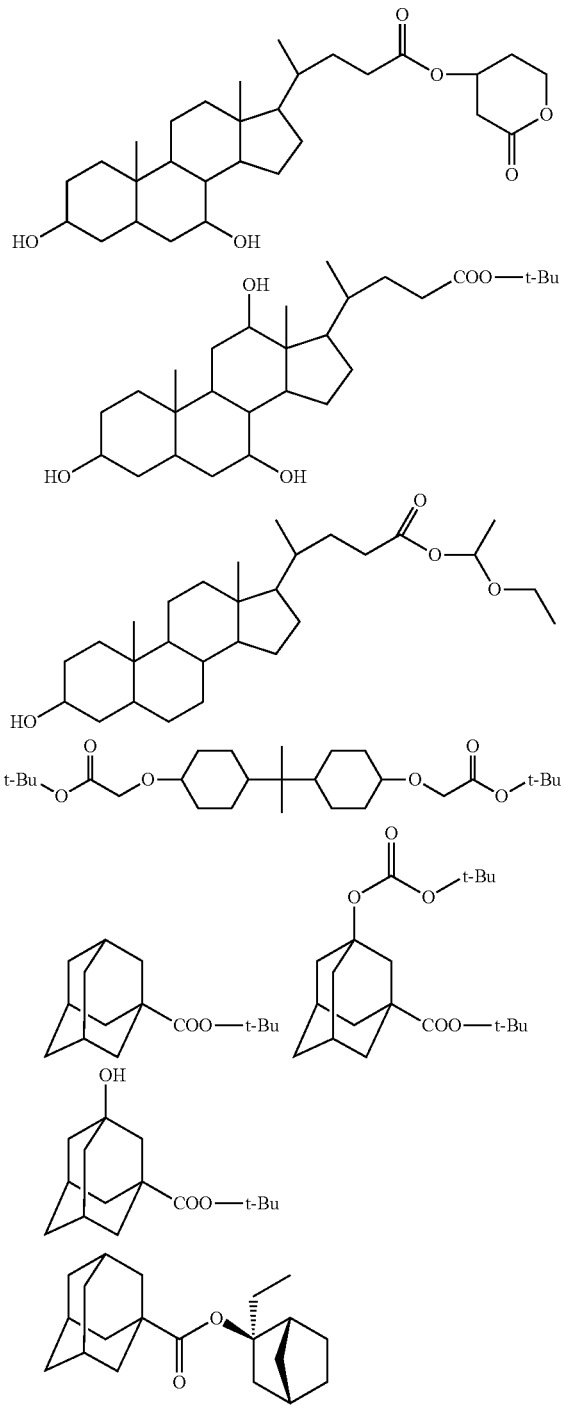

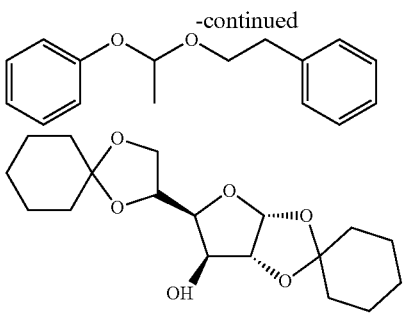

[Other Additives]

The composition of the present invention may further according to necessity contain a dye, a plasticizer, a photosensitizer, a light absorber, a compound capable of increasing the solubility in a developer (for example, a phenolic compound of 1000 or less molecular weight or a carboxylated alicyclic or aliphatic compound), etc.

The above phenolic compound of 1000 or less molecular weight can be easily synthesized by persons of ordinary skill in the art to which the present invention pertains while consulting the processes described in, for example, JP-As 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

Method of Forming Pattern

From the viewpoint of enhancement of resolving power, it is preferred for the composition of the present invention to be used with a coating thickness of 30 to 250 nm. More preferably, the composition is used with a coating thickness of 30 to 200 nm. This coating thickness can be attained by setting the solid content of the composition within an appropriate range so as to cause the composition to have an appropriate viscosity, thereby improving the applicability and film forming property.

The total solids content of the actinic-ray- or radiation-sensitive resin composition is generally in the range of 1 to 10 mass %, preferably 1 to 8 mass % and more preferably 1 to 6 mass %.

The composition of the present invention is used in such a manner that the above components are dissolved in a given organic solvent, preferably the above mixed solvent, and filtered and applied onto a given support in the following manner. The filter medium for the filtration preferably consists of a polytetrafluoroethylene, polyethylene or nylon having a pore size of 0.1 μm or less, especially 0.05 μm or less and more especially 0.03 μm or less.

For example, an actinic-ray- or radiation-sensitive resin composition is applied onto a substrate, such as one for use in the production of precision integrated circuit elements (e.g., silicon/silicon dioxide coating), by appropriate application means, such as a spinner or coater, and dried to thereby form a resist film.

The resist film is exposed through a given mask to actinic rays or radiation, preferably baked (heated), and developed and rinsed. Accordingly, a desirable pattern can be obtained.

As the actinic rays or radiation, there can be mentioned infrared rays, visible light, ultraviolet rays, far ultraviolet rays, extreme ultraviolet rays, X-rays, electron beams or the like. Among them, preferred use is made of far ultraviolet rays of especially 250 nm or less, more especially 220 nm or less and still more especially 1 to 200 nm wavelength, such as a KrF excimer laser (248 nm), an ArF excimer laser (193 nm) and an $F_2$ excimer laser (157 nm), as well as X-rays, electron beams and the like. More preferred use is made of an ArF excimer laser, an $F_2$ excimer laser, EUV (13 nm) and electron beams.

Prior to the formation of a resist film, the substrate may be coated with an antireflection film.

As the antireflection film, use can be made of not only an inorganic film of titanium, titanium oxide, titanium nitride, chromium oxide, carbon, amorphous silicon or the like but also an organic film composed of a light absorber and a polymer material. Also, as the organic antireflection film, use can be made of commercially available organic antireflection films, such as the DUV30 Series and DUV40 Series produced by Brewer Science Inc. and AR-2, AR-3 and AR-5 produced by Shipley Co., Ltd.

In the development operation according to the present invention, use can be made of an alkali developer or a developer containing an organic solvent (hereinafter also referred to as an organic developer). As the alkali developer, use can be made of any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, or the like.

Before the use of the above alkali developer, appropriate amounts of an alcohol and a surfactant may be added thereto.

The alkali concentration of the alkali developer is generally in the range of 0.1 to 20 mass %.

The pH value of the alkali developer is generally in the range of 10.0 to 15.0.

Before the use of the above alkaline aqueous solution, appropriate amounts of an alcohol and a surfactant may be added thereto.

As the organic developer, use can be made of a polar solvent, such as a ketone solvent, an ester solvent, an alcohol solvent, an amide solvent or an ether solvent, and a hydrocarbon solvent.

As the ketone solvent, there can be mentioned, for example, 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate or the like.

As the ester solvent, there can be mentioned, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate or the like.

As the alcohol solvent, there can be mentioned, for example, an alcohol, such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; a glycol ether solvent, such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethylbutanol; or the like.

As the ether solvent, there can be mentioned, for example, not only any of the above-mentioned glycol ether solvents but also dioxane, tetrahydrofuran or the like.

As the amide solvent, there can be mentioned, for example, N-methyl-2-pyrrolidone, N,N-dimethylacetamide, N,N-dimethylformamide, hexamethylphosphoric triamide, 1,3-dimethyl-2-imidazolidinone or the like.

As the hydrocarbon solvent, there can be mentioned, for example, an aromatic hydrocarbon solvent, such as toluene or xylene, or an aliphatic hydrocarbon solvent, such as pentane, hexane, octane or decane.

Two or more of these solvents may be mixed together before use. Alternatively, each of the solvents may be used in a mixture with a solvent other than those mentioned above or water. The water content of the organic developer is preferably below 10 mass %. More preferably, the developer contains substantially no water.

Namely, the amount of organic solvent used in the organic developer is preferably in the range of 90 to 100 mass %, more preferably 95 to 100 mass %, based on the whole amount of the developer.

It is especially preferred for the organic solvent to be one comprising at least one organic solvent selected from the group consisting of a ketone solvent, an ester solvent, an alcohol solvent, an amide solvent and an ether solvent.

According to necessity, an appropriate amount of surfactant can be added to the organic developer.

The surfactant is not particularly limited. For example, use can be made of any of ionic and nonionic fluorinated and/or siliconized surfactants. As such fluorinated and/or siliconized surfactants, there can be mentioned, for example, those described in JP-A's S62-36663, S61-226746, S61-226745, S62-170950, S63-34540, H7-230165, H8-62834, H9-54432 and H9-5988 and U.S. Pat. Nos. 5,405,720, 5,360,692, 5,529,881, 5,296,330, 5,436,098, 5,576,143, 5,294,511 and 5,824,451. Nonionic surfactants are preferred. The nonionic surfactant is not particularly limited. It is more preferred to use a nonionic fluorinated surfactant or siliconized surfactant. The amount of surfactant used is generally in the range of 0.001 to 5 mass %, preferably 0.005 to 2 mass % and more preferably 0.01 to 0.5 mass %, based on the whole amount of the developer.

Pure water can be used as the rinse liquid. Before the use, an appropriate amount of surfactant may be added thereto.

The development operation or rinse operation may be followed by the operation for removing any developer or rinse liquid adhering onto the pattern by the use of a supercritical fluid.

EXAMPLE

The present invention will be described in greater detail below by way of its examples. However, the present invention is in no way limited to these examples.

<Synthesis of Photoacid Generator>

The photoacid generator PAG1 shown below was synthesized in accordance with the following synthetic route.

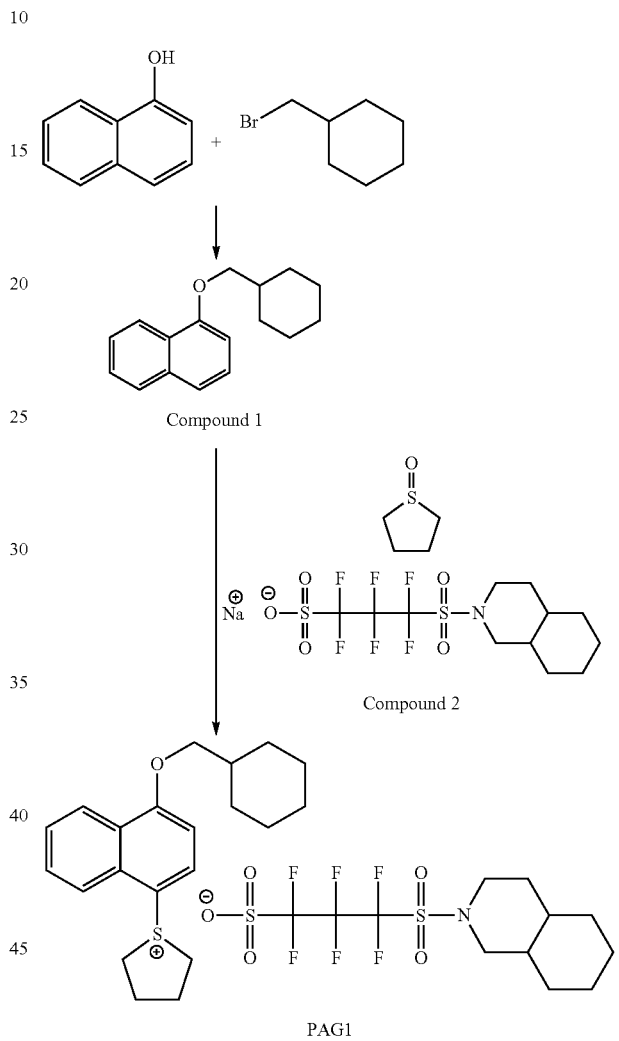

[Synthesis of Compound 1]

In a three-necked flask, 20 g of bromomethylcyclohexane and 12.5 g of 1-naphthol were dissolved in 300 g of NMP. Thereafter, 12 g of potassium carbonate and 14 g of potassium iodide were added to the solution, and heated at 120° C. for 8 hours. Water amounting to 300 g was added to the thus obtained reaction liquid, and was extracted with 100 g of hexane three times. The obtained organic phases were collected, and washed with 100 g of 1N aqueous sodium hydroxide solution once, with 100 g of water once and with 100 g of brine once. The thus washed organic phase was concentrated, thereby obtaining 13 g of compound 1.

An NMR chart of the compound 1 is given in FIG. 1.

[Synthesis of Compound 2]

Compound 2 was synthesized with reference to the process described in JP-A-2005-266799.

161

[Synthesis of PAG1]

In a three-necked flask, 13.1 g of compound 1 was dissolved in 65 g of Eaton reagent. Tetramethylene sulfoxide amounting to 5.7 g was dropped in the solution while stirring, and the stirring was continued for three hours. The thus obtained reaction liquid was poured in 240 g of water, and 25 g of compound 2 and 50 g of chloroform were added to the mixture. An organic phase was separated, and the remaining water phase was further extracted using 50 g of chloroform twice. The thus obtained organic phases were collected, washed with water twice and concentrated. The thus obtained crude product was recrystallized from 20 g of ethyl acetate, thereby obtaining 22 g of PAG1.

Figure 3:
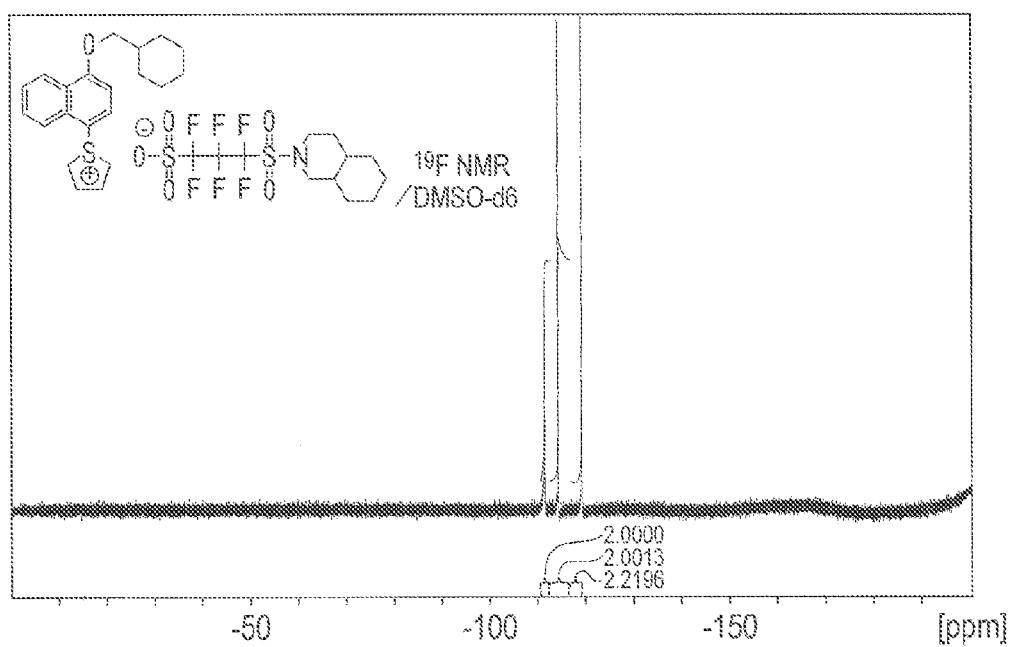
FIG. 3 is the $^{19}$FNMR chart of a photoacid generator (PAG1) prepared in an Example.

NMR charts of the PAG1 are given in FIGS. 2 and 3.

Further, PAG2 to PAG12 were synthesized in the same manner as in the synthesis of PAG1.

(PAG1)

(PAG2)

(PAG3)

-continued

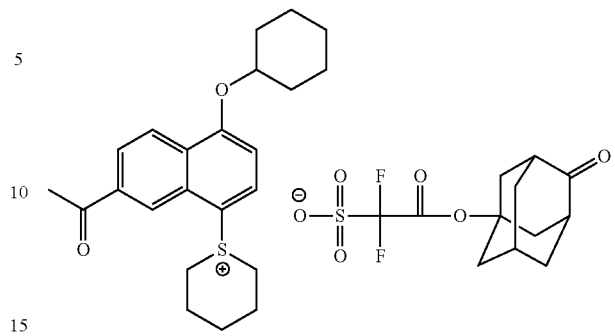
(PAG4)

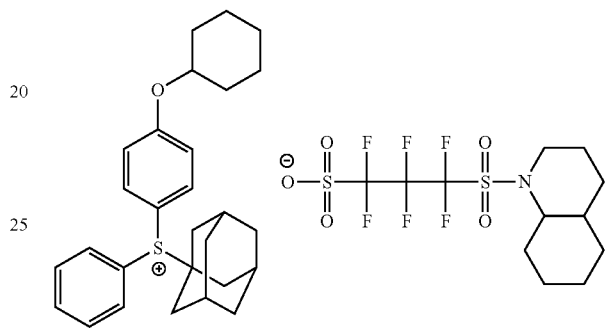
(PAG5)

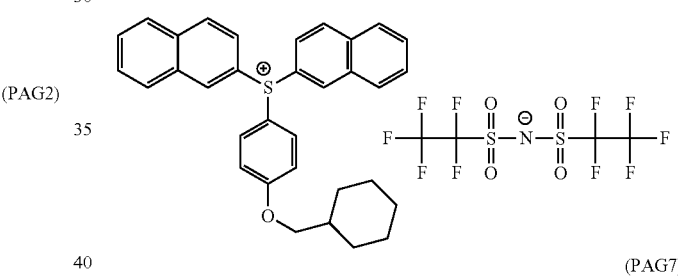
(PAG6)

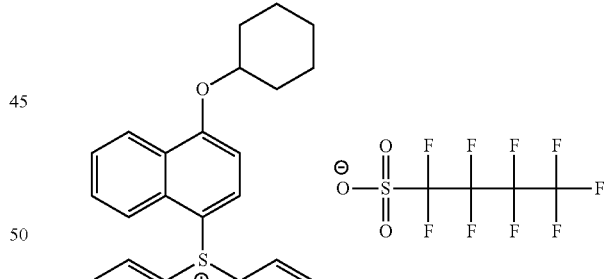
(PAG7)

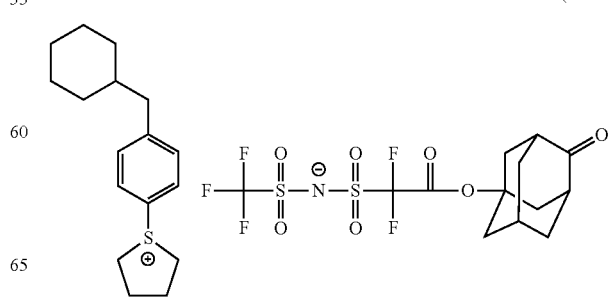
(PAG8)

(PAG9)

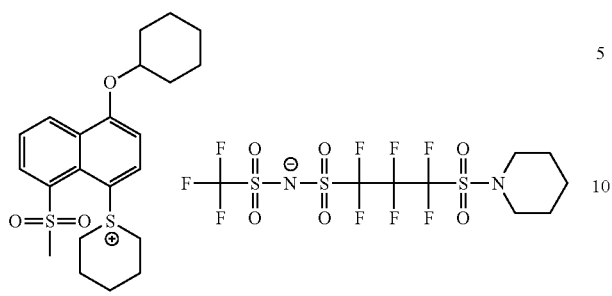

(PAG10)

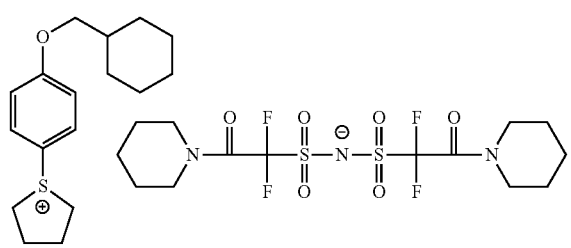

(PAG11)

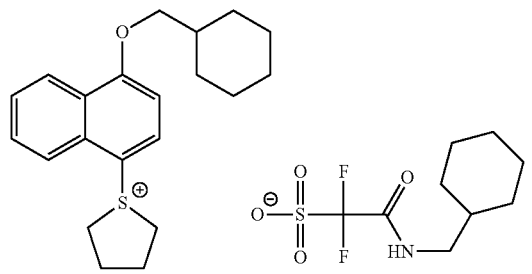

(PAG12)

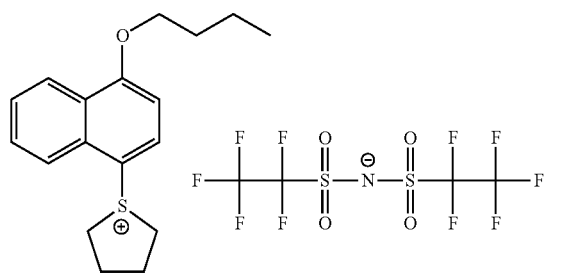

(PAG13)

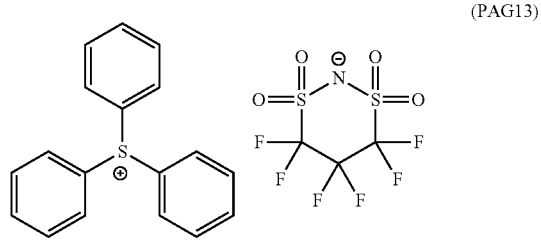

(PAG14)

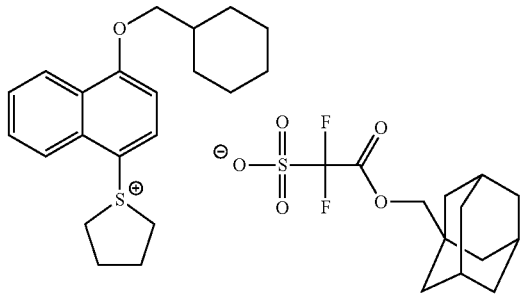

(PAG15)

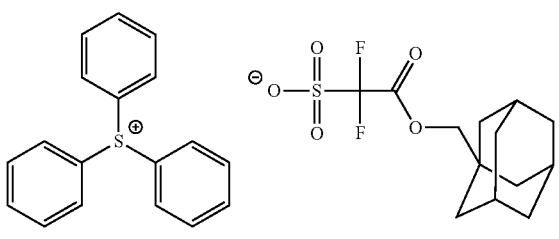

(PAG16)

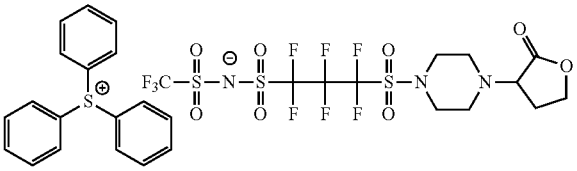

<Synthesis of Resin RA-1>

In a nitrogen stream, 53.22 g of cyclohexanone was placed in a three-necked flask and heated at 80° C. A solution obtained by dissolving 12.42 g of 2-ethyl-2-adamantyl methacrylate, 8.51 g of γ-butyrolactone methacrylate and 5.91 g of 3-hydroxyadamantyl-1-methacrylate and further 1.43 g of polymerization initiator V601 (5.0 mol % based on the monomers, produced by Wako Pure Chemical Industries, Ltd.) in 98.84 g of cyclohexanone was dropped thereinto over a period of 6 hours. After the completion of the dropping, reaction was continued at 80° C. for 2 hours. The resultant reaction liquid was allowed to stand still to cool and was dropped into a mixed liquid consisting of 900 ml of methanol and 100 ml of water over a period of 20 minutes. The thus precipitated powder was collected by filtration and dried, thereby obtaining 18 g of a desired resin (RA-1). The weight average molecular weight of the obtained resin in terms of standard polystyrene molecular weight was 10,700 and the dispersity (Mw/Mn) thereof was 1.81.

The other resins (RA-2 to RA-12) were synthesized in the same manner. The weight average molecular weight of each of the resins was regulated by changing the amount of initiator added.

The repeating units (molar ratio), weight average molecular weight (Mw) and dispersity (Mw/Mn) of each of the obtained resins are given below.

(RA-1) 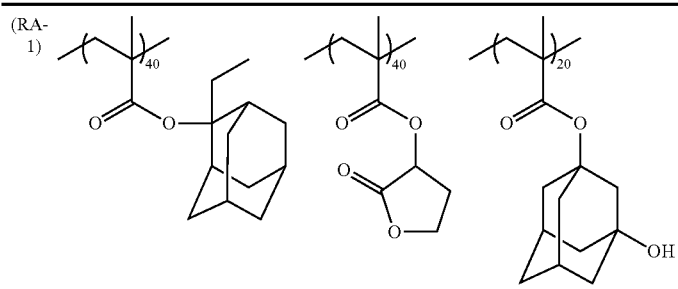 Mw = 10700; Mw/Mn = 1.81
(RA-2) 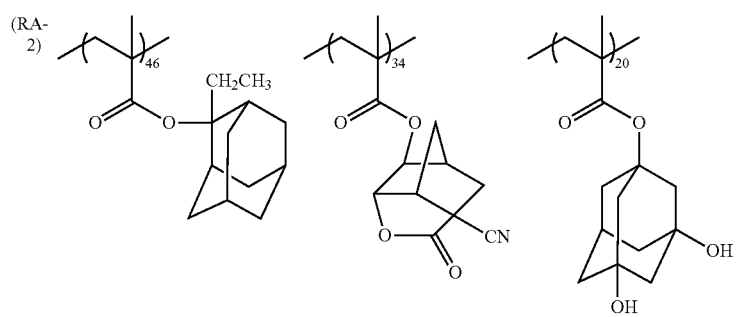 Mw = 9400; Mw/Mn = 1.78
(RA-3) 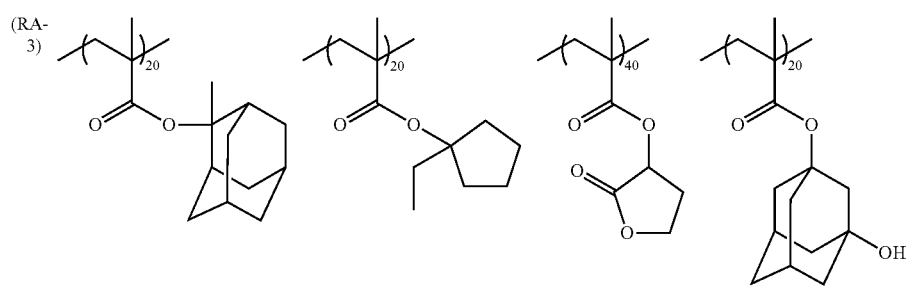 Mw = 13700; Mw/Mn = 1.89
(RA-4) 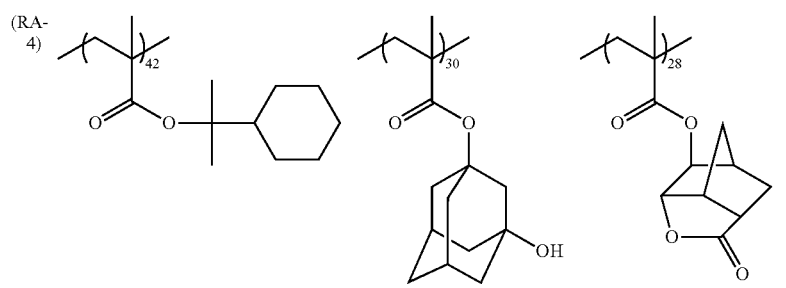 Mw = 10300; Mw/Mn = 1.90
(RA-5) 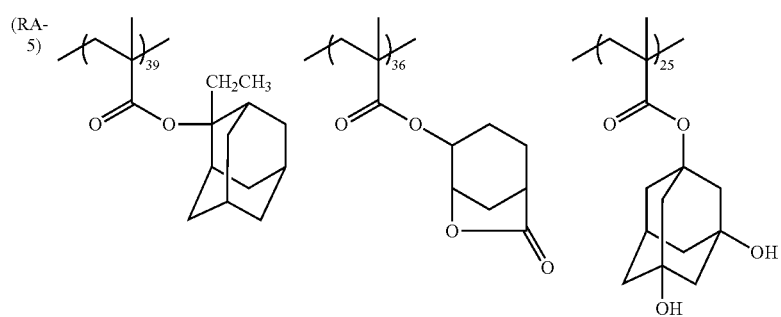 Mw = 8900; Mw/Mn = 1.80

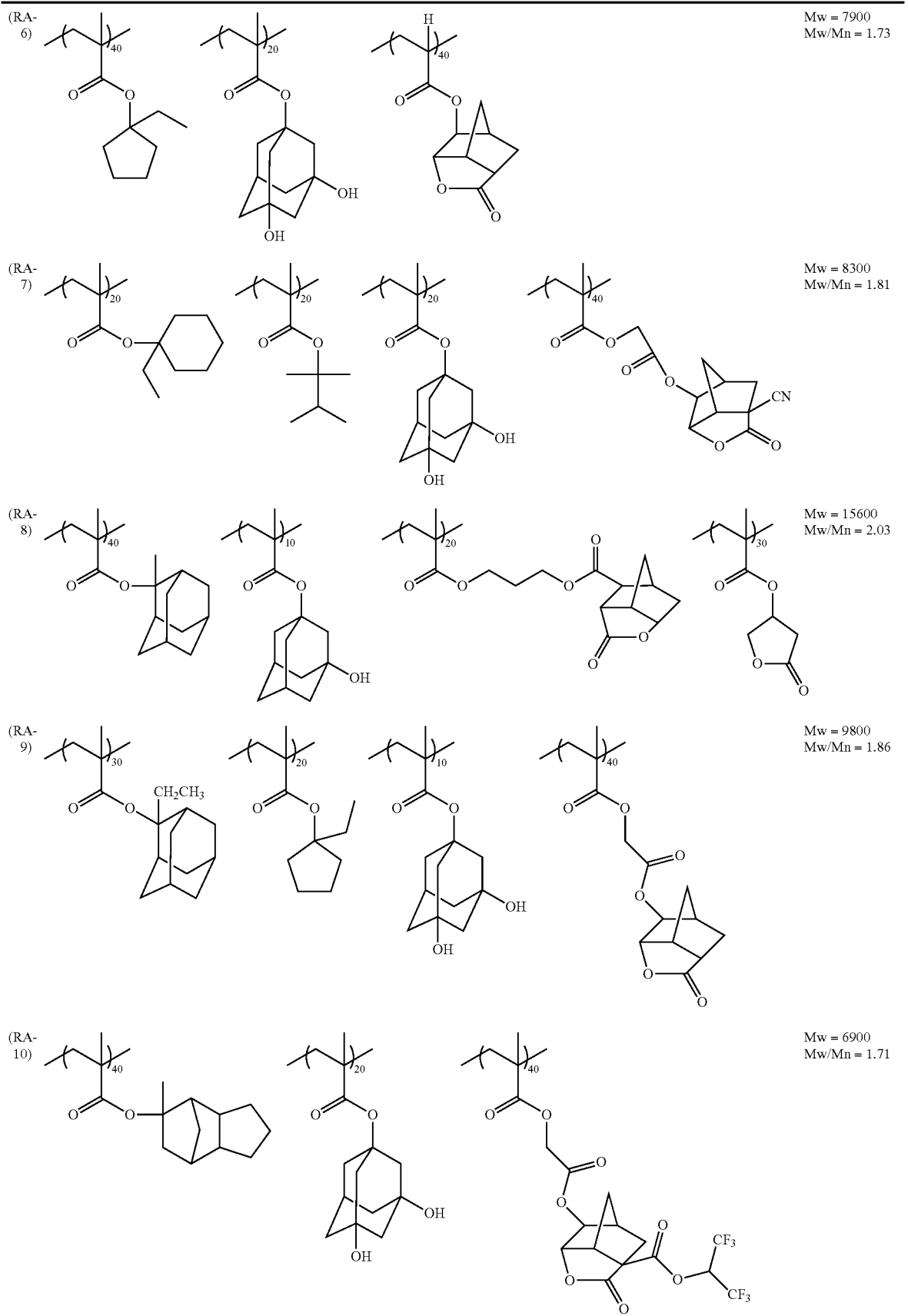

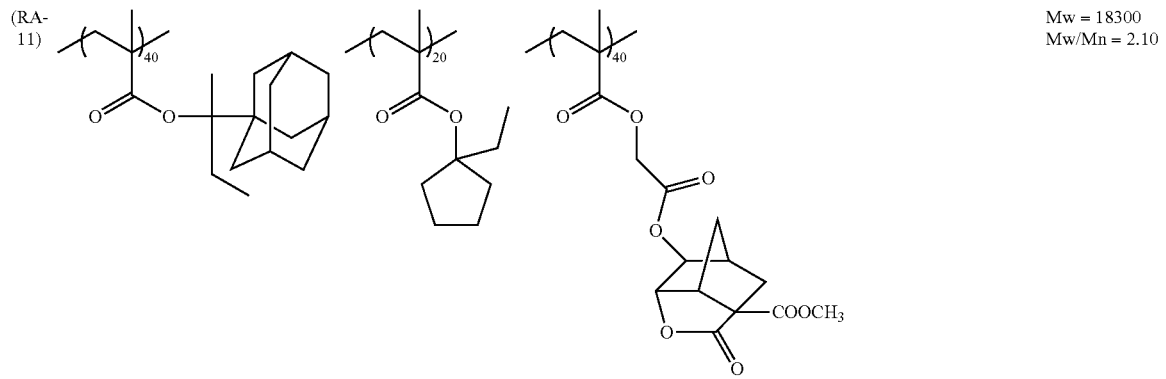
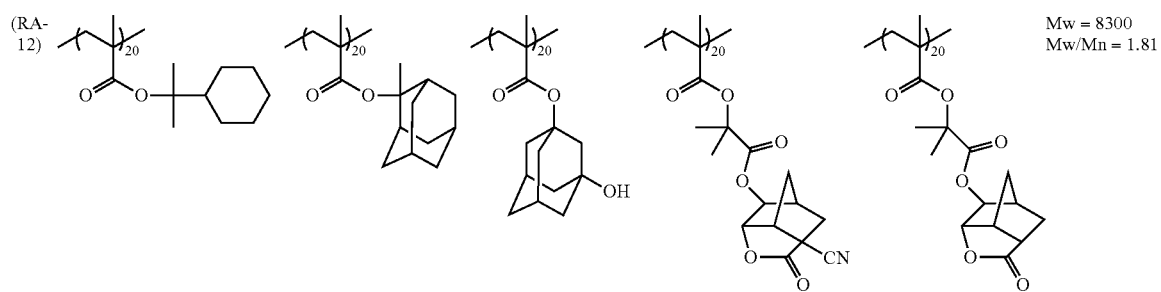
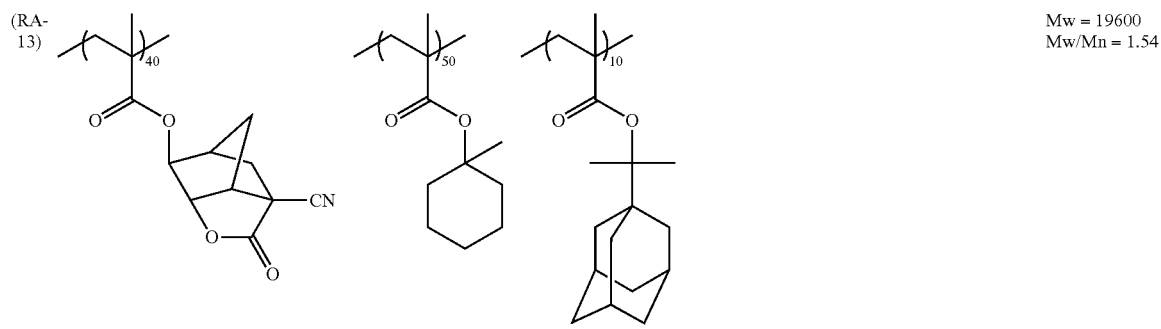
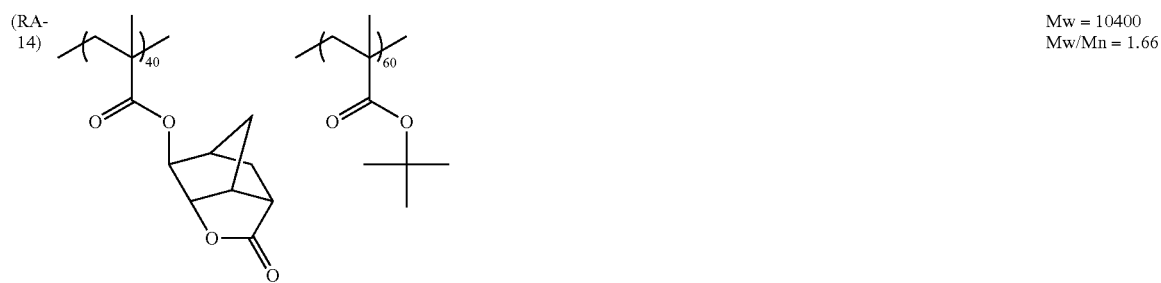

<Preparation of Actinic-Ray- or Radiation-Sensitive Resin Composition>

Dissolution of the components in the solvents as indicated in Table 2 below was carried out, thereby obtaining solutions of 5 mass % solid content. The solutions were passed through a polyethylene filter of 0.03 μm pore size, thereby obtaining compositions (positive resist compositions). The thus obtained positive resist solutions were evaluated by the following methods, and the results are given in the same table.

<Evaluation of Resist>
(Exposure Condition (1) ArF Dry Exposure)

An organic antireflection film ARC29A (produced by Nissan Chemical Industries, Ltd.) was applied onto a silicon wafer and baked at 205° C. for 60 seconds, thereby forming a 78 nm-thick antireflection film. Each of the prepared positive resist compositions was applied thereonto and baked at 130° C. for 60 seconds, thereby forming a 120 nm-thick resist film. The resultant wafer was exposed through a 6% half-tone

TABLE 2

|  | (A) Acid Generator (g) | (B) Resin (10 g) | (C) Resin (g) | Basic compound (g) | Surfactant (100 ppm) | Solvent (mass ratio) | Exposure condition | EL (%) | LER (nm) | Development defect |
|---|---|---|---|---|---|---|---|---|---|---|
| Ex. 1 | PAG1 (2.1) | RA-1 | — | D-1 (0.4) | W-2 | S1/S3 (60/40) | 1 | 16.9 | 5.9 | o |
| Ex. 2 | PAG2 (3.1) | RA-2 | HR-26 (0.6) | D-2 (0.3) | W-3 | S1/S3 (70/30) | 2 | 14.6 | 6.8 | o |
| Ex. 3 | PAG3/PAG1 (2.7/0.6) | RA-3 | HR-56 (0.5) | D-3 (0.3) | — | S1/S3 (80/20) | 2 | 16.8 | 6.2 | o |
| Ex. 4 | PAG4 (3.2) | RA-4 | HR-4 (0.1) | D-4 (0.3) | W-4 | S1/S2 (80/20) | 2 | 15.7 | 6.9 | o |
| Ex. 5 | PAG5/PAG2 (2.5/1.5) | RA-5 | HR-17 (0.5) | D-5 (0.2) | W-1 | S1/S4 (95/5) | 2 | 16.2 | 6.2 | o |
| Ex. 6 | PAG6 (3.1) | RA-6 | HR-26 (0.6) | D-1 (0.3) | W-1 | S1/S3 (60/40) | 2 | 15.9 | 6.7 | o |
| Ex. 7 | PAG7 (3.9) | RA-7 | HR-47 (0.3) | D-2 (0.2) | W-4 | S1/S4 (95/5) | 2 | 15.5 | 7.0 | o |
| Ex. 8 | PAG8 (3.1) | RA-8 | HR-56 (0.5) | D-3/D-1 (0.2/0.1) | W-1 | S1/S2 (80/20) | 2 | 16.8 | 6.3 | o |
| Ex. 9 | PAG9 (3.5) | RA-9 | HR-4 (0.1) | D-1 (0.2) | W-1 | S1/S5 (95/5) | 2 | 16.8 | 6.1 | o |
| Ex. 10 | PAG10 (3.3) | RA-10 | HR-57 (0.4 | D-2 (0.2) | W-1 | S1/S3 (60/40) | 2 | 16.0 | 6.4 | o |
| Ex. 11 | PAG8 (3.3) | RA-11 | — | D-3 (0.4) | W-1 | S1/S5 (95/5) | 1 | 16.3 | 6.1 | o |
| Ex. 12 | PAG1 (1.8) | RA-12 | HR-17 (0.5 | D-4 (0.3) | W-2 | S1/S3 (60/40) | 2 | 15.9 | 6.8 | o |
| Ex. 13 | PAG1/PAG12 (2.2/0.5) | RA-3 | HR-17 (0.5) | D-4 (0.4) | W-2 | S1/S3 (60/40) | 2 | 16.2 | 6.1 | o |
| Ex. 14 | PAG8 (3.3) | RA-5/RA-7 (5 g/5 g) | HR-47 (0.3) | D-5 (0.2) | W-1 | S1/S4 (95/5) | 2 | 16.8 | 6.1 | o |
| Ex. 15 | PAG11 (2.5) | RA-11 | HR-26/HR-56 (0.3/0.3) | D-2 (0.2) | W-4 | S1/S4 (95/5) | 2 | 15.9 | 6.3 | o |
| Comp. 1 | PAG12 (3.6) | RA-2 | HR-4 (0.4) | D-1 (0.2) | W-1 | S1/S3 (70/30) | 2 | 12.5 | 8.2 | x |
| Comp. 2 | PAG13 (3.3) | RA-3 | HR-26 (0.5) | D-4 (0.2) | W-1 | S1/S3 (70/30) | 2 | 13.3 | 7.7 | x |

The brevity codes appearing in the Table 2 have the following meanings.

[Solvent]
S1: propylene glycol monomethyl ether acetate (PGMEA),
S2: 2-heptanone,
S3: cyclohexanone,
S4: γ-butyrolactone, and
S5: propylene glycol monomethyl ether (PGME).

[Surfactant]
W-1: Megafac F176 (produced by Dainippon Ink & Chemicals, Inc., fluorinated),
W-2: Megafac R08 (produced by Dainippon Ink & Chemicals, Inc., fluorinated and siliconized),
W-3: polysiloxane polymer KP-341 (produced by Shin-Etsu Chemical Co., Ltd., siliconized), and
W-4: Troy Sol S-366 (produced by Troy Chemical Co., Ltd.).

[Basic Compound]
D-1: triphenylsulfonium acetate,
D-2: 2,6-diisopropylaniline,
D-3: triethanolamine,
D-4: N,N-dibutylaniline, and
D-5: 2-phenylbenzimidazole.

mask of 75 nm 1:1 line and space pattern by means of an ArF excimer laser scanner (manufactured by ASML, PAS5500/1100, NA 0.75). Thereafter, the exposed wafer was baked at 130° C. for 60 seconds, developed with an aqueous solution of tetramethylammonium hydroxide (2.38 mass %) for 30 seconds, rinsed with pure water and spin dried, thereby obtaining a resist pattern.

[Exposure Latitude (EL)]

The optimum exposure amount was defined as the exposure amount that reproduced a 75 nm 1:1 line and space mask pattern. The exposure amount width in which when the exposure amount was varied, the pattern size allowed 75 nm±10% was measured. The exposure latitude was the quotient of the value of the exposure amount width divided by the optimum exposure amount, the quotient expressed by a percentage. The greater the value of the exposure latitude, the less the change of performance by exposure amount changes and the better the exposure latitude.

[Line Edge Roughness (LER)]

In the measurement of line edge roughness, a 75 nm isolated pattern produced at the optimum exposure amount was observed by means of a critical dimension SEM (model S-9260 manufactured by Hitachi, Ltd.). In a 5 µm region along the longitudinal direction of the line pattern, the distances of actual edges from a reference line on which edges were to be present were measured on 50 points. The standard deviation of measurements was determined, and 3σ was computed. The smaller the value thereof, the more favorable the performance exhibited.

[Development Defect]

Random-mode measurement was carried out by means of a defect inspection apparatus KLA2360 (trade name) manufactured by KLA-Tencor Corporation. In the defect inspection apparatus, the pixel size was set at 0.16 µm and the threshold value at 20. Any development defects extracted from differences generated by superimposition between a comparative image and the pixel unit were detected, and the number of development defects per area ($cm^2$) was calculated. The evaluation marks o, Δ and x were given when the calculated value was less than 0.5, 0.5 to less than 0.8 and 0.8 or greater, respectively. The smaller the value, the more favorable the performance exhibited.

(Exposure Condition (2) ArF Liquid Immersion Exposure)

An organic antireflection film ARC29A (produced by Nissan Chemical Industries, Ltd.) was applied onto a silicon wafer and baked at 205° C. for 60 seconds, thereby forming a 98 nm-thick antireflection film. Each of the prepared positive resist compositions was applied thereonto and baked at 130° C. for 60 seconds, thereby forming a 120 nm-thick resist film. The resultant wafer was exposed through a 6% half-tone mask of 65 nm 1:1 line and space pattern by means of an ArF excimer laser liquid-immersion scanner (manufactured by ASML, XT1700i, NA 1.20, C-Quad, outer sigma 0.981, inner sigma 0.895, XY deflection). Ultrapure water was used as the immersion liquid. Thereafter, the exposed wafer was baked at 130° C. for 60 seconds, developed with an aqueous solution of tetramethylammonium hydroxide (2.38 mass %) for 30 seconds, rinsed with pure water and spin dried, thereby obtaining a resist pattern.

[Exposure Latitude (EL)]

The optimum exposure amount was defined as the exposure amount that reproduced a 65 nm 1:1 line and space mask pattern. The exposure amount width in which when the exposure amount was varied, the pattern size allowed 65 nm±10% was measured. The exposure latitude was the quotient of the value of the exposure amount width divided by the optimum exposure amount, the quotient expressed by a percentage. The greater the value of the exposure latitude, the less the change of performance by exposure amount changes and the better the exposure latitude.

[Line Edge Roughness (LER)]

In the measurement of line edge roughness, a 65 nm isolated pattern produced at the optimum exposure amount was observed by means of a critical dimension SEM (model S-9260 manufactured by Hitachi, Ltd.). In a 5 µm region along the longitudinal direction of the line pattern, the distances of actual edges from a reference line on which edges were to be present were measured on 50 points. The standard deviation of measurements was determined, and 3σ was computed. The smaller the value thereof, the more favorable the performance exhibited.

[Development Defect]

Random-mode measurement was carried out by means of a defect inspection apparatus KLA2360 (trade name) manufactured by KLA-Tencor Corporation. In the defect inspection apparatus, the pixel size was set at 0.16 µm and the threshold value at 20. Any development defects extracted from differences generated by superimposition between a comparative image and the pixel unit were detected, and the number of development defects per area ($cm^2$) was calculated. The evaluation marks o, Δ and x were given when the calculated value was less than 0.5, 0.5 to less than 0.8 and 0.8 or greater, respectively. The smaller the value, the more favorable the performance exhibited.

It is apparent from the above evaluation results that regardless of whether use is made of dry exposure or liquid-immersion exposure, development defects can be suppressed and a pattern excelling in exposure latitude and line edge roughness can be provided by use of the actinic-ray- or radiation-sensitive resin composition of the present invention.

<Evaluation of Resist Using Organic Solvent Developer>

(Preparation of Resist)

As indicated in the following table, individual components were dissolved in solvents, thereby obtaining solutions each of 3.8 mass % solid content. The solutions were each passed through a polyethylene filter of 0.03 µm pore size, thereby obtaining actinic-ray- or radiation-sensitive resin compositions (resist compositions).

(Evaluation of Resist)

An organic antireflection film ARC29SR (produced by Nissan Chemical Industries, Ltd.) was applied onto a silicon wafer and baked at 205° C. for 60 seconds, thereby forming a 95 nm-thick antireflection film. Each of the prepared actinic-ray- or radiation-sensitive resin compositions was applied thereonto and baked (prebaked, PB) at 100° C. for 60 seconds, thereby forming a 100 nm-thick resist film.

The resultant wafer was patternwise exposed through a half-tone mask of square array of 60 nm hole size and 90 nm inter-hole pitch to light by means of an ArF excimer laser liquid-immersion scanner (manufactured by ASML, XT1700i, NA 1.20, C-Quad, outer sigma 0.900, inner sigma 0.812, XY deflection). Ultrapure water was used as the immersion liquid. Thereafter, the exposed wafer was baked (post-exposure baked, PEB) at 105° C. for 60 seconds. The baked wafer was developed by puddling the same with a negative developer (butyl acetate) for 30 seconds, and the developed wafer was rinsed by puddling the same with a rinse liquid (methyl isobutyl carbinol (MIBC)) for 30 seconds. Thereafter, the wafer was rotated at a rotating speed of 4000 rpm for 30 seconds. Thus, a 45 nm contact hole pattern was obtained.

(Method of Evaluation)

[Exposure Latitude (EL, %)]

The hole sizes were observed by means of a critical dimension scanning electron microscope (SEM model S-9380II manufactured by Hitachi, Ltd.). The sensitivity ($E_{opt}$, $mJ/cm^2$) was defined as the optimum exposure amount in which a contact hole pattern of 45 nm hole size was resolved. On the basis of the thus determined optimum exposure amount ($E_{opt}$), the exposure amounts that caused the hole size to become ±10% of the target 45 nm (namely, 40.5 nm and 49.5 nm) were determined. Then, the exposure latitude (EL, %) defined by the following formula was calculated. The larger the value of EL, the favorably smaller the performance change by changing of the exposure amount.

[EL(%)]=[(exposure amount for 40.5 nm hole size)−(exposure amount for 49.5 nm hole size)]/$E_{opt}$.

[Local Pattern Dimension Uniformity (Local CDU, nm)]

Within one shot made by exposure in the optimum exposure amount determined at the evaluation of exposure latitude, the sizes of a total of 500 holes, namely, arbitrary 25 holes in each of twenty 1 µm interspaced localities, were measured. The standard deviation of measurements was determined, and 3σ was computed therefrom. The smaller the value thereof, the smaller the dimension variation, namely, the more favorable the performance exhibited.

[Thickness of Pattern Portion (nm)]

The shape of cross section of each of the patterns formed in the above optimum exposure amount was observed by means of a scanning electron microscope (model S-4800 manufactured by Hitachi, Ltd.). The height of pattern at portions of each hole pattern where the resist remained was measured. The larger the value thereof, the favorably less the film thinning.

The obtained evaluation results are given in Table 3 below.

TABLE 3

|  | (A) Acid generator | | (B) Resin | (C) Resin | Basic compound | Surfactant | Solvent (mass | Local CDU | EL | Thickness of pattern portion |
| --- | --- | --- | --- | --- | --- | --- | --- | --- | --- | --- |
|  | (mass ratio) | (g) | (10 g) | (g) | (g) | (100 ppm) | ratio) | (nm) | (%) | (nm) |
| Ex. 16 | PAG1/PAG15 (70/30) | 1.05 | RA-13 | HR-47 (0.06) | D-5 (0.86) | W-2 | S1/S2 (90/10) | 5.2 | 18.1 | 82 |
| Ex. 17 | PAG14/PAG16 (60/40) | 1.20 | RA-14 | HR-47 (0.08) | — | W-2 | S1/S3 (80/20) | 4.8 | 17.4 | 82 |
| Comp. Ex. 3 | PAG12/PAG16 (50/50) | 1.05 | RA-14 | HR-47 (0.07) | — | W-2 | S1/S5 (60/40) | 9.9 | 9.6 | 68 |

It has been proved that by using an organic developer in the operation of developing the resist composition of the present invention, the uniformity of local pattern dimension can be enhanced, the exposure latitude can be increased, and a decrease of film thickness at pattern portions formed by the development, known as film thinning, can be suppressed.

What is claimed is:

1. An actinic-ray- or radiation-sensitive resin composition comprising any of the compounds (A) of general formula (I) below that when exposed to actinic rays or radiation, generates an acid and a resin (B) whose rate of dissolution into an alkali developer is increased by the action of an acid,

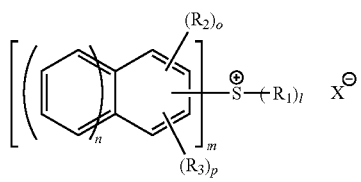

(I)

wherein $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; $X^-$ represents a counter anion; and n is 0 or 1, m is an integer of 1 to 3, l=3−m, o is an integer of 1 to 7, and p is an integer of 0 to 6, provided that when l is 2, two $R_1$s may be identical to or different from each other, and may be bonded to each other to thereby form a ring, and that $R_2$s, $R_3$s, and n's may be identical to or different from each other, and at least one $R_2$ is an alkoxy group having a total of 7 or more carbon atoms in which a monocycloalkyl group is contained, the at least one $R_2$ is substituted at a para position of an aromatic ring substituted with S+, and the para position is defined with respect to a substituting position of S+.

2. The composition according to claim 1, wherein in general formula (I), at least one $R_2$ is a substituted alkoxy group having a total of 7 or more carbon atoms in which a monocycloalkyl group is contained.

3. The composition according to claim 1, wherein in general formula (I), n=1, m=1, l=2, and two $R_1$s are optionally substituted alkyl groups or are bonded to each other to thereby form a ring.

4. The composition according to claim 1, further comprising a hydrophobic resin (C).

5. The composition according to claim 4, wherein the hydrophobic resin (C) contains at least a fluorine atom or a silicon atom.

6. The composition according to claim 4, wherein the hydrophobic resin (C) has at least one group selected from the groups (x) to (z), which are:

(x) an alkali soluble group;
(y) a group that is decomposed by the action of an alkali developer, resulting in an increase of solubility in the alkali developer; and
(z) a group that is decomposed by the action of an acid.

7. The composition according to claim 4, wherein the hydrophobic resin (C) is in the range between 0.01 and 10 mass %.

8. The composition according to claim 1, wherein in general formula (I), $X^-$ has any of the structures of general formula (II) below,

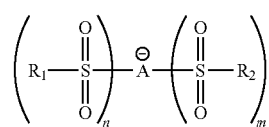

(II)

wherein A represents an oxygen atom, a nitrogen atom or a carbon atom; $R_1$ represents a monovalent organic group containing a fluorine atom; and $R_2$ represents a fluorine atom, an optionally substituted alkyl group, an optionally substituted cycloalkyl group or an optionally substituted aryl group, provided that when A is an oxygen atom, n=1 and m=0; when A is a nitrogen atom, n+m=2, n=1 or 2, and m=0 or 1, and when A is a carbon atom, n+m=3, n is an integer of 1 to 3, and m is an integer of 0 to 2, and that when n is 2 or greater, the two or more $R_1$s may be identical to or different from each other, and $R_1$s may be bonded to each other to thereby form a ring.

9. The composition according to claim 1, wherein any protonic solvent is not contained.

10. The composition according to claim 1, wherein n=1.

11. The composition according to claim 10, wherein S⁺ in general formula (I) is substituted at the 1-position of the naphthalene-ring that is formed when n=1.

12. The composition according to claim 1, wherein at least one $R_2$ that is an alkoxy group having a total of 7 or more carbon atoms in which a monocycloalkyl group is contained is an alkoxy group substituted with a monocycloalkyl group.

13. The composition according to claim 12, wherein at least one of the $R_2$ that is an alkoxy group substituted with a monocycloalkyl group is a methoxy group substituted with a cyclohexyl group.

14. The composition according to claim 1, wherein in general formula (I), m=1, l=2, and two $R_1$s are bonded to each other to thereby form a ring.

15. The composition according to claim 14, wherein the ring formed by bonding two $R_1$s has 5-7 members.

16. An actinic-ray- or radiation-sensitive resin composition comprising any of the compounds (A) of general formula (I) below that when exposed to actinic rays or radiation, generates an acid, a resin (B) whose rate of dissolution into an alkali developer is increased by the action of an acid, and a hydrophobic resin (C),

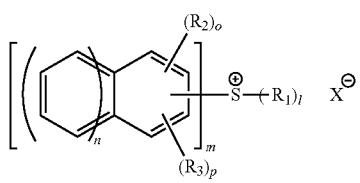

(I)

wherein $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; X⁻ represents a counter anion; and n=1, m=1, l=2, o is an integer of 1 to 7, and p is an integer of 0 to 6, wherein two $R_1$s are bonded to each other to thereby form a ring, $R_2$s and $R_3$s may be identical to or different from each other, at least one $R_2$ is an alkoxy group substituted with a monocycloalkyl group and having a total of 7 or more carbon atoms, and S⁺ is substituted at the 1-position of the naphthalene-ring that is formed when n=1.

17. An actinic-ray- or radiation-sensitive resin composition comprising any of the compounds (A) of general formula (I) below that when exposed to actinic rays or radiation, generates an acid and a resin (B) whose rate of dissolution into an alkali developer is increased by the action of an acid,

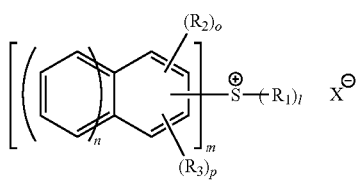

(I)

wherein $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; X⁻ represents a counter anion; and n is 0, m is an integer of 1 to 3, l=3−m, o is an integer of 1 to 7, and p is an integer of 0 to 6, provided that when l is 2, two $R_1$s may be identical to or different from each other, and may be bonded to each other to thereby form a ring, and that $R_2$s, $R_3$s, and n's may be identical to or different from each other, and at least one $R_2$ is an alkoxy group having a total of 7 or more carbon atoms in which a monocycloalkyl group is contained.

18. Compounds of general formula (I),

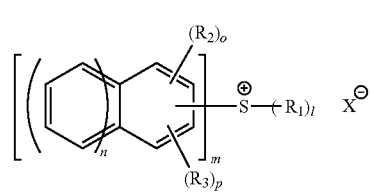

(I)

wherein $R_1$ represents an optionally substituted aryl group, an optionally substituted alkyl group, an optionally substituted aralkyl group or an optionally substituted mono- or polycycloalkyl group; $R_2$ represents a group having a monocycloalkyl skeleton; $R_3$ represents an alkyl group or an electron withdrawing group; X⁻ represents a counter anion; and n is 0 or 1, m is an integer of 1 to 3, l=3−m, o is an integer of 1 to 7, and p is an integer of 0 to 6, provided that when l is 2, two $R_1$s may be identical to or different from each other, and may be bonded to each other to thereby form a ring, and that $R_2$s, $R_3$s, and n's may be identical to or different from each other, and at least one $R_2$ is an alkoxy group having a total of 7 or more carbon atoms in which a moncycloalkyl group is contained, the at least one $R_2$ is substituted at a para position of an aromatic ring substituted with S+, and the para position is defined with respect to a substituting position of S+.

19. The compounds according to claim 18, wherein in general formula (I), at least one $R_2$ is a substituted alkoxy group having a total of 7 or more carbon atoms in which a monocycloalkyl group is contained.

20. The compounds according to claim 19, wherein in general formula (I), n=1, m=1, l=2, and two $R_1$s are optionally substituted alkyl groups or are bonded to each other to thereby form a ring.

21. A method of forming a pattern, comprising forming the composition of claim 1 into a film, exposing the film and developing the exposed film.

22. The method of forming a pattern according to claim 21, wherein the film is exposed through a liquid for liquid immersion.

* * * * *